(12) United States Patent
Hauser et al.

(10) Patent No.: US 12,109,327 B2
(45) Date of Patent: Oct. 8, 2024

(54) SCAFFOLDS FROM SELF-ASSEMBLING TETRAPEPTIDES SUPPORT 3D SPREADING, OSTEOGENIC DIFFERENTIATION AND ANGIOGENESIS OF MESENCHYMAL STEM CELLS

(71) Applicant: KING ABDULLAH UNIVERSITY OF SCIENCE AND TECHNOLOGY, Thuwal (SA)

(72) Inventors: Charlotte A. E. Hauser, Thuwal (SA); Salwa Alshehri, Thuwal (SA); Hepi H. Susapto, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 214 days.

(21) Appl. No.: 17/401,542

(22) Filed: Aug. 13, 2021

(65) Prior Publication Data
US 2022/0054706 A1    Feb. 24, 2022

Related U.S. Application Data

(60) Provisional application No. 63/067,962, filed on Aug. 20, 2020, provisional application No. 63/067,913, filed on Aug. 20, 2020.

(51) Int. Cl.
*A61L 27/36*    (2006.01)
*A61L 27/22*    (2006.01)
(Continued)

(52) U.S. Cl.
CPC ............. *A61L 27/365* (2013.01); *A61L 27/22* (2013.01); *B33Y 10/00* (2014.12); *B33Y 70/00* (2014.12);
(Continued)

(58) Field of Classification Search
CPC .... A61L 27/365; A61L 27/22; A61L 2430/02; B33Y 10/00; B33Y 70/00; B33Y 80/00;
(Continued)

(56) References Cited

U.S. PATENT DOCUMENTS

| 5,445,612 A | 8/1995 | Terakura et al. |
| 8,729,032 B2 | 5/2014 | Nagai et al. |

(Continued)

FOREIGN PATENT DOCUMENTS

| CN | 105085622 A | 11/2015 |
| CN | 105 881 908 A | 8/2016 |

(Continued)

OTHER PUBLICATIONS

Liu et al., "Stiffness-mediated mesenchymal stem cell fate decision in 3D-bioprinted hydrogels" in Burns & Trauma, vol. 8, 2020 published Jul. 27, 2020 (Year: 2020).*

(Continued)

*Primary Examiner* — Blessing M Fubara
(74) *Attorney, Agent, or Firm* — Ajay A. Jagtiani; Miles & Stockbridge P.C.

(57) ABSTRACT

The present disclosure relates generally to an osteo-tissue graft capable of promoting bone tissue growth and regeneration, comprising at least one self-assemble peptide and mesenchymal stem cells (MSCs) in accordance with the present invention and a method of preparing such an osteo-tissue graft. The grafts are suitable for treatment of bone disorder or damages through tissue engineering, cellular replacement therapies as well as other applications.

16 Claims, 20 Drawing Sheets
(18 of 20 Drawing Sheet(s) Filed in Color)
Specification includes a Sequence Listing.

(51) Int. Cl.
  *B33Y 10/00* (2015.01)
  *B33Y 70/00* (2020.01)
  *B33Y 80/00* (2015.01)
  *C12N 5/077* (2010.01)

(52) U.S. Cl.
  CPC ............ *B33Y 80/00* (2014.12); *C12N 5/0654* (2013.01); *A61L 2430/02* (2013.01); *C12N 2506/1353* (2013.01); *C12N 2513/00* (2013.01); *C12N 2533/50* (2013.01)

(58) Field of Classification Search
  CPC .......... C12N 2506/1353; C12N 5/0654; C12N 2513/00; C12N 2533/50
  See application file for complete search history.

(56) References Cited

U.S. PATENT DOCUMENTS

| | | | |
|---|---|---|---|
| 10,537,828 | B2 | 1/2020 | Baxter et al. |
| 2003/0175410 | A1 | 9/2003 | Campbell et al. |
| 2007/0154552 | A1* | 7/2007 | Siegal ................... A61L 27/383 514/8.4 |
| 2008/0095748 | A1* | 4/2008 | Kharazi ............... C12N 5/0698 424/443 |
| 2011/0008293 | A1 | 1/2011 | Bhandari |
| 2011/0113053 | A1 | 5/2011 | Khan et al. |
| 2013/0023460 | A1 | 1/2013 | Hauser et al. |
| 2014/0012225 | A1 | 1/2014 | Yoo et al. |
| 2014/0349933 | A1 | 11/2014 | Hauser et al. |
| 2015/0038428 | A1 | 2/2015 | Hauser et al. |
| 2016/0136895 | A1 | 5/2016 | Beyer et al. |
| 2016/0288414 | A1 | 10/2016 | Ozbolat et al. |
| 2016/0375177 | A1 | 12/2016 | Hauser et al. |
| 2017/0056548 | A1 | 3/2017 | Lee et al. |
| 2017/0296760 | A1 | 10/2017 | Lee et al. |
| 2018/0030501 | A1 | 2/2018 | Bourdeau et al. |
| 2018/0118978 | A1 | 5/2018 | Yabu et al. |
| 2018/0361025 | A1 | 12/2018 | Lancaster et al. |
| 2019/0219572 | A1 | 7/2019 | Mehra et al. |
| 2019/0321291 | A1 | 10/2019 | Connolly et al. |
| 2020/0148720 | A1 | 5/2020 | Hauser et al. |
| 2020/0199514 | A1 | 6/2020 | Hauser et al. |
| 2020/0247046 | A1 | 8/2020 | Malaquin et al. |
| 2021/0114276 | A1 | 4/2021 | Nelson et al. |
| 2021/0121639 | A1 | 4/2021 | Miri Ramsheh et al. |
| 2022/0054706 | A1 | 2/2022 | Hauser et al. |
| 2022/0371958 | A1 | 11/2022 | Hauser et al. |
| 2023/0295225 | A1 | 9/2023 | Hauser et al. |
| 2023/0405177 | A1 | 12/2023 | Hauser et al. |

FOREIGN PATENT DOCUMENTS

| | | | |
|---|---|---|---|
| CN | 109224654 | A | 1/2019 |
| CN | 111172100 | A | 5/2020 |
| EP | 0 723 646 | B1 | 7/1996 |
| JP | 2005-028216 | A | 2/2005 |
| JP | 2013 009598 | A | 1/2013 |
| JP | 2015-13850 | A | 1/2015 |
| JP | 2016-79190 | A | 5/2016 |
| JP | 2016-530874 | A | 10/2016 |
| JP | 2017-501136 | A | 1/2017 |
| JP | 2020-519605 | A | 7/2020 |
| JP | 2002-320815 | A | 11/2020 |
| KR | 10-1596014 | B1 | 2/2016 |
| KR | 2016 0091993 | A | 8/2016 |
| KR | 10-2020-0007537 | A | 1/2020 |
| KR | 10-2021-0104339 | A | 8/2021 |
| WO | 2007/102735 | A1 | 9/2007 |
| WO | 2008/057608 | A1 | 5/2008 |
| WO | 2008/057608 | A2 | 5/2008 |
| WO | 2014/104981 | A1 | 7/2014 |
| WO | 2014/186581 | A1 | 11/2014 |
| WO | 2014/197999 | A1 | 12/2014 |
| WO | 2015/066705 | A1 | 5/2015 |
| WO | 2015/080670 | A9 | 6/2015 |
| WO | 2015/080671 | A1 | 6/2015 |
| WO | 2016/123693 | A1 | 8/2016 |
| WO | 2016/144259 | A1 | 9/2016 |
| WO | 2017/089963 | A1 | 6/2017 |
| WO | 2018/020737 | A1 | 2/2018 |
| WO | 2018/207037 | A1 | 11/2018 |
| WO | WO-2018207036 | A1 * | 11/2018 ............... A61K 8/64 |
| WO | 2020/162835 | A1 | 8/2020 |

OTHER PUBLICATIONS

Written Opinion received in Singapore Application No. 10202112455P dated Jul. 11, 2023.

Office Action received in Japanese Application No. 2019-561848 dated May 22, 2023.

Notice of Final Rejection received in Korean Application No. 10-2019-7036272 dated May 25, 2023.

European Search Report received in European Application No. 23159765.9 dated Jun. 22, 2023.

Ali et al., "A Non-Canonical NRPS Is Involved in the Synthesis of Fungisporin and Related Hydrophobic Cyclic Tetrapeptides in Penicillium chrysogenum", PLOS ONE; vol. 9, Issue 6, e98212 (2014).

Pubchem CID: 93078 "L-Aspartyl-L_phenylalanine" (2005).

Vasco et al., "Macrocyclization of Peptide Side Chains by the Ugi Reaction: Achieving Peptide Folding and Exocyclic N-Functionalization in One Shot", The Journal of Organic Chemistry, 80, pp. 6697-6707 (2015).

Huebsch, N.; Arany, P. R.; Mao, A. S.; Shvartsman, D.; Ali, O. A.; Bencherif, S. A.; Rivera-Feliciano, J.; Mooney, D. J. Harnessing traction-mediated manipulation of the cell/matrix interface to control stem-cell fate. Nat. Mater. 2010, 9, 518.

Kabiri, K.; Omidian, H.; Hashemi, S.; Zohuriaan-Mehr, M. Synthesis of fast-swelling superabsorbent hydrogels: effect of crosslinker type and concentration on porosity and absorption rate. Eur. Polym. J. 2003, 39, 1341-1348.

Hale, B. W.; Goodrich, L. R.; Frisbie, D. D.; Mollwraith, C. W.; Kisiday, J. D. Effect of scaffold dilution on migration of mesenchymal stem cells from fibrin hydrogels. Am. J. Vet. Res. 2012, 73, 313-318.

Cuchiara, M. P.; Allen, A. C.; Chen, T. M.; Miller, J. S.; West, J. L. Multilayer microfluidic PEGDA hydrogels. Biomaterials 2010, 31, 5491-5497.

Cheng, R.; Yan, Y.; Liu, H.; Chen, H.; Pan, G.; Deng, L.; Cui, W. Mechanically enhanced lipo-hydrogel with controlled release of multi-type drugs for bone regeneration. Appl. Mater. Today 2018, 12, 294-308.

Engler, A. J.; Sen, S.; Sweeney, H. L.; Discher, D. E. Matrix elasticity directs stem cell lineage specification. Cell 2006, 126, 677-689.

Sivaraj, K. K.; Adams, R. H. Blood vessel formation and function in bone. Development 2016, 143, 2706-2715.

Kim, S.; Cha, C. Enhanced mechanical and electrical properties of heteroscaled hydrogels infused with aqueous-dispersible hybrid nanofibers. Biofabrication 2020, 12, No. 015020.

Hwang, T. L.; Shaka, A. J., Water Suppression That Works. Excitation Sculpting Using Arbitrary Wave-Forms and Pulsed-Field Gradients. J. Magn. Reson. 1995, 112, (2), 275-279.

Derome, A. E.; Williamson, M. P., Rapid-Pulsing Artifacts in Double-Quantum-Filtered COSY. J. Magn. Reson. 1990, 88, (1), 177-185.

Piotto, M.; Saudek, V.; Sklenář, V., Gradient-Tailored Excitation for Single-Quantum NMR Spectroscopy of Aqueous Solutions. J. Biomol. NMR 1992, 2, (6), 661-665.

Sklenar, V.; Piotto, M.; Leppik, R.; Saudek, V., Gradient-Tailored Water Suppression for 1H-15N HSQC Experiments Optimized to Retain Full Sensitivity. J. Magn. Reson. 1993, 102, (2), 241-245.

Gilbert, D. F.; Erdmann, G.; Zhang, X.; Fritzsche, A.; Demir, K.; Jaedicke, A.; Muehlenberg, K.; Wanker, E. E.; Boutros, M., A novel multiplex cell viability assay for high-throughput RNAi screening. PloS One 2011, 6, (12), e28338.

(56) References Cited

OTHER PUBLICATIONS

Alshehri et al., Scaffolds from Self-Assembling Tetrapeptides Support 3D Spreading, Osteogenic Differentiation, and Angiogenesis of Mesenchymal Stem Cells; Biomacromolecules; vol. 22; pp. 2094-2106 (2021).
Arab, "Novel Nanofibrous Peptide Scaffolds for Tissue Regeneration", Dissertation, King Abdullah University of Science and Technology, Thuwal, Saudi Arabia, Apr. 2019.
Ikeno et al., "Effects of self-assembling peptide hydrogel scaffold on bone regeneration with recombinant human bone morphogenetic protein-2"; The International Journal of Oral and Maxillofacial Implants; vol. 28, No. 5, pp. e283-289 (2013).
Liu et al., "Stiffness-mediated mesenchymal stem cell fate decision in 3D-bioprinted hydrogels"; Burns & Trauma, vol. 8, pp. 1-13 (2020).
International Search Report and Written Opinion received in International Application No. PCT/IB2021/057623 mailed Dec. 13, 2021.
Official Action received in Japanese Application No. 2019-561848 dated Feb. 28, 2023.
Decision of Dismissal of Amendment received in Japanese Application No. 2019-561747 mailed Apr. 18, 2023.
Examination Report received in Saudi Arabian Application No. 519410522 dated Aug. 2, 2022.
Search Report and Written Opinion received in PCT Application No. PCT/IB2022/051913 mailed Jun. 14, 2022.
Office Action received in U.S. Appl. No. 16/612,580 dated Jun. 6, 2022.
Bowie et al., "Deciphering the Message in Protein Sequences: Toldernace to Amino Acid Substitutions", Science, vol. 249, pp. 1306-1310 (1990).
Burgess et al., "Possible dissociation of the heparin-binding and mitogenic activities of heparin-binding (acidic fibroblast) growth factor-1 from its receptor-binding activities by site-directed mutagenesis of a single lysine residue", J. cell Biol, vol. 111, pp. 2129-2138 (1990).
Loo et al., "Peptide Bioink: Self-Assembling Nanofibrous Scaffolds for Three-Dimensional Organotypic Cultures", vol. 15, pp. 1-13, XP055486589 (2015).
Office Action received in U.S. Appl. No. 17/401,800 mailed Apr. 11, 2022.
Gauthaman, K.; Venugopal, J. R.; Yee, F. C.; Biswas, A.; Ramakrishna, S.; Bongso, A. Osteogenic differentiation of human Wharton's jelly stem cells on nanofibrous substrates in vitro. Tissue Eng., Part A 2011, 17, 71-81.
Leng, Q.; Chen, L.; Lv, Y. RNA-based scaffolds for bone regeneration: application and mechanisms of mRNA, miRNA and siRNA. Theranostics 2020, 10, 3190.
Erdem, A.; Darabi, M. A.; Nasiri, R.; Sangabathuni, S.; Ertas, Y. N.; Alem, H.; Hosseini, V.; Shamloo, A.; Nasr, A. S.; Ahadian, S. 3D Bioprinting of Oxygenated Cell-Laden Gelatin Methacryloyl Constructs. Adv. Healthcare Mater. 2020, 9, No. 1901794.
Myeroff, C.; Archdeacon, M. Autogenous bone graft: donor sites and techniques. J. Bone Jt. Surg. 2011, 93, 2227-2236.
Silbernagel, N.; Körner, A.; Balitzki, J.; Jaggy, M.; Bertels, S.; Richter, B.; Hippler, M.; Hellwig, A.; Hecker, M.; Bastmeyer, M.; Ullrich, N. D. Shaping the Heart: Structural and Functional Maturation of iPSC-Cardiomyocytes in 3D-Micro-Scaffolds. Biomaterials 2020, 227, No. 119551.
Silber, J. S.; Anderson, D. G.; Daffner, S. D.; Brislin, B. T.; Leland, J. M.; Hilibrand, A. S.; Vaccaro, A. R.; Albert, T. J. Donor site morbidity after anterior iliac crest bone harvest for single-level anterior cervical discectomy and fusion. Spine 2003, 28, 134-139.
Alonzo, M.; Alvarez Primo, F.; Anil Kumar, S.; Mudloff, J. A.; Dominguez, E.; Fregoso, G.; Ortiz, N.; Weiss, W. M.; Joddar, B. Bone tissue engineering techniques, advances, and scaffolds for treatment of bone defects. Curr. Opin. Biomed. Eng. 2021, 17, No. 100248.

Amini, A. R.; Laurencin, C. T.; Nukavarapu, S. P. Bone tissue engineering: recent advances and challenges. Crit. Rev. Biomed. Eng. 2012, 40, 363-408.
Bharadwaz, A.; Jayasuriya, A. C. Recent trends in the application of widely used natural and synthetic polymer nanocomposites in bone tissue regeneration. Mater. Sci. Eng., C 2020, 110, No. 110698.
Pittenger, M. F.; Mackay, A. M.; Beck, S. C.; Jaiswal, R. K.; Douglas, R.; Mosca, J. D.; Moorman, M. A.; Simonetti, D. W.; Craig, S.; Marshak, D. R. Multilineage potential of adult human mesenchymal stem cells. Science 1999, 284, 143-147.
Ma, K.; Laco, F.; Ramakrishna, S.; Liao, S.; Chan, C. K. Differentiation of bone marrow-derived mesenchymal stem cells into multi-layered epidermis-like cells in 3D organotypic coculture. Biomaterials 2009, 30, 3251-3258.
Petite, H.; Viateau, V.; Bensaid, W.; Meunier, A.; de Pollak, C.; Bourguignon, M.; Oudina, K.; Sedel, L.; Guillemin, G. Tissue-engineered bone regeneration. Nat. Biotechnol. 2000, 18, 959.
Takamine, Y.; Tsuchiya, H.; Kitakoji, T.; Kurita, K.; Ono, Y.; Ohshima, Y.; Kitoh, H.; Ishiguro, N.; Iwata, H. Distraction osteogenesis enhanced by osteoblastlike cells and collagen gel. Clin. Orthop. Relat. Res. 2002, 399, 240-246.
Kofidis, T.; Lebl, D. R.; Martinez, E. C.; Hoyt, G.; Tanaka, M.; Robbins, R. C. Novel injectable bioartificial tissue facilitates targeted, less invasive, large-scale tissue restoration on the beating heart after myocardial injury. Circulation 2005, 112, 1-173-1-177.
Yildirim, Y.; Naito, H.; Didié, M.; Karikkineth, B. C.; Biermann, D.; Eschenhagen, T.; Zimmermann, W.-H. Development of a biological ventricular assist device: preliminary data from a small animal model. Circulation 2007, 116, I-16-I-23.
Radisic, M.; Park, H.; Shing, H.; Consi, T.; Schoen, F. J.; Langer, R.; Freed, L. E.; Vunjak-Novakovic, G. Functional assembly of engineered myocardium by electrical stimulation of cardiac myocytes cultured on scaffolds. Proc. Natl. Acad. Sci. U.S.A. 2004, 101, 18129-18134.
Spadaccio, C.; Chachques, E.; Chello, M.; Covino, E.; Chachques, J. C.; Genovese, J. Predifferentiated adult stem cells and matrices for cardiac cell therapy. Asian Cardiovasc. Thorac. Ann. 2010, 18, 79-87.
Kutschka, I.; Chen, I. Y.; Kofidis, T.; Arai, T.; Von Degenfeld, G.; Sheikh, A. Y.; Hendry, S. L.; Pearl, J.; Hoyt, G.; Sista, R.; et al. Collagen matrices enhance survival of transplanted cardiomyoblasts and contribute to functional improvement of ischemic rat hearts. Circulation 2006, 114, I-167-I-173.
Orkin, R.; Gehron, P.; Mcgoodwin, E. B.; Martin, G.; Valentine, T.; Swarm, R. A murine tumor producing a matrix of basement membrane. J. Exp. Med. 1977, 145, 204-220.
Sethi, T.; Rintoul, R. C.; Moore, S. M.; Mackinnon, A. C.; Salter, D.; Choo, C.; Chilvers, E. R.; Dransfield, I.; Donnelly, S. C.; Strieter, R.; et al. Extracellular matrix proteins protect small cell lung cancer cells against apoptosis: a mechanism for small cell lung cancer growth and drug resistance in vivo. Nat. Med. 1999, 5, 662-668.
Grant, D.; Kibbey, M.; Kinsella, J.; Cid, M.; Kleinman, H. The role of basement membrane in angiogenesis and tumor growth. Pathol., Res. Pract. 1994, 190, 854-863.
Fushimi, H.; Hiratsuka, T.; Okamura, A.; Ono, Y.; Ogura, I.; Nishimura, I. Recombinant collagen polypeptide as a versatile bone graft biomaterial. Commun. Mater. 2020, 1, No. 1.
Kang, P. L.; Huang, H. H.; Chen, T.; Ju, K. C.; Kuo, S. M. Angiogenesis-promoting effect of LIPUS on hADSCs and HUVECs cultured on collagen/hyaluronan scaffolds. Mater. Sci. Eng., C 2019, 102, 22-33.
Blokhuis, T.; Arts, J. C. Bioactive and osteoinductive bone graft substitutes: definitions, facts and myths. Injury 2011, 42, S26-S29.
Barradas, A.; Yuan, H.; van Blitterswijk, C. A.; Habibovic, P. Osteoinductive biomaterials: current knowledge of properties, experimental models and biological mechanisms. Eur. Cells Mater. 2011, 21, 407-429.
Habibovic, P.; de Groot, K. Osteoinductive biomaterials properties and relevance in bone repair. J. Tissue Eng. Regener. Med. 2007, 1, 25-32.
Ramier, J.; Grande, D.; Bouderlique, T.; Stoilova, O.; Manolova, N.; Rashkov, I.; Langlois, V.; Albanese, P.; Renard, E. From design of

(56) References Cited

OTHER PUBLICATIONS bio-based biocomposite electrospun scaffolds to osteogenic differentiation of human mesenchymal stromal cells. J. Mater. Sci. Mater. Med. 2014, 25, 1563-1575.

Adler-Abramovich, L.; Gazit, E. The physical properties of supramolecular peptide assemblies: from building block association to technological applications. Chem. Soc. Rev. 2014, 43, 6881-6893.

Biesalski, M. A.; Knaebel, A.; Tu, R.; Tirrell, M. Cell adhesion on a polymerized peptide-amphiphile monolayer. Biomaterials 2006, 27, 1259-1269.

Mata, A.; Hsu, L.; Capito, R.; Aparicio, C.; Henrikson, K.; Stupp, S. I. Micropatterning of bioactive self-assembling gels. Soft Matter 2009, 5, 1228-1236.

Eren, E. D.; Tansik, G.; Tekinay, A. B.; Guler, M. O. Mineralized peptide nanofiber gels for enhanced osteogenic differentiation. ChemNanoMat 2018, 4, 837-845.

Mata, A.; Geng, Y.; Henrikson, K. J.; Aparicio, C.; Stock, S. R.; Satcher, R. L.; Stupp, S. I. Bone regeneration mediated by biomimetic mineralization of a nanofiber matrix. Biomaterials 2010, 31, 6004-6012.

Derkus, B.; Okesola, B. O.; Barrett, D. W.; D'Este, M.; Chowdhury, T. T.; Eglin, D.; Mata, A. Multicomponent hydrogels for the formation of vascularized bone-like constructs in vitro. Acta Biomater. 2020, 109, 82-94.

Ghosh, M.; Halperin-Sternfeld, M.; Grigoriants, I.; Lee, J.; Nam, K. T.; Adler-Abramovich, L. Arginine-presenting peptide hydrogels decorated with hydroxyapatite as biomimetic scaffolds for bone regeneration. Biomacromolecules 2017, 18, 3541-3550.

Tsutsumi, H.; Kawamura, M.; Mihara, H. Osteoblastic differentiation on hydrogels fabricated from Ca2+-responsive self-assembling peptides functionalized with bioactive peptides. Bioorg. Med. Chem. 2018, 26, 3126-3132.

Zhang, R.; Liu, Y.; Qi, Y.; Zhao, Y.; Nie, G.; Wang, X.; Zheng, S. Self-assembled peptide hydrogel scaffolds with VEGF and BMP-2 Enhanced in vitro angiogenesis and osteogenesis. Oral Dis. 2021, DOI: 10.1111/odi.13785, in press.

Misawa, H.; Kobayashi, N.; Soto-Gutierrez, A.; Chen, Y.; Yoshida, A.; Rivas-Carrillo, J. D.; Navarro-Alvarez, N.; Tanaka, K.; Miki, A.; Takei, J.; et al. PuraMatrix facilitates bone regeneration in bone defects of calvaria in mice. Cell Transplant. 2006, 15, 903-910.

Ikeno, M.; Hibi, H.; Kinoshita, K.; Hattori, H.; Ueda, M. Effects of self-assembling peptide hydrogel scaffold on bone regeneration with recombinant human bone morphogenetic protein-2. Int. J. Oral Maxillofac. Implants 2013, 28, e283-9.

He, B.; Ou, Y.; Chen, S.; Zhao, W.; Zhou, A.; Zhao, J.; Li, H.; Jiang, D.; Zhu, Y. Designer bFGF-incorporated d-form self-assembly peptide nanofiber scaffolds to promote bone repair. Mater. Sci. Eng., C 2017, 74, 451-458.

Tsukamoto, J.; Naruse, K.; Nagai, Y.; Kan, S.; Nakamura, N.; Hata, M.; Omi, M.; Hayashi, T.; Kawai, T.; Matsubara, T. Efficacy of a self-assembling peptide hydrogel, SPG-178-gel, for bone regeneration and three-dimensional osteogenic Induction of dental pulp stem cells. Tissue Eng., Part A 2017, 23, 1394-1402.

Sun, Y.; Li, W.; Wu, X.; Zhang, N.; Zhang, Y.; Ouyang, S.; Song, X.; Fang, X.; Seeram, R.; Xue, W.; He, L.; Wu, W. Functional Self-Assembling Peptide Nanofiber Hydrogels Designed for Nerve Degeneration. ACS Appl. Mater. Interfaces 2016, 8, 2348-2359.

Guo, J.; Su, H.; Zeng, Y.; Liang, Y.-X.; Wong, W. M.; Ellis-Behnke, R. G.; So, K.-F.; Wu, W. Reknitting the injured spinal cord by self-assembling peptide nanofiber scaffold. Nanomedicine 2007, 3, 311-321.

Liu, X.; Wang, X.; Wang, X.; Ren, H.; He, J.; Qiao, L.; Cui, F.-Z. Functionalized self-assembling peptide nanofiber hydrogels mimic stem cell niche to control human adipose stem cell behavior in vitro. Acta Biomater. 2013, 9, 6798-6805.

Rauf, S.; Susapto, H. H.; Kahin, K.; Alshehri, S.; Abdelrahman, S.; Lam, J. H.; Asad, S.; Jadhav, S.; Sundaramurthi, D.; Gao, X.; Hauser, C. A. E. Self-assembling tetrameric peptides allow in situ 3D bioprinting under physiological conditions. J. Mater. Chem. B 2021, 9, 1069-1081.

Susapto, H. H.; Alhattab, D.; Abdelrahman, S.; Khan, Z.; Alshehri, S.; Kahin, K.; Ge, R.; Moretti, M.; Emwas, A.-H.; Hauser, C. A. E. Ultrashort Peptide Bioinks Support Automated Printing of Large-Scale Constructs Assuring Long-Term Survival of Printed Tissue Constructs. Nano Lett. 2021, 21, 2719-2729.

Arthur, A.; Zannettino, A.; Gronthos, S. The therapeutic applications of multipotential mesenchymal/stromal stem cells in skeletal tissue repair. J. Cell. Physiol. 2009, 218, 237-245.

Polo-Corrales, L.; Latorre-Esteves, M.; Ramirez-Vick, J. E. Scaffold design for bone regeneration. J. Nanosci. Nanotechnol. 2014, 14, 15-56.

Holmes, T. C. Novel peptide-based biomaterial scaffolds for tissue engineering. Trends Biotechnol. 2002, 20, 16-21.

Hauser, C. A.; Deng, R.; Mishra, A.; Loo, Y.; Khoe, U.; Zhuang, F.; Cheong, D. W.; Accardo, A.; Sullivan, M. B.; Riekel, C.; Ying, J. Y.; Hauser, U. A. Natural tri- to hexapeptides self-assemble in water to amyloid beta-type fiber aggregates by unexpected alpha-helical intermediate structures. Proc. Natl. Acad. Sci. U.S.A. 2011, 108, 1361-1366.

Lei, Y.; Gojgini, S.; Lam, J.; Segura, T. The spreading, migration and proliferation of mouse mesenchymal stem cells cultured inside hyaluronic acid hydrogels. Biomaterials 2011, 32, 39-47.

Li, Z.; Huang, S.; Liu, Y.; Yao, B.; Hu, T.; Shi, H.; Xie, J.; Fu, X. Scientific Reports 2018, 8, (1), 8020.

Jorgensen, W. L.; Tirado-Rives, J. Proceedings of the National Academy of Sciences of the United States of America 2005, 102, (19), 6665.

Dodda, L. S.; Cabeza de Vaca, I.; Tirado-Rives, J.; Jorgensen, W. L. Nucleic Acids Research 2017, 45, (W1), W331-W336.

Abraham, M. J.; Murtola, T.; Schulz, R.; Páll, S.; Smith, J. C.; Hess, B.; Lindahl, E. SoftwareX 2015, 1-2, 19-25.

Darden, T.; York, D.; Pedersen, L. The Journal of Chemical Physics 1993, 98, (12), 10089-10092.

Berendsen, H. J. C.; Postma, J. P. M.; Gunsteren, W. F. v.; DiNola, A.; Haak, J. R. The Journal of Chemical Physics 1984, 81, (8), 3684-3690.

Bussi, G.; Donadio, D.; Parrinello, M. The Journal of Chemical Physics 2007, 126, (1), 014101.

Kim, Y. H.; Baek, N. S.; Han, Y. H.; Chung, M.-A.; Jung, S.-D. Journal of neuroscience methods 2011, 202, (1), 38-44.

Riss, T. L.; Valley, M. P.; Zimprich, C. A.; Niles, A. L.; Kupcho, K. R.; Lazar, D. F. 60. Howe, B.; Umrigar, A.; Tsien, F. JoVE (Journal of Visualized Experiments) 2014, (83), e50203.

Howe, B.; Umrigar, A.; Tsien, F. JoVE (Journal of Visualized Experiments) 2014, (83), e50203.

Worton, R. G.; Duff, C., [27] Karyotyping. In Methods in enzymology, Elsevier: 1979; vol. 58, pp. 322-344.

Perrier, A. L.; Tabar, V.; Barberi, T.; Rubio, M. E.; Bruses, J.; Topf, N.; Harrison, N. L.; Studer, L. Proceedings of the National Academy of Sciences 2004, 101, (34), 12543-12548.

Kang, J.; Lee, I. Cardiovascular Pathology 2006, 15, (4), 218-221.

Blakely, B. D.; Bye, C. R.; Fernando, C. V.; Horne, M. K.; Macheda, M. L.; Stacker, S. A.; Arenas, E.; Parish, C. L. PloS one 2011, 6, (3), e18373.

Bowie et al., "Deciphering the Message in Protein Sequences: Tolerance to Amino Acid Substitutions", Science, vol. 47, pp. 1306-1310 (1990).

Burgess et al., "Possible Dissociation of the Heparin-binding Mitogenic Activities of Haparin-binding (Acidic Fibroblast) Growth Factor-1 from Its Receptor-binding Activities by Site-directed Mutagenesis of a Single Lysine Residue", The Journal of Cell Biology, vol. 111, pp. 2129-2138 (1990).

Loo et al, "Peptide Bioink: Printable Nanofibrous Scaffolds for 3D Organotyic Cultures", vol. 15, XP055486589 (2015).

Suspato et al, "Ultrashort Peptide Bioinks Support Automated Printing of Large-Scale Constructs Assuring Long-Term Survival of Printed Tissue Constructs", Nano Lett. 21, 7, pp. 2719-2729 (2021).

International Search Report and Written Opinion received in PCT Application No. PCT/IB2021/057622 mailed Dec. 16, 2021.

(56) References Cited

OTHER PUBLICATIONS

Substantive Examination Report received in Saudi Arabian Application No. 519410522.
Fichman et al., "Self-assembly of short peptides to form hydrogels: Design of building blocks, physical properties and technological applications", Acta Biomaterialia, 16, pp. 1571-1582 (2014).
Office Action received in U.S. Appl. No. 16/612,881 mailed May 20, 2021.
Office Action received in U.S. Appl. No. 16/612,881 mailed Dec. 30, 2020.
Office Action received in Japanese Patent Application No. 2019-561848 mailed Apr. 5, 2022.
Office Action received in Japanese Patent Application No. 2019-561747 mailed Mar. 15, 2022.
Notice of Allowance received in Korean Application No. 10-2019-7036377 dated Apr. 6, 2022.
Search Report and Written Opinion received in PCT Application No. PCT/IB2021/060795.
Ali et al., "A Non-Canonical NRPS Is Involved in the Synthesis of Fungisporin and Related Hydrophobic Cyclic Tetrapeptides in Penicillium chrysogenum", PLOS ONE, vol. 9, Issue 6, pp. 1-10 (2014).
Alrashoudi et al., "Fabrication of a Lateral Flow Assay for Rapid In-Field Detection of COVID-19 Antibodies Using Additive Manufacturing Printing Technologies", International Journal of Bioprinting, vol. 7, Issue 4, pp. 76-84 (2021).
Farrera-Soler et al, "Identification of immunodominant linear epitopes from SARS-CoV-2 patient plasma", PLOS ONE, pp. 1-15 (2020).
Saatci, Newly developed methods for SARS-CoV-2 detection [SARS-CoV-2 saptanmasinda yeni gelistririlen tani yontemleri], Turk J. Biochem., 45 (5), pp. 465-474 (2020).
Vasco et al., "Macrocyclization of Peptide Side Chains by the Ugi Reaction: Achieving Peptide Folding and Exocyclic N-Functionalization in One Shot", Journal of Organic Chemistry, 80, pp. 6697-6707 (2015).
Xiang et al., "A novel double antibody sandwich-lateral flow immunoassay for the rapid and simple detection of hepatitis C virus", International Journal of Molecular Medicine, 30, pp. 1041-1047 (2012).
Examination Report received in European Patent Application No. 18 718 922.0 dated May 20, 2022.
Gungor-Ozkerim, P. S.; Inci, I.; Zhang, Y. S.; Khademhosseini, A.; Dokmeci, M. R. Biomaterials Science 2018, 6, (5), 915-946.
Donderwinkel, I.; van Hest, J. C. M.; Cameron, N. R. Polymer Chemistry 2017, 8, (31), 4451-4471.
Gopinathan, J.; Noh, I. Biomater Res 2018, 22, 11-11.
Khademhosseini, A.; Camci-Unal, G., 3D Bioprinting in Regenerative Engineering:: Principles and Applications. CRC Press: 2018.
Gjorevski, N.; Sachs, N.; Manfrin, A.; Giger, S.; Bragina, M. E.; Ordonez-Moran, P.; Clevers, H.; Lutolf, M. P. Nature 2016, 539, (7630), 560-564.
Hauser, C. A. E.; Deng, R.; Mishra, A.; Loo, Y.; Khoe, U.; Zhuang, F.; Cheong, D. W.; Accardo, A.; Sullivan, M. B.; Riekel, C.; Ying, J. Y.; Hauser, U. A. Proceedings of the National Academy of Sciences 2011, 108, (4), 1361-1366.
Loo, Y.; Lakshmanan, A.; Ni, M.; Toh, L. L.; Wang, S.; Hauser, C. A. E. Nano Letters 2015, 15, (10), 6919-6925.
Seow, W. Y.; Salgado, G.; Lane, E. B.; Hauser, C. A. E. Scientific Reports 2016, 6, 32670.
Chan, K. H.; Xue, B.; Robinson, R. C.; Hauser, C. A. E. Scientific Reports 2017, 7, (1), 12897.
Wang, H.; Ren, C.; Song, Z.; Wang, L.; Chen, X.; Yang, Z. Nanotechnology 2010, 21, (22), 225606.
Raeburn, J.; Pont, G.; Chen, L.; Cesbron, Y.; Lévy, R.; Adams, D. J. Soft Matter 2012, 8, (4), 1168-1174.
Betush, R. J.; Urban, J. M.; Nilsson, B. L. Peptide Science 2018, 110, (1), e23099.
Lakshmanan, A.; Cheong, D. W.; Accardo, A.; Di Fabrizio, E.; Riekel, C.; Hauser, C. A. Proc Natl Acad Sci U S A 2013, 110, (2), 519-24.
Bowerman, C. J.; Ryan, D. M.; Nissan, D. A.; Nilsson, B. L. Molecular BioSystems 2009, 5, (9), 1058-1069.
Senguen, F. T.; Lee, N. R.; Gu, X.; Ryan, D. M.; Doran, T. M.; Anderson, E. A.; Nilsson, B. L. Molecular BioSystems 2011, 7, (2), 486-496.
Surewicz, W. K.; Mantsch, H. H.; Chapman, D. Biochemistry 1993, 32, (2), 389-394.
Goormaghtigh, E.; Cabiaux, V.; Ruysschaert, J.-M. European Journal of Biochemistry 1990, 193, (2), 409-420.
Williams, R. W.; Dunker, A. K. Journal of Molecular Biology 1981, 152, (4), 783-813.
Rivas-Arancibia, S.; Rodriguez-Martinez, E.; Badillo-Ramírez, I.; López-González, U.; Saniger, J. M. Frontiers in Molecular Neuroscience 2017, 10, (137).
Seow, W. Y.; Salgado, G.; Lane, E. B.; Hauser, C. A. E. Scientific Reports 2016, 6.
Tuncaboylu, D. C.; Argun, A.; Sahin, M.; Sari, M.; Okay, O. Polymer 2012, 53, (24), 5513-5522.
Murphy, S. V.; Atala, A. Nature Biotechnology 2014, 32, (8), 773-785.
Grinnell, F. Trends in cell biology 2003, 13, (5), 264-269.
Franco-Barraza, J.; Beacham, D. A.; Amatangelo, M. D.; Cukierman, E. Current protocols in cell biology 2016, 71, (1), 10.9. 1-10.9.34.
Seliktar, D. Science 2012, 336, (6085), 1124-1128.
Baker, B. M.; Chen, C. S. Journal of cell science 2012, 125, (13), 3015-3024.
Even-Ram, S.; Yamada, K. M. Current opinion in cell biology 2005, 17, (5), 524-532.
Lutolf, M. P.; Lauer-Fields, J. L.; Schmoekel, H. G.; Metters, A. T.; Weber, F. E.; Fields, G. B.; Hubbell, J. A. Proceedings of the National Academy of Sciences 2003, 100, (9), 5413-5418.
Mazzeo, M. S.; Chai, T.; Daviran, M.; Schultz, K. M. ACS applied bio materials 2018, 2, (1), 81-92.
Discher, D. E.; Mooney, D. J.; Zandstra, P. W. Science 2009, 324, (5935), 1673-1677.
Engler, A. J.; Sen, S.; Sweeney, H. L.; Discher, D. E. Cell 2006, 126, (4), 677-689.
Chaudhuri, O.; Gu, L.; Klumpers, D.; Darnell, M.; Bencherif, S. A.; Weaver, J. C.; Huebsch, N.; Lee, H.-p.; Lippens, E.; Duda, G. N. Nature materials 2016, 15, (3), 326-334.
Dalby, M. J.; Gadegaard, N.; Tare, R.; Andar, A.; Riehle, M. O.; Herzyk, P.; Wilkinson, C. D.; Oreffo, R. O. Nature materials 2007, 6, (12), 997-1003.
Haugh, M. G.; Vaughan, T. J.; Madl, C. M.; Raftery, R. M.; McNamara, L. M.; O'Brien, F. J.; Heilshorn, S. C. Biomaterials 2018, 171, 23-33.
Silbernagel, N.; Körner, A.; Balitzki, J.; Jaggy, M.; Bertels, S.; Richter, B.; Hippler, M.; Hellwig, A.; Hecker, M.; Bastmeyer, M. Biomaterials 2020, 227, 119551.
Darnell, M.; Gu, L.; Mooney, D. Biomaterials 2018, 181, 182-188.
Kahin, K.; Khan, Z.; Albagami, M.; Usman, S.; Bahnshal, S.; Alwazani, H.; Majid, M.; Rauf, S.; Hauser, C. In Development of a robotic 3D bioprinting and microfluidic pumping system for tissue and organ engineering, Microfluidics, BioMEMS, and Medical Microsystems XVII, 2019; International Society for Optics and Photonics: p. 108750Q.
Mouser, V. H. M.; Melchels, F. P. W.; Visser, J.; Dhert, W. J. A.; Gawlitta, D.; Malda, J. Biofabrication 2016, 8, (3), 035003.
Chimene, D.; Peak, C. W.; Gentry, J. L.; Carrow, J. K.; Cross, L. M.; Mondragon, E.; Cardoso, G. B.; Kaunas, R.; Gaharwar, A. K. ACS Applied Materials & Interfaces 2018, 10, (12), 9957-9968.
Bertassoni, L. E.; Cardoso, J. C.; Manoharan, V.; Cristino, A. L.; Bhise, N. S.; Araujo, W. A.; Zorlutuna, P.; Vrana, N. E.; Ghaemmaghami, A. M.; Dokmeci, M. R. Biofabrication 2014, 6, (2), 024105.
Markstedt, K.; Mantas, A.; Tournier, I.; Martínez Ávila, H. c.; Hagg, D.; Gatenholm, P. Biomacromolecules 2015, 16, (5), 1489-1496.
Wilson, S. A.; Cross, L. M.; Peak, C. W.; Gaharwar, A. K. ACS applied materials & interfaces 2017, 9, (50), 43449-43458.
Bernal, P. N.; Delrot, P.; Loterie, D.; Li, Y.; Malda, J.; Moser, C.; Levato, R. Advanced materials 2019, 31, (42), 1904209.

(56) References Cited

OTHER PUBLICATIONS

Kang, H.-W.; Lee, S. J.; Ko, I. K.; Kengla, C.; Yoo, J. J.; Atala, A. Nature biotechnology 2016, 34, (3), 312.
Hwang, T. L.; Shaka, A. J. Journal of Magnetic Resonance, Series A 1995, 112, (2), 275-279. 46. Derome, A. E.; Williamson, M. P. Journal of Magnetic Resonance (1969) 1990, 88, (1), 177-185.
Piotto, M.; Saudek, V.; Sklenář, V. Journal of Biomolecular NMR 1992, 2, (6), 661-665. 48. Sklenar, V.; Piotto, M.; Leppik, R.; Saudek, V. Journal of Magnetic Resonance, Series A 1993, 102, (2), 241-245.
Derome, A. E.; Williamson, M. P. Journal of Magnetic Resonance (1969) 1990, 88, (1), 177-185.
Sklenar, V.; Piotto, M.; Leppik, R.; Saudek, V. Journal of Magnetic Resonance, Series A 1993, 102, (2), 241-245.
Micsonai, A.; Wien, F.; Kernya, L.; Lee, Y.-H.; Goto, Y.; Réfrégiers, M.; Kardos, J. Proceedings of the National Academy of Sciences 2015, 112, (24), E3095.
Maiti, N. C.; Apetri, M. M.; Zagorski, M. G.; Carey, P. R.; Anderson, V. E. Journal of the American Chemical Society 2004, 126, (8), 2399-2408.
Final Official Action received in Japanese Application No. 2019-561848 dated Oct. 11, 2022.
Examination Report received in European Application No. 18 720 665.1 dated Oct. 25, 2022.
Official Action received in Japanese Application No. 2019-561747 dated Sep. 13, 2022.
Examination Report received in Saudi Arabian Application No. 521430991 dated Aug. 18, 2022.
Office Action received in U.S. Appl. No. 16/612,580 dated Sep. 21, 2022.
Office Action received in U.S. Appl. No. 17/401,800 dated Aug. 30, 2022.
International Search Report and Written Opinion received in International Application No. PCT/IB2022/055194 dated Sep. 20, 2022.
International Search Report and Written Opinion received in International Application No. PCT/IB2022/055054 dated Sep. 26, 2022.
Chen et al., "Hydrogelation of the Short Self-Assembling Peptide I3QGK Regulated by Transglutaminase and Use for Rapid Hemostasis", ACS Appl Matter Interfaces, vol. 28, pp. 17833-17841 (2016).
Echalier et al., "Modular bioink for 3D printing of biocompatible hydrogels: sol-gel polymerization of hybrid peptides and polymers", RSC Advances, vol. 7, pp. 12231-12235 (2017).
Holzl et al., "Bioink properties before, during and after 3D printing", Biofabrication, vol. 8, 032002 (2016).
Holz et al., "High-Power 365 nm UV LED Mercury Arc Lamp Replacement for Photochemistry and Chemical Photolithography", ACS Sustainable Chemistry & Engineering, vol. 5, pp. 828-834 (2017).
Lim et al., "New Visible-Light Photoinitiating System for Improved Print Fidelity in Gelatin-Based Bioinks", ACS Biomaterials Science and Engineering, vol. 2, pp. 1752-1762 (2016).
Loo et al., "Bioprinting synthetic self-assembling peptide hydrogels for boimedical applications", Biomedical Materials, vol. 11, No. 1 (2015).
Sekine et al., "Capillary Networks for Bio-Artificial Three-Dimensional Tissues Fabricated Using Cell Sheet Based Tissue Engineering", International Journal of Molecular Sciences, vol. 22, No. 92, pp. 1-12 (2021).
Susapto et al., "Ultrashort Peptide Bioinks Support Automated Printing of Large-Scale Constructs Assuring Long-Term Survival of Printed Tissue Constructs", Nano Letters, vol. 21, pp. 2719-2729 (2021).
Yan et al., "Advances in portable electrospinning devices for in situ delivery of personalized wound care", Nanoscale, vol. 11, pp. 19166-19178 (2019).
Office Action received in Korean Application No. 10-2019-7036272 mailed Oct. 21, 2022.
Zhang et al., "Catechol functionalized hyperbranched polymers as biomedical materials", Polymers in Polymer Science, vol. 78, pp. 47-55 (2018).
Examination Report received in Saudi Arabian Application No. 523442624 mailed Sep. 28, 2023.
International Search Report and Written Opinion received in PCT Application No. PCT/IB2023/056328 mailed Oct. 13, 2023.
International Search Report and Written Opinion received in PCT Application No. PCT/IB2018/052173 mailed Sep. 9, 2018.
International Search Report and Written Opinion received in PCT Application No. PCT/IB2018/052189 mailed Aug. 28, 2018.
Office Action received in Saudi Arabian Application No. 519410522.
Office Action received in Korean Application No. 10-2019-7036277 mailed Sep. 29, 2021.
Office Action received in Saudi Arabian Application No. 519410521.
Loo et al., "Peptide Biolink: Self-Assembling Nanofibrous Scaffolds for Three-Dimensional Organotypic Cultures", Nano Letters, vol. 15, pp. 6919-6925 (2015).
Bowie et al., "Deciphering the Message in Protein Sequences: Tolerance of Amino Acid Substitutions", Science, vol. 247, pp. 1306-1310 (1990).
Burgess et al., "Possible Dissociation of the Heparin-binding Mitogenic Activities of Heparin-binding (Acid Fibroblast) Growth Factor-1 from Its Receptor-binding Activities by Site-directed Mutagenesis of a Single Lysine Residue", The Journal of Cell Biology, vol. 111, pp. 2129-2138 (1990).
Loo et al., "Peptide Bioink: Printable Nanofibrous Scaffolds for 3D Organotypic Cultures", vol. 15, XP055486589 (2015).
Fichman et al., "Self-assembly of short peptides to form hydrogels: Design of building blocks, physical properties and technological applications", Acta Biomaterials, vol. 10, pp. 1671-1682 (2014).
International Search Report and Written Opinion received in PCT Application No. PCT/IB2021/057625 mailed Dec. 14, 2021.
International Search Report and Written Opinion received in PCT Application No. PCT/IB2021/057624 mailed Dec. 13, 2021.
International Search Report and Written Opinion received in PCT Application No. PCT/IB2021/057623 mailed Dec. 13, 2021.
International Search Report and Written Opinion received in PCT Application No. PCT/IB2021/057996 mailed Dec. 20, 2021.
International Search Report and Written Opinion received in PCT Application No. PCT/IB2021/057973 mailed Dec. 20, 2021.
International Search Report and Written Opinion received in PCT Application No. PCT/IB2021/059652 mailed Feb. 3, 2022.
Cembran et al., "Biomimetic Materials and Their Utility in Modeling the 3-Dimensional Neural Environment", iScience, vol. 23, pp. 1-16 (2020).
Cunha et al., "3D Culture of adult mouse neural stem cells within functionalized self-assembling peptide scaffolds", International Journal of Nanomedicine, vol. 6, pp. 943-955 (2011).
Marchini et al., "Multi-Functionalized Self-Assembling Peptides as Reproducible 3D Cell Culture Systems Enabling Differentiation and Survival of Various Human Neural Stem Cell Lines", frontiers in Neuroscience, vol. 14, Article 413, pp. 1-11 (2020).
Ranjan et al., "A microfiber scaffold-based 3D in vitro human neuronal culture model of Alzheimer's disease", The Royal Society of Chemistry, vol. 8, pp. 4861-4874 (2020).
Zhang et al., "Compatability of neural stem cells with functionalized self-assembling peptide scaffold in vitro", Biotechnology and Bioprocess Engineering, vol. 15, pp. 545-551 (2010).
Arab, "Novel Nanofibrous Peptide Scaffolds for Tissue Regeneration", PhD Thesis, Kind Abdullah University of Science and Technology, pp. 1-131 (2019).
Ikeno et al., "Effects of self-assembling peptide hydrogel scaffold on bone regeneration with recombinant human bone morphogenetic protein-2", The International Journal of Oral and Maxillofacial Implants, vol. 28, No. 5, pp. 283-289 (2013).
Liu et al., "Stiffness-mediated mesenchymal stem cell fate decision in 3D-bioprinted hydrogels", Burns and Trauma, vol. 8, pp. 1-13 (2020).
Sundararajan et al., "Use of cyanobacterial gas vesicles as oxygen carriers in cell culture", Cytotechnology, vol. 52, pp. 139-149 (2006).
Upadhyay et al., "Understanding Gas Vesicles and Its Scope in Biotechnological Applications", Advances in Biotechnology and Microbiology, vol. 11, Issue 2, pp. 1-13 (2018).

(56) References Cited

OTHER PUBLICATIONS

Loo, Y.; Chan, Y. S.; Szczerbinska, I.; Tan, B. C.; Wan, A. C.; Ng, H. H.; Hauser, C. A. A Chemically Well-Defined, Self-Assembling 3D Substrate for Long-Term Culture of Human Pluripotent Stem Cells. ACS Appl. Bio Mater. 2019, 2, 1406-1412.
Lee, J. H.; Jung, H. W.; Kang, I.-K.; Lee, H. B. Cell behaviour on polymer surfaces with different functional groups. Biomaterials 1994, 15, 705-711.
Guo, S.; Zhu, X.; Li, M.; Shi, L.; Ong, J. L. T.; Jańczewski,D.; Neoh, K. G. Parallel Control over Surface Charge and Wettability Using Polyelectrolyte Architecture: Effect on Protein Adsorption and Cell Adhesion. ACS Appl. Mater. Interfaces 2016, 8, 30552-30563.
Hauser, C. A. E.; Zhang, S. Designer self-assembling peptide nanofiber biological materials. Chem. Soc. Rev. 2010, 39, 2780-2790.
Bowerman, C. J.; Ryan, D. M.; Nissan, D. A.; Nilsson, B. L. The Effect of Increasing Hydrophobicity on the Self-Assembly of Amphipathic β-Sheet Peptides. Mol. Biosyst. 2009, 5, 1058-1069.
Susapto, H. H.; Alhattab, D.; Abdelrahman, S.; Khan, Z.; Alshehri, S.; Kahin, K.; Ge, R.; Moretti, M.; Emwas, A. H.; Hauser, C. A. E. Ultrashort Peptide Bioinks Support Automated Printing of Large-Scale Constructs Assuring Long-Term Survival of Printed Tissue Constructs. Nano Lett. 2021, 2719.
Friedrichs, J.; Taubenberger, A.; Franz, C. M.; Muller, D. J. Cellular Remodelling of Individual Collagen Fibrils Visualized by Time-lapse AFM. J. Mol. Biol. 2007, 372, 594-607.
Nakayama, M.; Amano, M.; Katsumi, A.; Kaneko, T.; Kawabata, S.; Takefuji, M.; Kaibuchi, K. Rho-kinase and myosin II activities are required for cell type and environment specific migration. Genes Cells 2005, 10, 107-117.
Beadle, C.; Assanah, M. C.; Monzo, P.; Vallee, R.; Rosenfeld, S. S.; Canoll, P. The Role of Myosin II in Glioma Invasion of the Brain. Mol. Biol. Cell 2008, 19, 3357-3368.
Friedl, P.; Wolf, K.; Lammerding, J. Nuclear mechanics during cell migration. Curr. Opin. Cell Biol. 2011, 23, 55-64.
Balzer, E. M.; Tong, Z.; Paul, C. D.; Hung, W.-C.; Stroka, K. M.; Boggs, A. E.; Martin, S. S.; Konstantopoulos, K. Physical confinement alters tumor cell adhesion and migration phenotypes. FASEB J. 2012, 26, 4045-4056.
Khatau, S. B.; Bloom, R. J.; Bajpai, S.; Razafsky, D.; Zang, S.; Giri, A.; Wu, P.-H.; Marchand, J.; Celedon, A.; Hale, C. M.; Sun, S. X.; Hodzic, D.; Wirtz, D. The distinct roles of the nucleus and nucleus-cytoskeleton connections in three-dimensional cell migration. Sci. Rep. 2012, 2, No. 488.
Wen, J. H.; Vincent, L. G.; Fuhrmann, A.; Choi, Y. S.; Hribar, K. C.; Taylor-Weiner, H.; Chen, S.; Engler, A. J. Interplay of matrix stiffness and protein tethering in stem cell differentiation. Nat. Mater. 2014, 13, 979-987.
Thievessen, I.; Thompson, P. M.; Berlemont, S.; Plevock, K. M.; Plotnikov, S. V.; Zemljic-Harpf, A.; Ross, R. S.; Davidson, M. W.; Danuser, G.; Campbell, S. L.; Waterman, C. M. Vinculin-actin interaction couples actin retrograde low to focal adhesions, but is dispensable for focal adhesion growth. J. Cell Biol. 2013, 202, 163-177.
Humphries, J. D.; Wang, P.; Streuli, C.; Geiger, B.; Humphries, M. J.; Ballestrem, C. Vinculin controls focal adhesion formation by direct interactions with talin and actin. J. Cell. Biol. 2007, 179, 1043-1057.
Ode, A.; Schoon, J.; Kurtz, A.; Gaetjen, M.; Ode, J. E.; Geissler, S.; Duda, G. N. CD73/5'-ecto-nucleotidase acts as a regulatory factor in osteo-/chondrogenic differentiation of mechanically stimulated mesenchymal stromal cells. Eur. Cells Mater. 2013, 25, 37-47.
Aslan, H.; Zilberman, Y.; Kandel, L.; Liebergall, M.; Oskouian, R. J.; Gazit, D.; Gazit, Z. Osteogenic differentiation of noncultured immunoisolated bone marrow-derived CD105+ cells. Stem Cells 2006, 24, 1728-1737.
Huang, S.; Ingber, D. E. The structural and mechanical complexity of cell-growth control. Nat. Cell Biol. 1999, 1, No. E131.

McBeath, R.; Pirone, D. M.; Nelson, C. M.; Bhadriraju, K.; Chen, C. S. Cell shape, cytoskeletal tension, and RhoA regulate stem cell lineage commitment. Dev. Cell 2004, 6, 483-495.
Katz, B.-Z.; Zamir, E.; Bershadsky, A.; Kam, Z.; Yamada, K. M.; Geiger, B. Physical state of the extracellular matrix regulates the structure and molecular composition of cell-matrix adhesions. Mol. Biol. Cell 2000, 11, 1047-1060.
Cukierman, E.; Pankov, R.; Stevens, D. R.; Yamada, K. M. Taking cell-matrix adhesions to the third dimension. Science 2001, 294, 1708-1712.
Fischbach, C.; Kong, H. J.; Hsiong, S. X.; Evangelista, M.B.; Yuen, W.; Mooney, D. J. Cancer cell angiogenic capability is regulated by 3D culture and integrin engagement. Proc. Natl. Acad. Sci. U.S.A. 2009, 106, 399-404.
Hsiong, S. X.; Boontheekul, T.; Huebsch, N.; Mooney, D. J. Cyclic arginine-glycine-aspartate peptides enhance three-dimensional stem cell osteogenic differentiation. Tissue Eng., Part A 2009, 15, 263-272.
Park, J. S.; Huang, N. F.; Kurpinski, K. T.; Patel, S.; Hsu, S.; Li, S. Mechanobiology of mesenchymal stem cells and their use in cardiovascular repair. Front. Biosci. 2007, 12, 5098-5116.
Tan, S.; Fang, J. Y.; Yang, Z.; Nimni, M. E.; Han, B. The synergetic effect of hydrogel stiffness and growth factor on osteogenic differentiation. Biomaterials 2014, 35, 5294-5306.
Knight, B.; Laukaitis, C.; Akhtar, N.; Hotchin, N. A.; Edlund, M.; Horwitz, A. R. Visualizing muscle cell migration in situ. Curr. Biol. 2000, 10, 576-585.
Roskelley, C.; Desprez, P.; Bissell, M. Extracellular matrix-dependent tissue-specific gene expression in mammary epithelial cells requires both physical and biochemical signal transduction. Proc. Natl. Acad. Sci. U.S.A. 1994, 91, 12378-12382.
Thievessen, I.; Fakhri, N.; Steinwachs, J.; Kraus, V.; McIsaac, R. S.; Gao, L.; Chen, B.-C.; Baird, M. A.; Davidson, M. W.; Betzig, E.; et al. Vinculin is required for cell polarization, migration, and extracellular matrix remodeling in 3D collagen. FASEB J. 2015, 29, 4555-4567.
Case, L. B.; Baird, M. A.; Shtengel, G.; Campbell, S. L.; Hess, H. F.; Davidson, M. W.; Waterman, C. M. Molecular mechanism of vinculin activation and nanoscale spatial organization in focal adhesions. Nat. Cell Biol. 2015, 17, 880-892.
Carisey, A.; Ballestrem, C. Vinculin, an adapter protein in control of cell adhesion signalling. Eur. J. Cell Biol. 2011, 90, 157-163.
Xu, W.; Baribault, H.; Adamson, E. D. Vinculin knockout results in heart and brain defects during embryonic development. Development 1998, 125, 327-337.
Kumar, G.; Tison, C. K.; Chatterjee, K.; Pine, P. S.; McDaniel, J. H.; Salit, M. L.; Young, M. F.; Simon, C. G., Jr. The determination of stem cell fate by 3D scaffold structures through the control of cell shape. Biomaterials 2011, 32, 9188-9196.
Pablo Rodríguez, J.; González, M.; Ríos, S.; Cambiazo, V. Cytoskeletal organization of human mesenchymal stem cells (MSC) changes during their osteogenic differentiation. J. Cell. Biochem. 2004, 93, 721-731.
Treiser, M. D.; Yang, E. H.; Gordonov, S.; Cohen, D. M.; Androulakis, I. P.; Kohn, J.; Chen, C. S.; Moghe, P. V. Cytoskeleton-based forecasting of stem cell lineage fates. Proc. Natl. Acad. Sci. U.S.A. 2010, 107, 610-615.
Hunter, G. K.; Hauschka, P. V.; Poole, R. A.; Rosenberg, L. C.; Goldberg, H. A. Nucleation and inhibition of hydroxyapatite formation by mineralized tissue proteins. Biochem. J. 1996, 317, 59-64.
Wang, J.; Cui, X.; Zhou, Y.; Xiang, Q. Core-shell PLGA/ collagen nanofibers loaded with recombinant FN/CDHs as bone tissue engineering scaffolds. Connect. Tissue Res. 2014, 55, 292-298.
Khan, S. N.; Lane, J. M. Bone Tissue Engineering: Basic Science and Clinical Concepts. Orthopedic Tissue Engineering; CRC Press, 2004; pp. 177-194.
Oreffo, R. O.; Kusec, V.; Romberg, S.; Triffitt, J. T. Human bone marrow osteoprogenitors express estrogen receptor-alpha and bone morphogenetic proteins 2 and 4 mRNA during osteoblastic differentiation. J. Cell. Biochem. 1999, 75, 382-392.
Frank, O.; Heim, M.; Jakob, M.; Barbero, A.; Schäfer, D.; Bendik, I.; Dick, W.; Heberer, M.; Martin, I. Real-time quantitative RT-PCR

(56) References Cited

OTHER PUBLICATIONS analysis of human bone marrow stromal cells during osteogenic differentiation in vitro. J. Cell. Biochem. 2002, 85, 737-746.

Miron, R.; Zhang, Y. Osteoinduction: a review of old concepts with new standards. J. Dent. Res. 2012, 91, 736-744.

Rittling, S. R.; Matsumoto, H. N.; Mckee, M. D.; Nanci, A.; An, X. R.; Novick, K. E.; Kowalski, A. J.; Noda, M.; Denhardt, D. T. Mice lacking osteopontin show normal development and bone structure but display altered osteoclast formation in vitro. J. Bone Miner. Res. 1998, 13, 1101-1111.

Chellaiah, M. A.; Kizer, N.; Biswas, R.; Alvarez, U.; Strauss-Schoenberger, J.; Rifas, L.; Rittling, S. R.; Denhardt, D. T.; Hruska, K. A. Osteopontin deficiency produces osteoclast dysfunction due to reduced CD44 surface expression. Mol. Biol. Cell 2003, 14, 173-189.

Bax, D. V.; Rodgers, U. R.; Bilek, M. M.; Weiss, A. S. Cell adhesion to tropoelastin is mediated via the C-terminal GRKRK motif and integrin αVβ3. J. Biol. Chem. 2009, 284, 28616-28623.

Taddese, S.; Weiss, A. S.; Jahreis, G.; Neubert, R. H.; Schmelzer, C. E. In vitro degradation of human tropoelastin by MMP-12 and the generation of matrikines from domain 24. Matrix Biol. 2009, 28, 84-91.

Getie, M.; Schmelzer, C.; Neubert, R. Characterization of peptides resulting from digestion of human skin elastin with elastase. Proteins 2005, 61, 649-657.

Phillips, J. E.; Petrie, T. A.; Creighton, F. P.; Garcia, A. J. Human mesenchymal stem cell differentiation on self-assembledmonolayers presenting different surface chemistries. Acta Biomater. 2010, 6, 12-20.

Nemir, S.; West, J. L. Synthetic materials in the study of cell response to substrate rigidity. Ann. Biomed. Eng. 2010, 38, 2-20.

Holst, J.; Watson, S.; Lord, M. S.; Eamegdool, S. S.; Bax, D. V.; Nivison-Smith, L. B.; Kondyurin, A.; Ma, L.; Oberhauser, A. F.; Weiss, A. S.; Rasko, J. E. J. Substrate elasticity provides mechanical signals for the expansion of hemopoietic stem and progenitor cells. Nat. Biotechnol. 2010, 28, 1123.

Rowlands, A. S.; George, P. A.; Cooper-White, J. J. Directing osteogenic and myogenic differentiation of MSCs: interplay of stiffness and adhesive ligand presentation. Am. J. Physiol.: Cell Physiol. 2008, 295, C1037-C1044.

Saha, K.; Keung, A. J.; Irwin, E. F.; Li, Y.; Little, L.; Schaffer, D. V.; Healy, K. E. Substrate modulus directs neural stem cell behavior. Biophys. J. 2008, 95, 4426-4438.

Liu et al., "Stiffness-mediated mesenchymal stem cell fate decision in 3D-bioprinted hydrogels", Burns & Trauma, vol. 8 (2020).

Written Opinion received in Singapore Application No. 1020112455P dated Mar. 27, 2024.

Examination Report received in Saudi Arabian Application No. 523442596 dated Mar. 31, 2024.

Non-Final Office Action received in U.S. Appl. No. 18/021,645 dated Apr. 1, 2024.

Pubchem CID: 97078 "L-Aspartyl-L-phenylalanine".

\* cited by examiner

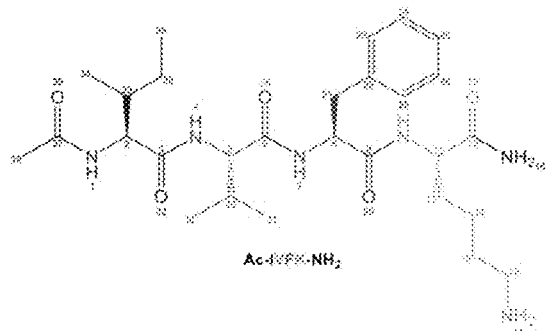

| No | δ (ppm 1H) | Splitting | Amino Acid | Atom | Assignment |
|---|---|---|---|---|---|
| 7 | 8.46 | d, J = 7.1 Hz, 1H | F | NH | $F_{amide}$ |
| 10 | 8.26 | d, J = 7.7 Hz, 1H | K | NH | $K_{amide}$ |
| 4 | 8.13 | d, J = 7.6 Hz, 1H | V | NH | $V_{amide}$ |
| 1 | 8.12 | d, J = 3.6 Hz, 1H | I | NH | $I_{amide}$ |
| 22-27 | 7.32 | m, 5H | F | Aromatic | $F_{aromatic}$ |
| 18 | 6.99 | s, 1H | C-terminal | NH | Amide Capping |
| 18 | 6.86 | s, 1H | C-terminal | NH | Amide Capping |
| 8 | 4.62 | NI | F | CH | $F_\alpha$ |
| 11 | 4.21 | m, 1H | K | CH | $K_\alpha$ |
| 5 | 4.09 | t, J = 14.6 Hz, 1H | V | CH | $V_\alpha$ |
| 2 | 4.07 | t, J = 8.2 Hz, 1H | I | CH | $I_\alpha$ |
| 21 | 3.06 | m, 3H | F | $CH_2$ | $F_\beta$ |
| 16 | 2.96 | t, J = 8.1 Hz, 3H | K | $CH_2$ | $K_\epsilon$ |
| 38 | 2.02 | s, 3H | N-terminal | Acetyl | Acetyl capping |
| 29 | 1.96 | m, 1H | V | CH | $V_\beta$ |
| 13 | 1.77 | m, 2H | K | CH | $K_{\beta1}$ |
| 33 | | | I | CH | $I_\beta$ |
| 13 | 1.64 | m, 3H | K | CH | $K_{\beta2}$ |
| 15 | | | K | $CH_2$ | $K_\delta$ |
| 35 | 1.46 | m, 1H | I | CH | $I_{\gamma1}$ |
| 14 | 1.36 | m, 2H | K | $CH_2$ | $K_\gamma$ |
| 35 | 1.16 | m, 1H | I | CH | $I_{\gamma1}$ |
| 30 | 0.89 | d, J = 6.9 Hz, 3H | V | $CH_3$ | $V_{\gamma1}$ |
| 36 | 0.85 | m, 6H | I | $CH_3$ | $I_\gamma$ |
| 31 | | | V | $CH_3$ | $V_{\gamma2}$ |
| 34 | 0.78 | d, J = 7.0 Hz, 3H | I | $CH_3$ | $I_\delta$ |

FIG. 5

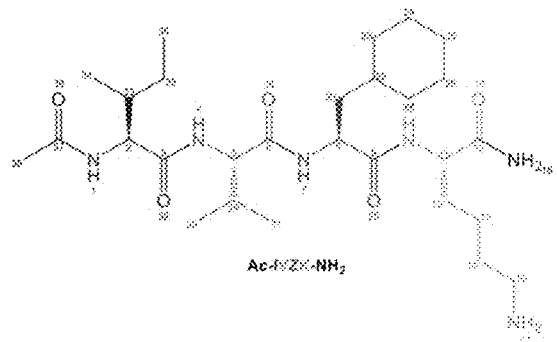

Table S2: 1H-NMR chemical shifts of IVZK

| No | δ (ppm 1H) | Splitting | Amino Acid | Atom | Assignment |
|---|---|---|---|---|---|
| 7 | 8.39 | d, $J$ = 7.2 Hz, 1H | Z | NH | $Z_{amide}$ |
| 10 | 8.28 | d, $J$ = 7.5 Hz, 1H | K | NH | $K_{amide}$ |
| 4 | 8.22 | d, $J$ = 8.6 Hz, 1H | V | NH | $V_{amide}$ |
| 1 | 8.13 | d, $J$ = 7.5 Hz, 1H | I | NH | $I_{amide}$ |
| 5 | 7.55 | s, 1H | C-terminal | NH | Amide Capping |
| 6 | 7.10 | s, 1H | C-terminal | NH | Amide Capping |
| 8 | 4.40 | m, 1H | Z | CH | $Z_\alpha$ |
| 11 | 4.27 | m, 1H | K | CH | $K_\alpha$ |
| 3 | 4.09 | m, 2H | V | CH | $V_\alpha$ |
| 2 | | | I | CH | $I_\alpha$ |
| 16 | 2.99 | t, $J$ = 8.3 Hz, 3H | K | $CH_2$ | $K_\epsilon$ |
| 38 | 2.02 | s, 3H | N-terminal | Acetyl | Acetyl capping |
| 29 | 2.01 | m, 1H | V | CH | $V_\beta$ |
| 13 | 1.8 | m, 3H | K | $CH_2$ | $K_\beta$ |
| 33 | | | I | CH | $I_\beta$ |
| 15 | 1.64 | m, 9H | K | $CH_2$ | $K_\gamma$ |
| 21 | | | Z | $CH_2$ | $Z_\beta$ |
| $Z_{ring}$ | | | Z | CH/$CH_2$ | $Z_{ring}$ |
| 35 | 1.45 | m, 3H | I | CH | $I_\gamma$ |
| 14 | | | K | $CH_2$ | $K_\delta$ |
| $Z_{ring}$ | 1.32 | m, 1H | Z | CH | $Z_{ring}$ |
| 35 | 1.18 | m, 4H | I | CH | $I_\gamma$ |
| $Z_{ring}$ | | | Z | CH/$CH_2$ | $Z_{ring}$ |
| $Z_{ring}$ | 0.90 | m, 14H | Z | CH | $Z_{ring}$ |
| 30 | | | V | $CH_3$ | $V_{\gamma 1}$ |
| 31 | | | V | $CH_3$ | $V_{\gamma 2}$ |
| $Z_{ring}$ | | | Z | CH | $Z_{ring}$ |
| 36 | | | I | $CH_2$ | $I_\delta$ |
| 34 | | | I | $CH_3$ | $I_{\gamma'}$ |

FIG. 8

|  | 1 mg/ml | 2 mg/ml | 3 mg/ml | 4 mg/ml | 6 mg/ml | 8 mg/ml |
|---|---|---|---|---|---|---|
| IVFK | No gel | < 3 hours | < 20 min | < 5 min | < 1 min | < 1 min |
|  | 1.83 mM | 3.66 mM | 5.49 mM | 7.32 mM | 10.96 mM | 14.64 mM |
| IVZK | No gel | < 15 min | < 5 min | < 5 min | < 1 min | < 1 min |
|  | 1.81 mM | 3.62 mM | 5.43 mM | 7.24 mM | 10.86 mM | 14.48 mM |

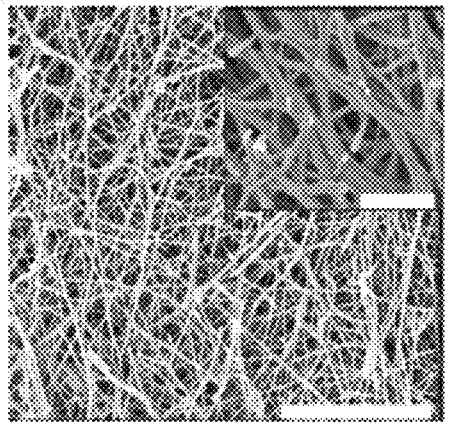
FIG. 15
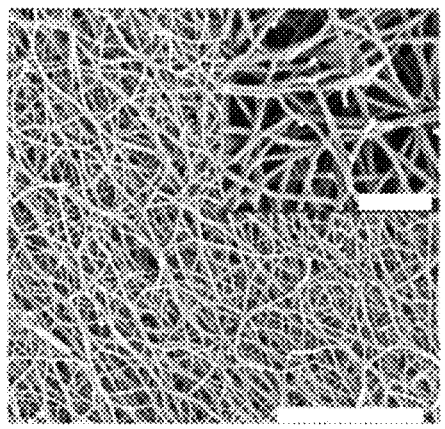
FIG. 16
| | Low concentration | High concentration |
|---|---|---|
| IVFK | Porosity = 47.43 ± 2.14 % | Porosity = 39.04 ± 0.76 % |
| IVZK | Porosity = 46.91 ± 3.12 % | Porosity = 38.42 ± 1.00 % |
FIG. 17

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: Synthetic primer: ALP forward

<400> SEQUENCE: 1
gcacctgcct tactaactc                                                  19

<210> SEQ ID NO 2
<211> LENGTH: 18
<212> TYPE: DNA
<213> ORGANISM: Artificial Sequence
<220> FEATURE:
<223> OTHER INFORMATION: Synthetic primer: ALP reverse

<400> SEQUENCE: 2
agacacccat cccatctc                                                   18

<210> SEQ ID NO 3
<211> LENGTH: 21
<212> TYPE: DNA
<213> ORGANISM: Artificial Sequence
<220> FEATURE:
<223> OTHER INFORMATION: Synthetic primer: IBSP Forward

<400> SEQUENCE: 3
cactggagcc aatgcagaag a                                               21

<210> SEQ ID NO 4
<211> LENGTH: 20
<212> TYPE: DNA
<213> ORGANISM: Artificial Sequence
<220> FEATURE:
<223> OTHER INFORMATION: Synthetic primer: IBSP Reverse

<400> SEQUENCE: 4
```
tggtggggtt gtaggttcaa                                                     20

<210> SEQ ID NO 5
<211> LENGTH: 18
<212> TYPE: DNA
<213> ORGANISM: Artificial Sequence
<220> FEATURE:
<223> OTHER INFORMATION: Synthetic primer: BMP-2 Forward

<400> SEQUENCE: 5
tgcggtctcc taaaggtc                                                       18

<210> SEQ ID NO 6
<211> LENGTH: 18
<212> TYPE: DNA
<213> ORGANISM: Artificial Sequence
<220> FEATURE:
<223> OTHER INFORMATION: Synthetic primer: BMP-2 Reverse

<400> SEQUENCE: 6
aactcgaact cgctcagg                                                       18

<210> SEQ ID NO 7
<211> LENGTH: 22
<212> TYPE: DNA
<213> ORGANISM: Artificial Sequence
<220> FEATURE:
<223> OTHER INFORMATION: Synthetic primer: RUNX2 Forward

<400> SEQUENCE: 7
tcaacgatct gagatttgtg gg                                                  22

<210> SEQ ID NO 8
<211> LENGTH: 21
<212> TYPE: DNA
<213> ORGANISM: Artificial Sequence
<220> FEATURE:
<223> OTHER INFORMATION: Synthetic primer: RUNX2 Reverse

<400> SEQUENCE: 8
ggggaggatt tgtgaagacg g                                                   21

<210> SEQ ID NO 9
<211> LENGTH: 21
<212> TYPE: DNA
<213> ORGANISM: Artificial Sequence
<220> FEATURE:
<223> OTHER INFORMATION: Synthetic primer: osteopontin Forward

<400> SEQUENCE: 9
gaagtttcgc agacctgaca t                                                   21

<210> SEQ ID NO 10
<211> LENGTH: 22
<212> TYPE: DNA
<213> ORGANISM: Artificial Sequence
<220> FEATURE:
<223> OTHER INFORMATION: Synthetic primer: osteopontin Reverse

<400> SEQUENCE: 10
gtatgcacca ttcaactcct cg                                                  22

SCAFFOLDS FROM SELF-ASSEMBLING TETRAPEPTIDES SUPPORT 3D SPREADING, OSTEOGENIC DIFFERENTIATION AND ANGIOGENESIS OF MESENCHYMAL STEM CELLS

CROSS-REFERENCE TO RELATED APPLICATIONS

This application claims benefit of priority of U.S. Provisional Patent Application No. 63/067,962, entitled "Tetrameric Self-Assembling Peptides Support 3D Spreading and Osteogenic Differentiation of Mesenchymal Stem Cells," filed Aug. 20, 2020; U.S. Provisional Patent Application No. 63/067,913, entitled, "Peptide Compound with Repetitive Sequences" filed Aug. 20, 2020; and U.S. patent application Ser. No. 17/401,434, entitled "Peptide Compound with Repetitive Sequences" filed Aug. 13, 2021. The entire contents and disclosures of these patent applications are incorporated herein by reference in their entirety.

REFERENCE TO A "SEQUENCE LISTING" SUBMITTED AS AN ASCII TEXT FILE

The present application includes a Sequence Listing which has been submitted electronically in an ASCII text format. This Sequence Listing is named 114147-23816US01_sequence listing.TXT was created on Jun. 24, 2021, is 2,429 bytes in size and is hereby incorporated by reference in its entirety.

BACKGROUND

Field of the Invention

The present disclosure relates generally to an osteo-tissue graft capable of promoting bone tissue growth and regeneration, comprising at least one self-assemble peptide and mesenchymal stem cells (MSCs). The present disclosure further relates to a method of preparing such an osteo-tissue graft.

Background of the Invention

Bone is a solid organ that undergoes calcification and forms the body's skeletal tissue. Considerable loss of bone density occurs as a result of trauma, disease, infection, and aging. Therefore, bone correction is often needed. This process is mostly done through surgery, implementing metal or ceramic implants and grafts.[1] More than 1.5 million bone grafts are fabricated annually.[2] There are three primary types of bone grafts used, i.e., autografts, allografts, and xenografts, with all having serious drawbacks. These include running the risk of donor-site morbidity, infection, blood loss, immune rejection, pain, different rates of resorption, and poor performance in some clinical procedures.[3-6] To overcome these challenges, tissue defects have been treated through tissue engineering strategies.[7] The subject of bone tissue engineering includes the use of cells, biomaterials, and suitable growth factors to create an ideal environment that promotes bone tissue growth and regeneration.[8,9]

Bone-marrow-derived mesenchymal stem cells (BM-MSCs) have emerged as key players in tissue engineering and regenerative medicine because of their multipotency. They have the ability to readily produce progenitors for many cell types, such as osteocytes, chondrocytes, adipocytes, and myocytes.[10] In addition to this, BM-MSCs avoid the ethical questions that arise from the use of embryonic stem cells, are reported to have immune-suppressive effects, and are easy to isolate, culture, and expand.[11,12] In the context of bone tissue engineering, BM-MSCs have been reported to have the capability to differentiate into the osteogenic lineage in vitro if cultured with media supplemented with appropriate differentiation cocktail.[13]

Scaffolds have played an important role in the repair and regeneration of a wide range of tissue types. These structures provide a supportive matrix and an essential environment for cells to spread, migrate, grow, and differentiate into specific lineages.[12] Naturally derived materials like tumor-derived basement membrane matrix gel (Matrigel),[14-16] collagen,[17,18] can enhance cell and tissue function and regeneration. Nonetheless, there are questions about the safety of Matrigel in the possibility to use it for clinical purposes because its components are originated from Engelbreth-Holm-Swarm sarcomas[19] and because it is established that Matrigel and the basement membrane matrix promote tumor growth and tumorigenesis in vivo.[20,21] On the other hand, collagen, an essential component found in the extracellular matrix (ECM) has been extensively utilized as a supportive compound in tissue engineering scaffolds because it shows no or low inflammatory responses, low antigenicity, and biodegradability.[22] However, collagen matrices lack sufficient mechanical strength and degrade quite quickly.[23]

Bone scaffolds should have the necessary osteoinductive and osteoconductive properties and good mechanical strength to direct neighboring cells to ectopic bone formation in the area of interest.[24-26] Several scaffolds have been tested to temporarily fill bone defects, which need an additional surgery for replacement or removal. The design of a nanofibrous scaffold, capable of guiding the osteogenic differentiation of BM-MSCs, is a promising strategy to achieve clinically successful bone grafts.[12,27] As autogenous peptides exist naturally within the human body, their nontoxic and biocompatible nature should come as no surprise. Peptides have all of the molecular information required to form well-ordered nanostructures.[28] These materials can be designed to have bioactive epitopes to enhance adhesion,[29] migration,[30] and differentiation[31] and other biological functions such as mineralization.[32] However, recreating the ECM's complexity, diversity, and dynamic existence remains an unresolved issue.[33] Also, because of their low mechanical properties, the use of hydrogels in bone tissue engineering is limited.[34] Nowadays, self-assembling peptides have gained attention in regenerative medicine including bone regeneration. Recently, the HA-Tyr/RGDS-PA/osteo-PA/angio-PA hydrogel was found to success-fully promote human adipose-derived mesenchymal stem cell (h-AMSC) adhesion and osteoblastic differentiation and support human umbilical vein endothelial cells (HUVECs) to grow into vascular tubules.[33] Another group reported that the E1Y9 (Ac-E-YEYKYEYKY-NH2) amphiphilic peptide can be self-assembled into fibers in the presence of the $Ca^{2+}$ ion. These peptides are found to stimulate osteoblast cell growth as well as differentiation.[35] Furthermore, RATEA16 loading with the vascular endothelial growth factor (VEGF) and bone morphogenetic protein 2 (BMP-2) was reported to support cell proliferation, migration, and tube formation of HUVECs as well as osteogenesis of human apical papilla stem cells (SCAPs).[36] However, all of these hydrogels were functionalized with bioactive sequences to enhance their ability to stimulate osteogenic differentiation.

RADA16 is one of the most widely used self-assembling peptides for three-dimensional (3D) cell cultures. It was successfully investigated to achieve new bone formation and support osteogenic differentiation.[37-40] Due to its acidity, the pH of the self-assembled RADA16 hydrogel needs to be equilibrated to physiological pH prior to cell seeding or in vivo transplantation by immediately adding a large amount of media.[41-43] Furthermore, successful bone regeneration needs both good osteogenesis and vascularization, providing scaffolds that can support both osteogenic and angiogenic properties is much required. Therefore, an improved material that can support new bone formation and osteogenic differentiation is needed.

SUMMARY

According to a first broad aspect, the present disclosure provides a 3-dimensional osteo-tissue graft comprising: live mesenchymal stem cells (MSCs), and ultrashort self-assembling peptide scaffolds. In one embodiment, the 3-dimensional osteo-tissue graft further comprises live umbilical vein endothelial cells According to a second broad aspect, the present disclosure provides a method of create a 3-dimensional osteo-tissue graft comprising: suspending MSCs in tissue culture media; dissolving an ultrashort self-assembling peptide in buffer solution; loading a 3D bioprinter with the suspended MSCs and peptide solution; printing the 3-dimensional osteo-tissue graft using the 3D bioprinter; and 3D culturing the MSCs by keeping the 3-dimensional osteo-tissue graft in osteogenic induction media.

Other aspects and features of the present disclosure will become apparent to those skilled in the art upon review of the following description of specific embodiments of the invention in conjunction with the accompanying figures.

BRIEF DESCRIPTION OF THE DRAWINGS

The patent or application file contains at least one drawing executed in color. Copies of this patent or patent application publication with color drawing(s) will be provided by the office upon request and payment of the necessary fee.

The accompanying drawings, which are incorporated herein and constitute part of this specification, illustrate exemplary embodiments of the invention, and, together with the general description given above and the detailed description given below, serve to explain the features of the invention.

FIG. 5 illustrates $^1$H-NMR chemical shifts of IVFK according to an exemplary embodiment of the present disclosure.

FIG. 8 illustrates $^1$H-NMR chemical shifts of IVZK according to an exemplary embodiment of the present disclosure.

FIG. 15 shows the morphology of the nanofibrous hydrogels formed by IVFK according to an exemplary embodiment of the present disclosure.

FIG. 16 shows the morphology of the nanofibrous hydrogels formed by IVZK according to an exemplary embodiment of the present disclosure.

FIG. 17 shows the porosity of both IVFK and IVZK peptide hydrogels at different concentrations according to an exemplary embodiment of the present disclosure.

DETAILED DESCRIPTION OF THE INVENTION

Definitions

Figure 1:
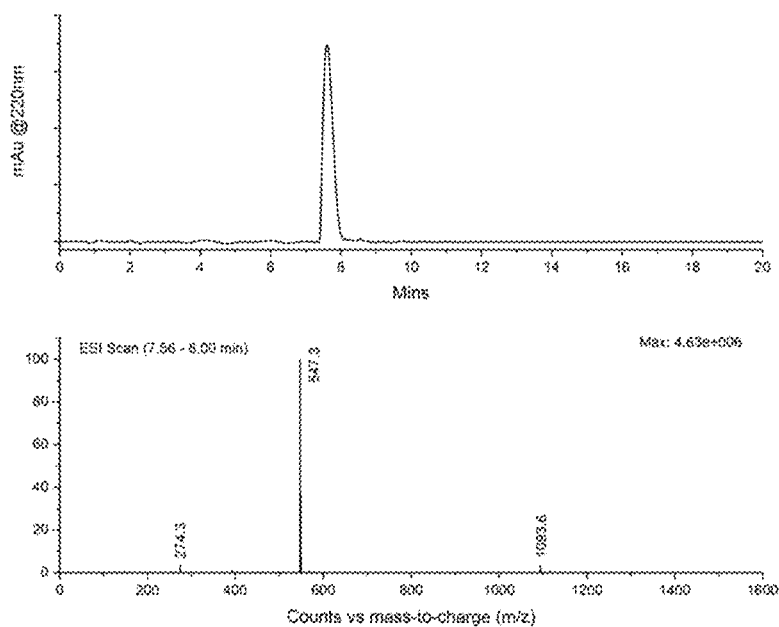
FIG. 1 illustrates the characterization of IVFK by using LC-MS according to an exemplary embodiment of the present disclosure.

Where the definition of terms departs from the commonly used meaning of the term, applicant intends to utilize the definitions provided below, unless specifically indicated.

Unless defined otherwise, all technical and scientific terms used herein have the same meaning as is commonly understood to which the claimed subject matter belongs. In the event that there is a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

For purposes of the present disclosure, the term "comprising", the term "having", the term "including," and variations of these words are intended to be open-ended and mean that there may be additional elements other than the listed elements.

For purposes of the present disclosure, directional terms such as "top," "bottom," "upper," "lower," "above," "below," "left," "right," "horizontal," "vertical," "up," "down," etc., are used merely for convenience in describing the various embodiments of the present disclosure. The embodiments of the present disclosure may be oriented in various ways. For example, the diagrams, apparatuses, etc., shown in the drawing figures may be flipped over, rotated by 90° in any direction, reversed, etc.

For purposes of the present disclosure, a value or property is "based" on a particular value, property, the satisfaction of a condition, or other factor, if that value is derived by performing a mathematical calculation or logical decision using that value, property or other factor.

For purposes of the present invention, the term "gel" and "hydrogel" are used interchangeably. These terms refer to a is a network of polymer chains, entrapping water or other aqueous solutions, such as physiological buffers, of over 99% by weight. In an embodiment of the present invention, the polymer chains may be a peptide with repetitive sequences.

For purposes of the present disclosure, the term "ultra-short peptide" and "self-assembling peptide" are used interchangeably. These terms refer to a sequence containing 3-7 amino acids. The peptides according an aspect of the present disclosure are also particularly useful for formulating aqueous or other solvent compositions, herein also sometimes referred to as "inks" or "bioinks", which may be used for printing structures, in particular 3D structures. Such printed structures make use of the gelation properties of the peptides according to features of the present disclosure.

For purposes of the present disclosure, the term "bioinks" as used herein means materials used to produce engineered/artificial live tissue using 3D printing. In the present disclosure, these bioinks are mostly composed of hydrogel or organogel with optional cellular components embedded.

For purposes of the present disclosure, the term "scaffolds" as used herein means the ultra-short peptide or other polymer materials in the bioinks that provide support for the cellular components.

For purposes of the present disclosure, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

DESCRIPTION

While the invention is susceptible to various modifications and alternative forms, specific embodiment thereof has been shown by way of example in the drawings and will be described in detail below. It should be understood, however that it is not intended to limit the invention to the particular forms disclosed, but on the contrary, the invention is to cover all modifications, equivalents, and alternatives falling within the spirit and the scope of the invention.

In one embodiment, the presently disclosed bone transplant contains peptides that can quickly solidify and provide a 3D environment that supports cell growth, migration, proliferation, and differentiation, under physiological conditions and a specific concentration.[44, 45] These peptides need a low concentration to quickly form a gel with good mechanical properties. Furthermore, the stiffness of these peptide hydrogels can be easily tuned by increasing the peptide concentration, which provides a wide range of hydrogels with different stiffnesses for 3D cell culture applications. These hydrogels are made from amphiphilic ultra-short peptides[44] that self-assemble into nanofibrous scaffolds, which are excellent candidates for use in tissue engineering applications.[46,47] The resulting hydrogels are biocompatible and quickly gel to provide a 3D structure similar to that of the extracellular matrix (ECM).[48, 49]

Self-Assembling Ultrashort Tetrapeptides

In one embodiment, the peptides form the scaffolds of the osteo-tissue grafts are at least one of the two self-assembling tetrapeptides, aromatic IVFK and nonaromatic IVZK. These two self-assembling tetrapeptides rationally designed based on a previous report of the positive impact of lysine (Lys, K) containing peptide hydrogels on cell expansion.[41, 51] The positively charged amine group from the lysine residue and the polarity of the surface have been reported to mediate cell adhesion and spreading.[52, 53] These peptides are composed of a positively charged amino acid (Lys) in the C-terminal and three nonpolar amino acids as a hydrophobic tail. Due to their amphiphilic structure, both peptides are able to self-assemble to form ordered aggregates.[52-54] The aggregation rate of the peptides can be enhanced by alternating the aromatic phenylalanine (Phe, F) residue in IVFK with more hydrophobic, nonaromatic cyclohexylalanine (Cha, Z) as can be found in IVZK.[55]

Figure 2:
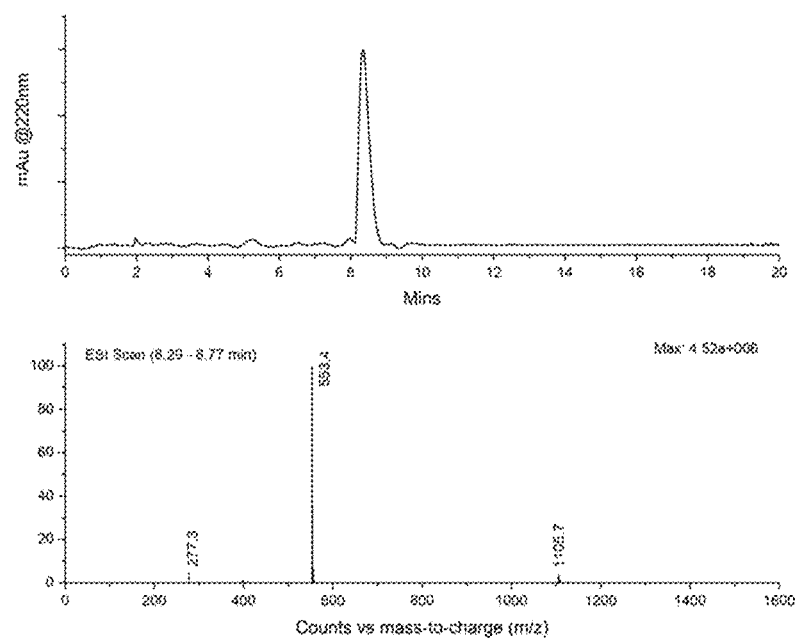
FIG. 2 illustrates the characterization of IVZK by using LC-MS according to an exemplary embodiment of the present disclosure.

The characterization of IVFK and IVZK are performed using LC-MS. FIG. 1 shows the characterization of IVFK. In FIG. 1, the top panel illustrates the liquid chromatogram of IVFK by the absorbance at 220 nm, while the bottom panel illustrates mass spectrum of IVFK, with MS: (m/z) calculated 546.7, $[M+2H]^{2+}$ found 274.3, $[M+H]^+$ found 547.3, and $[2M+H]^+$ found 1093.6. FIG. 2 shows the characterization of IVZK. In FIG. 2, the top panel illustrates the liquid chromatogram of IVZK by the absorbance at 220 nm, while the bottom panel illustrates mass spectrum of IVZK, with MS: (m/z) calculated 552.8, $[M+2H]2+$ found 277.3, $[M+H]^+$ found 553.4, and $[2M+H]^+$ found 1105.7.

$^1$H-NMR assignment for IVFK and IVZK in 90% $H_2O$-10% $D_2O$ mixture is summarized below:

$^1$H NMR IVFK (600 MHZ, $H_2O+D_2O$) δ 8.46 (d, J=7.1 Hz, 1H), 8.26 (d, J=7.7 Hz, 1H), 8.13 (d, J=2.6 Hz, 1H), 8.12 (d, J=3.6 Hz, 1H), 7.32 (m, 5H), 6.99 (s, 1H), 6.86 (s, 1H), 4.21 (m, 1H), 4.09 (t, J=14.6 Hz, 1H), 4.07 (t, J=8.2 Hz, 1H), 3.06 (m, 3H), 2.96 (t, J=8.1 Hz, 3H), 2.02 (s, 3H), 1.96 (m, 1H), 1.77 (m, 2H), 1.64 (m, 3H), 1.46 (m, 1H), 1.36 (m, 2H), 1.16 (m, 1H), 0.89 (d, J=6.9 Hz, 3H), 0.85 (m, 6H), and 0.78 (d, J=7.0 Hz, 3H)

$^1$H NMR IVZK (600 MHZ, $H_2O+D_2O$) δ 8.39 (d, J=7.2 Hz, 1H), 8.28 (d, J=7.5 Hz, 1H), 8.22 (d, J=8.6 Hz, 1H), 8.13 (d, J=7.5 Hz, 1H), 7.55 (s, 1H), 7.1 (s, 1H), 4.4 (m, 1H), 4.27 (m, 1H), 4.09 (m, 2H), 2.99 (t, J=8.3 Hz, 3H), 2.02 (s, 3H), 2.01 (m, 1H), 1.8 (m, 3H), 1.64 (m, 9H), 1.45 (m, 3H), 1.32 (m, 1H), 1.18 (m, 4H), and 0.9 (m, 14H)

The spatial arrangement of the peptide molecule in water due to the self-assembly are analyze using two-dimensional (2D) NMR experiments, such as correlation spectroscopy (COSY), total correlation spectroscopy (TOCSY), and nuclear Overhauser enhancement spectroscopy (NOESY).

Figure 3:
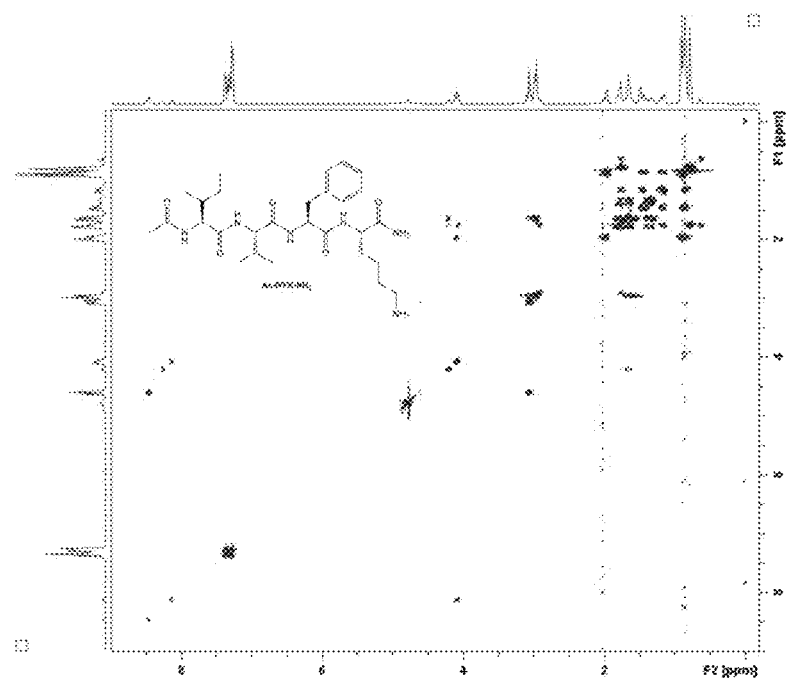
FIG. 3 illustrates $^1$H-$^1$H homonuclear through bond correlations of IVFK using COSY according to an exemplary embodiment of the present disclosure.
Figure 4:
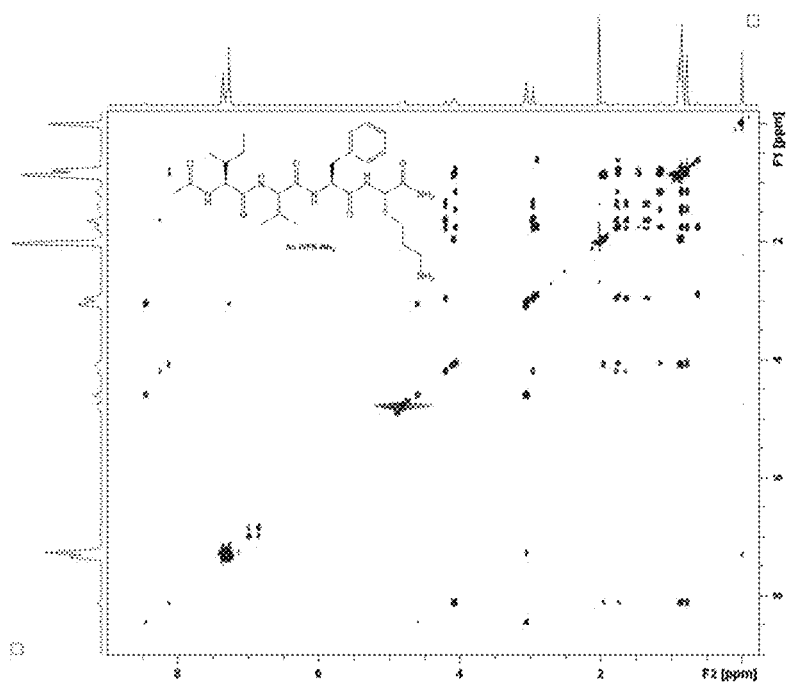
FIG. 4 illustrates $^1$H-$^1$H homonuclear through bond correlations of IVFK using TOCSY according to an exemplary embodiment of the present disclosure.

FIG. 3 shows the COSY results, illustrating $^1$H-$^1$H homonuclear through bond correlations of IVFK. FIG. 4 shows the TOCSY results, illustrating $^1$H-$^1$H homonuclear through bond correlations of IVFK. FIG. 5 illustrates $^1$H-NMR chemical shifts of IVFK.

Figure 6:
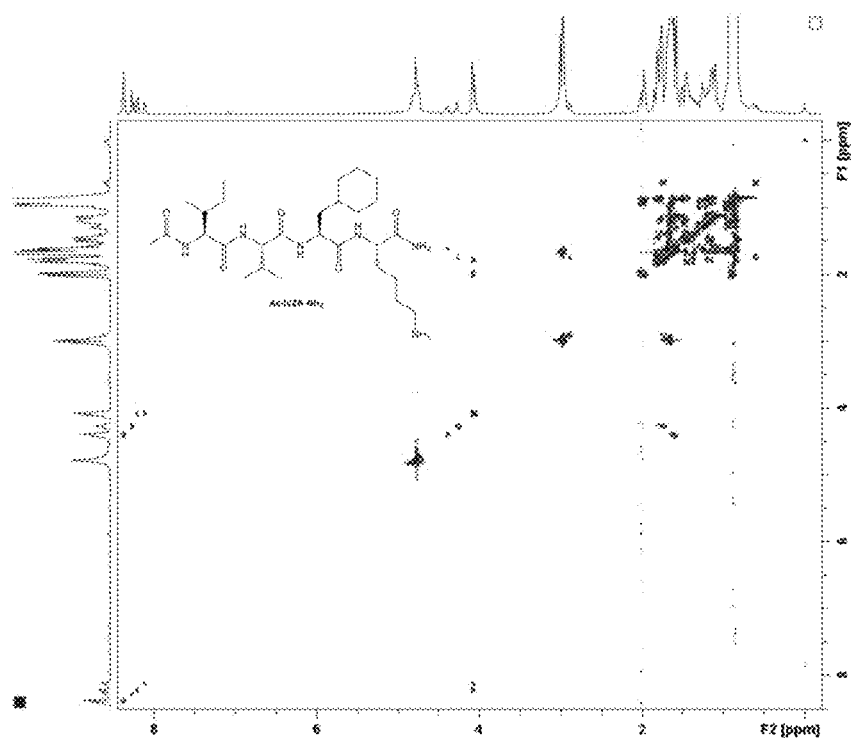
FIG. 6 illustrates $^1$H-$^1$H homonuclear through bond correlations of IVZK using COSY according to an exemplary embodiment of the present disclosure.
Figure 7:
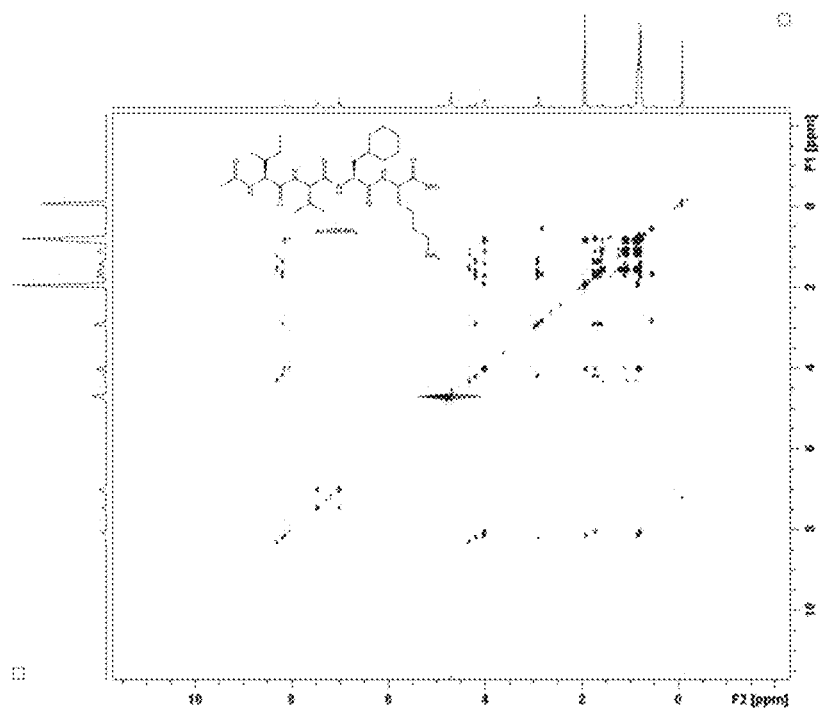
FIG. 7 illustrates $^1$H-$^1$H homonuclear through bond correlations of IVZK using TOCSY according to an exemplary embodiment of the present disclosure.

FIG. 6 shows the COSY results, illustrating $^1$H-$^1$H homonuclear through bond correlations of IVZK. FIG. 7 shows the TOCSY results, illustrating $^1$H-$^1$H homonuclear through bond correlations of IVZK. FIG. 8 illustrates $^1$H-NMR chemical shifts of IVZK.

Figure 9:
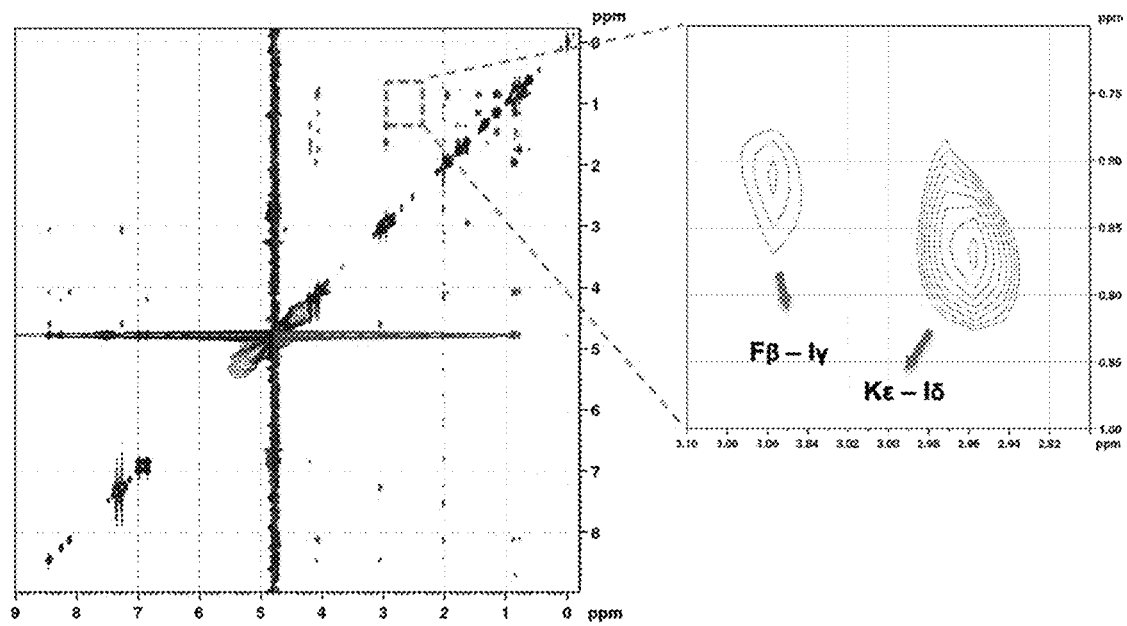
FIG. 9 illustrates NOESY contour map of IVFK according to an exemplary embodiment of the present disclosure.
Figure 10:
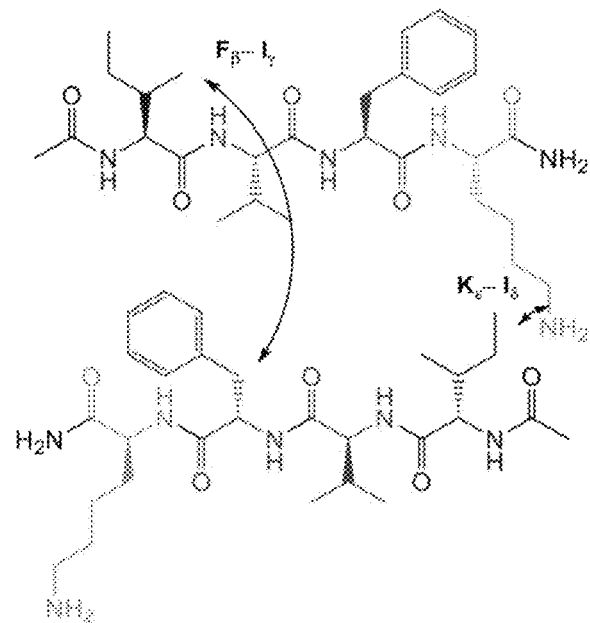
FIG. 10 illustrates antiparallel configuration of IVFK based on overlap of NOESY and TOCSY spectra of IVFK according to an exemplary embodiment of the present disclosure.

The intermolecular cross-peaks are determined by eliminating the NOESY spectra that overlap with TOCSY spectra. Using this approach, two nuclear Overhauser effect (NOE) signals from IVFK can be observed as shown in FIG. 9, in which one of them was assigned to the & proton of Lys and the & proton of the Ile. Another signal was arising from the interaction between β protons of phenyl-alanine with γ proton of Ile. From these NOESY spectra, a formation of antiparallel configuration for IVFK can be concluded, as illustrated in FIG. 10.

Figure 11:
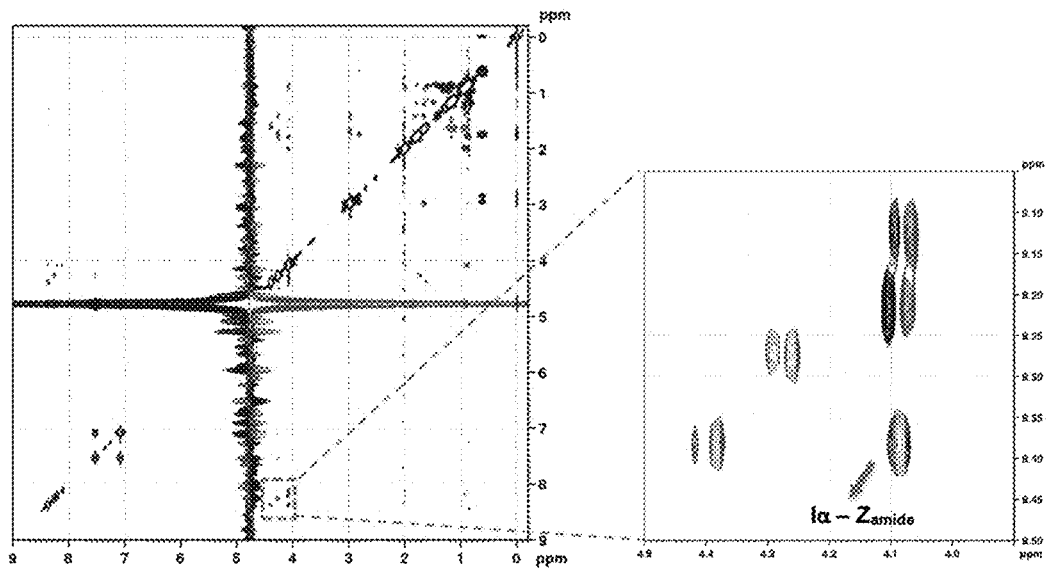
FIG. 11 illustrates NOESY contour map of IVZK according to an exemplary embodiment of the present disclosure.
Figure 12:
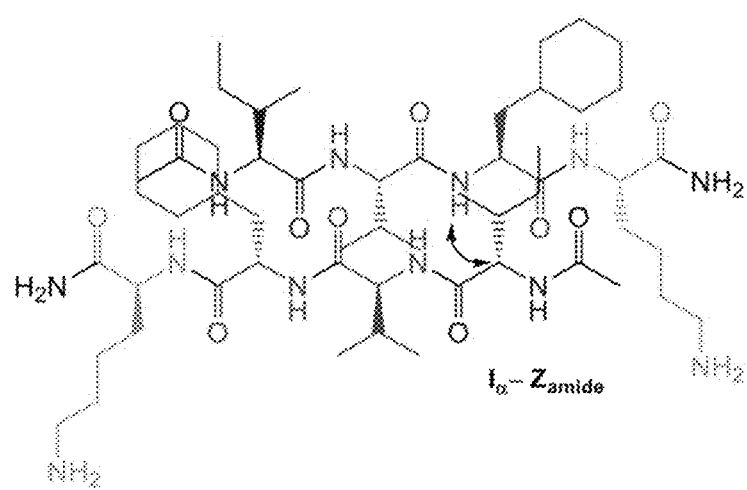
FIG. 12 illustrates antiparallel configuration of IVZK based on overlap of NOESY and TOCSY spectra of IVFK according to an exemplary embodiment of the present disclosure.

In addition, this antiparallel conformation was also predicted in IVZK illustrated in FIG. 12 as the amide proton of cyclohexylalanine interacts with the α proton of isoleucine (Ile, I), as shown in FIG. 11. This result is congruent with the previous report on the formation of antiparallel conformation during the self-assembly of ultrashort peptides.[44,49]

Figures 13, 14:
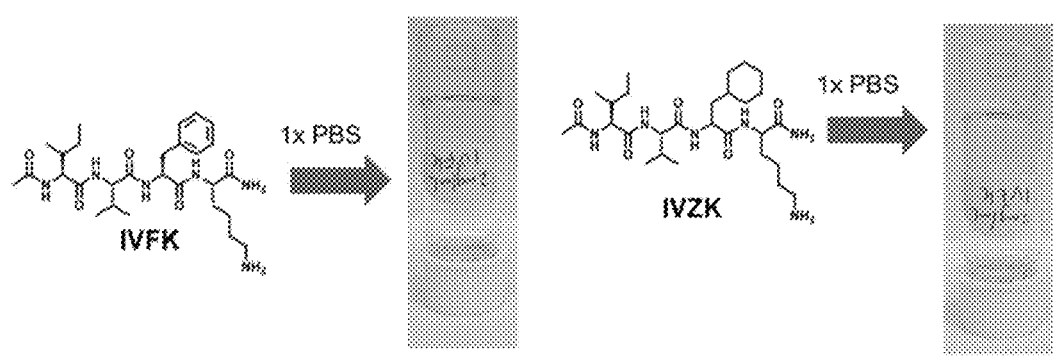
FIG. 13 shows the gelation time of IVFK and IVZK at different concentration according to an exemplary embodiment of the present disclosure.
FIG. 14 shows the gelation of IVFK and IVZK in 1× phosphate-buffered saline according to an exemplary embodiment of the present disclosure.

In one embodiment, an instant hydrogel formation can be observed when PBS buffer is added to the peptide solution. In one embodiment, the gelation time is determined using a vial inversion test performed at different peptide concentrations in 1×PBS to meet physiological conditions. FIG. 13 compares the gelation time of IVFK and IVZK at different concentration. As shown in FIG. 13, IVZK needed less time to form the hydrogel, compared to IVFK. This is most likely due to the presence of the highly hydrophobic cyclohexylalanine residue, which increases the aggregation rate.[44, 56] FIG. 14 shows the gelation of self-assembling peptides IVFK and IVZK at the critical gelation concentration (CGC) of 2 mg/mL.

Figure 18:
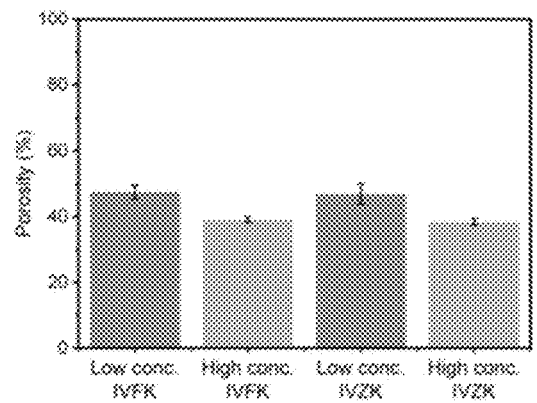
FIG. 18 illustrates the porosity of both IVFK and IVZK peptide hydrogels at different concentrations calculated from the SEM images according to an exemplary embodiment of the present disclosure.

In one embodiment, IVFK and IVZK generate supramolecular nanofibrous hydrogels in an aqueous solution at the critical gelation concentration (CGC) of 2 mg/mL. The morphology of the hydrogels is evaluated by performing SEM of dried hydrogels. The SEM micrographs confirm the presence of porous fiber networks formed by the entanglement of self-assembled peptide nanofibers. FIG. 15 shows the morphology of the nanofibrous hydrogels formed by 4 mg/mL IVFK. FIG. 16 shows the morphology of the nanofibrous hydrogels formed by 3 mg/mL IVZK. FIGS. 15 and 16 is imaged at magnifications of 100,000× and 500,000× (inset) using SEM. Scale bars in FIGS. 15 and 16 are 1 μm and 200 nm (inset). This porous structure is vital to the diffusion of necessary nutrients for cell growth. Then, the porosity of the hydrogels at low concentrations (4 mg/mL for IVFK and 3 mg/mL for IVZK) and high concentrations (8 mg/mL for both peptides) is compared and shown in FIG. 17. In FIG. 17, low concentration refers to 4 mg/mL for IVFK and 3 mg/mL for IVZK, while high concentration refers to 8 mg/mL for both peptides. The porosity of the peptide hydrogels is calculated from the SEM images of both peptides at low concentrations (4 mg/mL IVFK and 3 mg/mL IVZK) and high concentrations (8 mg/mL for both peptides) and the results are shown in FIG. 18. Taken together FIGS. 17 and 18, the results suggest that the increment of the peptide hydrogel reduced the porosity by about 8% for both peptides. The dimensions of the pores, which is at nanometer-scale, are far smaller than the cell's nucleus dimensions. Thus, the small size of the pores may then restrict the passive cell movement. Under this condition, the cellular motility can be accommodated by either mechanically distorting the surrounding matrix[57] or squeezing the cell morphology.[58-62] It has been previously reported that the porosity of a planar matrix with a nanometer-scale did not significantly affect the differentiation of stem cells, but the stiffness of the matrix regulates the differentiation.[63]

Mechanical Stiffness of Peptide Hydrogels

Figure 19:
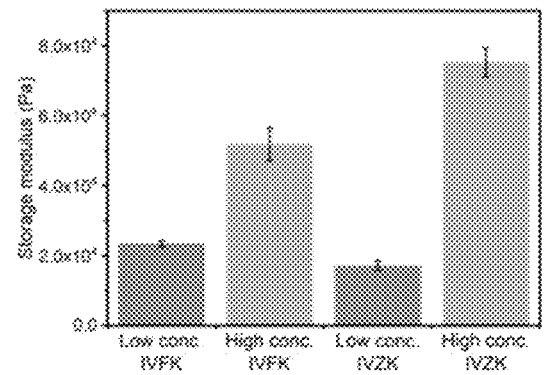
FIG. 19 illustrates the mechanical stiffness values of IVFK and IVZK hydrogels according to an exemplary embodiment of the present disclosure.

Therefore, in one embodiment, the mechanical stiffness of each peptide hydrogel is assessed by the storage modulus (G') at different concentrations. FIG. 19 shows the mechanical stiffness values of the two peptide hydrogels IVFK and IVZK 1 rad/s and 0.1% strain. Moreover, the rheological properties of peptide hydrogels at different concentrations are summarized in the table below.

| Concentration | Storage modulus (kPa) | |
| --- | --- | --- |
| | IVFK | IVZK |
| 2 mg/mL | 0.54 ± 0.06 | 10.00 ± 0.12 |
| 3 mg/mL | 7.03 ± 0.19 | 17.21 ± 1.38 |
| 4 mg/mL | 23.40 ± 0.88 | 29.77 ± 1.19 |
| 6 mg/mL | 35.79 ± 0.95 | 43.03 ± 2.81 |
| 8 mg/mL | 51.79 ± 4.73 | 75.21 ± 4.08 |

Therefore, the stiffness of the peptide hydrogels increases as the peptide concentration increases. The IVZK hydrogel showed a higher G' value compared to IVFK at the same concentration, which is most likely due to the hydrophobic cyclohexylalanine residue in IVZK. Remarkably, the stiffness range of both peptide hydrogels is within the range that supports multipotency maintenance.[51] Therefore, these self-assembled peptide hydrogels are promising candidates for use as cell-laden scaffolds in an osteogenic model.

Viability, Attachment, and Proliferation of BM-MSCs in Scaffolds

Figure 20:
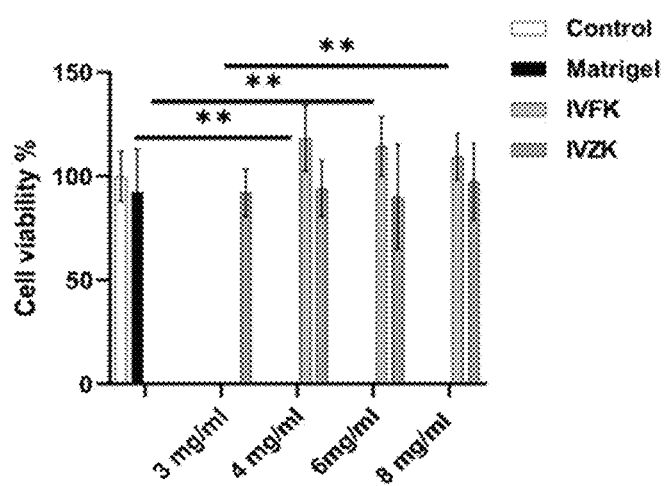
FIG. 20 illustrates the cell viability of cells cultured without and with different concentration of peptides according to an exemplary embodiment of the present disclosure.

In one embodiment, the hydrogels are screened for biocompatibility, cell attachment, and proliferation. Different concentrations of the peptides are tested for their biocompatibility of the cells within the constructs. FIG. 20 shows the cell viability assessed using the Alamar Blue assay. Control is the cells incubated for 48 h without peptides. The results in FIG. 20 shows no cytotoxicity effect of the peptides. Furthermore, IVFK showed a significant increase in cell growth compared to both controls (2D and Matrigel).

Figure 21:
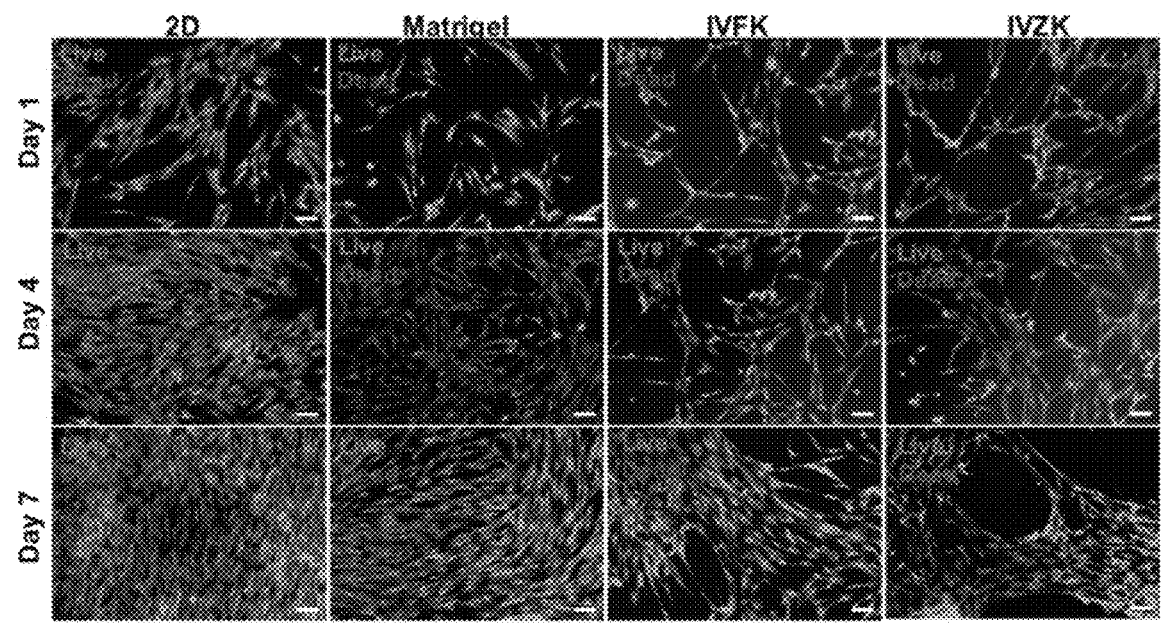
FIG. 21 shows the live/dead cell viability staining images of BM-MSCs within IVFK and IVZK peptide hydrogels according to an exemplary embodiment of the present disclosure.

Furthermore, a live/dead cytotoxicity assay is performed to evaluate the biocompatibility of MSCs in the peptides after different time points, as shown in FIG. 21. The live cells are stained in green, while the dead cells are stained in red. Scale bar in FIG. 21 is 100 μm. FIG. 21 show a high percentage of cell viability and increase in the cell growth rate during the culture time, thus indicating that there is no cytotoxicity associated with the peptides tested with the cells.

Figure 22:
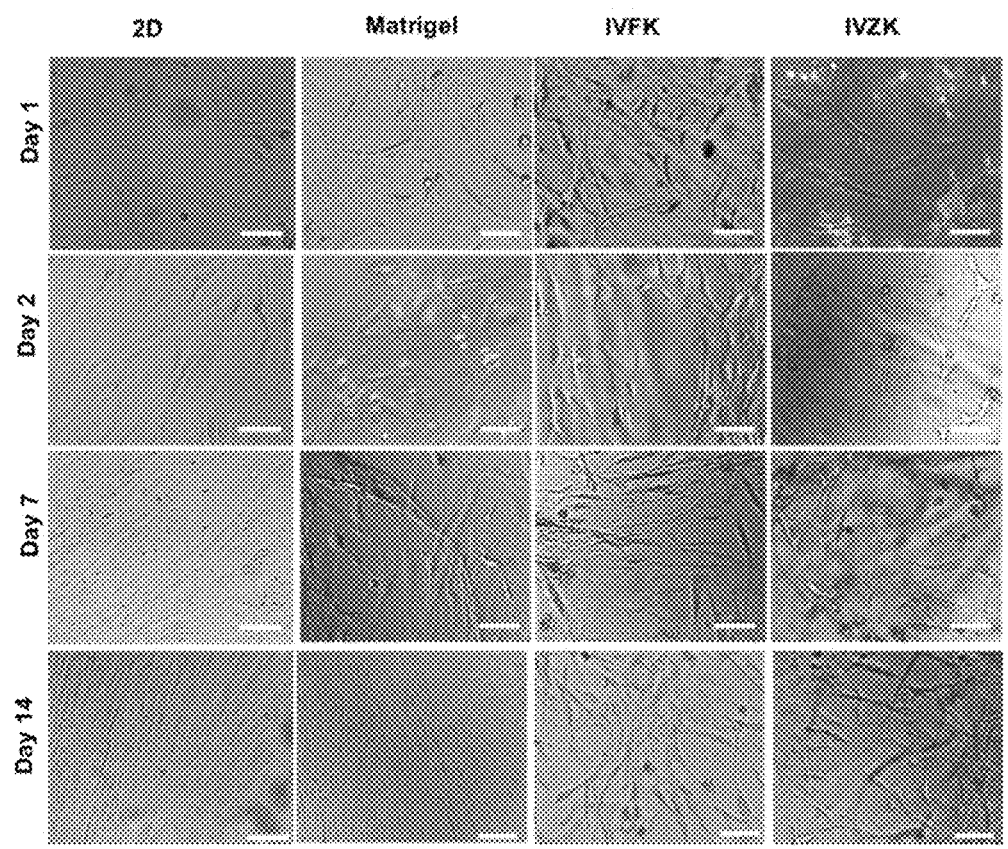
FIG. 22 shows the phase-contrast imaging of BM-MSCs cultured within different scaffolds according to an exemplary embodiment of the present disclosure.

In one embodiment, cell attachment and spreading into the hydrogels are evaluated within 24 h, 48 h, 7 days and 14 days, as shown in the bright-field microscopy images (FIG. 22) Scale bar in FIG. 22 is 100 μm. The light micrographs show long spindlelike cells spreading in all of the scaffolds tested. With culture time increasing, the cell growth increase in both peptides and the cells start spreading to form the spindle morphology. After 14 days in culture, most of the scaffolds are covered by cells, as shown in the last row of FIG. 22.

Figure 23:
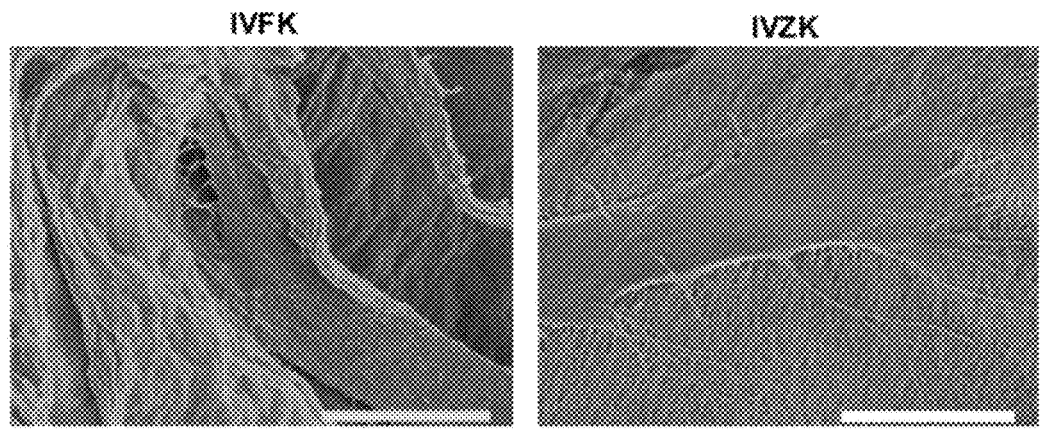
FIG. 23 shows the SEM images of BM-MSCs in IVFK and IVZK according to an exemplary embodiment of the present disclosure.

As shown in FIG. 23, SEM images for MSCs cultured after 14 days in IVFK or IVZK showed clearly the elongated spindlelike morphology of the cells and the interaction between the cell's filopodia and the matrix. Scale bars are 5 and 10 μm, in the left and right panels respectively.

Figure 24:
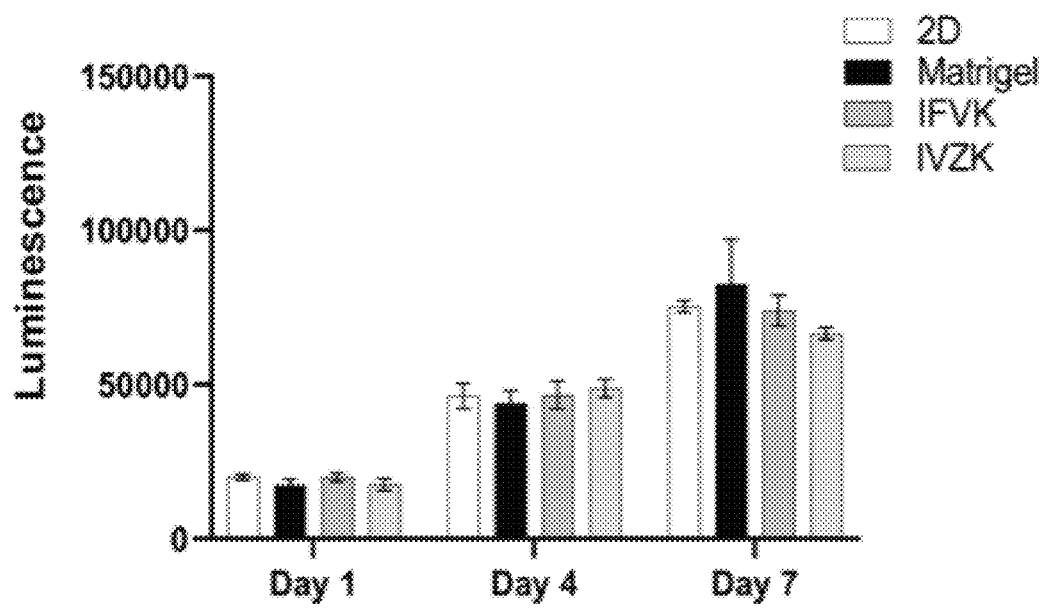
FIG. 24 illustrates the results of three-dimensional cell viability assay of BM-MSCs in IVFK and IVZK after 1, 4 and 7 days of culture according to an exemplary embodiment of the present disclosure.

Furthermore, the cell growth of MSCs in these peptide scaffolds is also estimated by examining adenosine 5'-triphosphate (ATP) release after 1 and 7 days of culture, as shown in FIG. 24. ATP production increased with time of culture, indicating the proliferation of the cells among different peptides, which is comparable to the controls.

Characterization of BM-MSCs in Scaffolds

Figure 25:
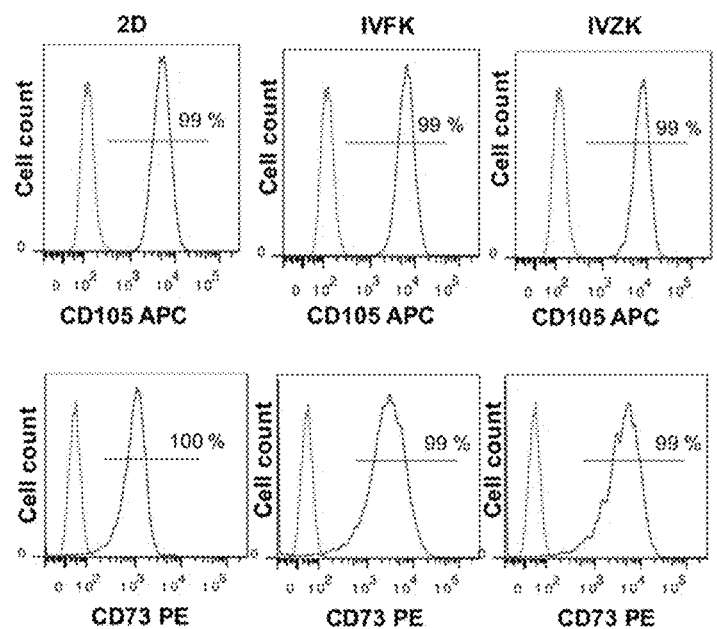
FIG. 25 illustrates the expression of BM-MSC-associated surface markers CD73, and CD105 according to an exemplary embodiment of the present disclosure.

In one embodiment, the cells' ability to maintain their multipotency and capacity for self-renewal is evaluated for two surface markers (CD73 and CD105) by flow cytometry. CD73 is a major cell surface marker defining MSCs. The CD73 expression is regulated by one of the main pathways in bone homeo-stasis.[64, 65] CD73 has recently been reported to have an important role in supporting osteogenic differentiation.[66] Endoglin CD105 is another MSC marker that plays an important role in the processes of cell proliferation, differentiation, and migration. It has also been demonstrated that CD105-positive MSCs are multipotent in vitro and can support bone formation in vivo.[67] As such, the CD105 and CD73 expressions through flow cytometry are determined after 3 days of culture. In both scaffolds tested, the cells expressed their native CD105 and CD73 as shown in FIG. 25, which suggests that the cells maintained their multipotency within the hydrogels.

Figure 26:
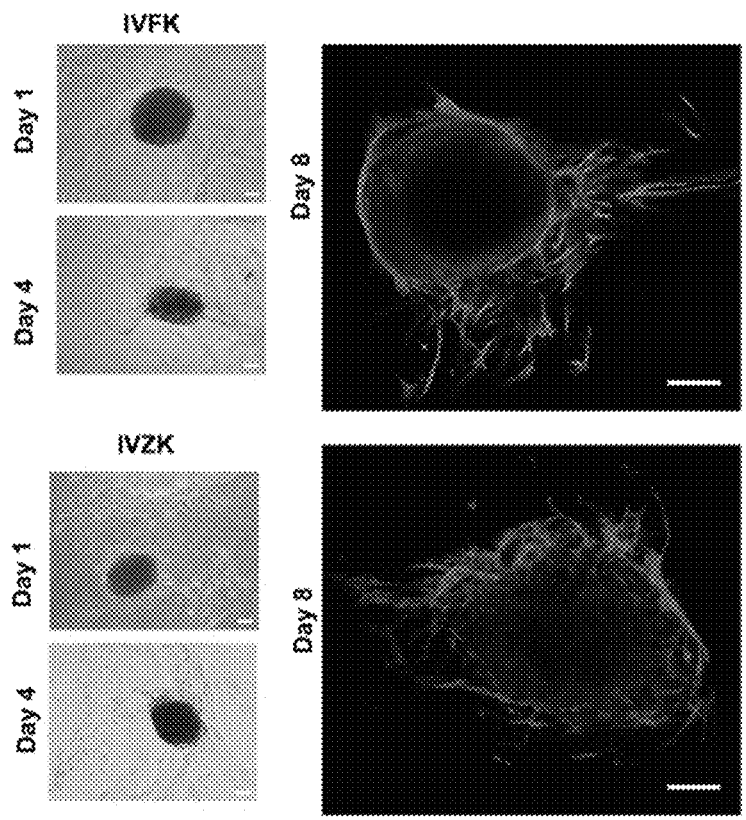
FIG. 26 shows the result of the migration assay according to an exemplary embodiment of the present disclosure.

In one embodiment, MSCs are entrapped in the fibrin clot and embedded within the gels to evaluate the ability of cells to migrate toward the hydrogel surrounding environment. A previous study reported that cells failed to migrate to the hydrogel without RGD.[50] As shown in FIG. 26, cells are able to migrate radially out of the fibrin dot into hydrogels without any further functionalization and show spindlelike shapes. In the right column of FIG. 26, F-actin is stained with phalloidin (red) and the nucleus with DAPI (blue), while scale bar is 100 μm. Confocal laser microscopy with nuclei and actin staining, as shown in the left column of FIG. 26, reveals clearly that the migration of these cells occurred.

Figure 27:
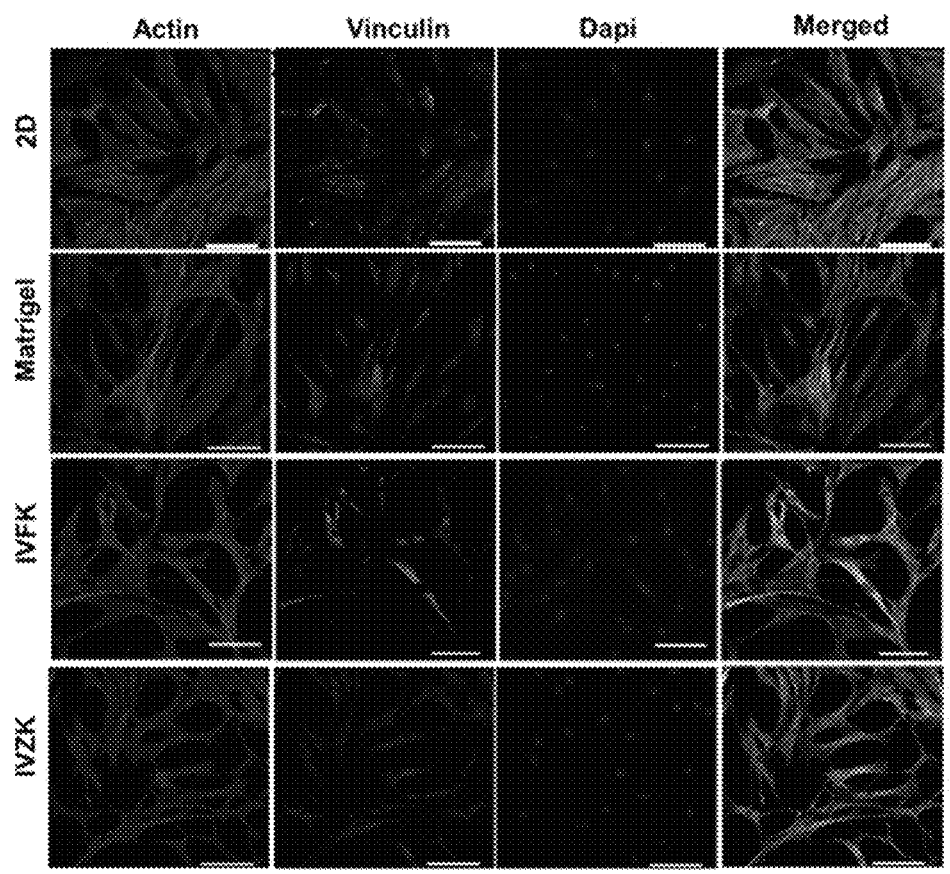
FIG. 27 shows the results of morphological studies of the BM-MSCs for the assessment of their ability to develop well-organized actin cytoskeletons through actin and cell-matrix adhesion according to an exemplary embodiment of the present disclosure.

The extracellular matrix plays an essential role in several factors affecting a cell's life such as proliferation and viability.[68] In addition to differences in cell growth and viability, cells discriminate between matrices by controlling the level of tension in cell binding and then responding with counteracting forces. In one embodiment, how the cells responded to different scaffolds is evaluated, using immunostaining of the actin cytoskeleton. Focal adhesions (FAs) act as force sensors between cells and their surrounding matrix through anchored actin microfilament bundles.[69, 70] As such, the cells are immunos-tained with F-actin using phalloidin to label the cytoskeletal arrangement. BM-MSCs are cultured in each peptide hydrogel as well as in 2D culture and Matrigel as controls. The cells are able to attach to both scaffolds without any observed changes in their morphological appearance. The cells maintained their spindle morphology, spread in all directions, exhibited a meshlike/extended actin, and made a sheet of cells covering every part of scaffolds as shown in FIG. 27. In FIG. 27, actin immunostaining is in red, vinculin is stained in green and the nucleus stained with DAPI is in blue, while the scale bar is 100 μm.

Many studies have been performed on coated 2D surfaces that are not physiologically relevant,[71-73] thus not providing an accurate reflection of the state of the cells. In contrast, 3D cultures may more closely mimic the natural cell environment and provide cells with the required stiffness conditions. One of these studies found that cells that grew on a 2D surface coated with collagen showed less actin cytoskeleton organization when compared to cells grown on a stiffer material.[74] Furthermore, previous studies also indicated that the cells cultured in stiff 3D matrices like transglutaminase cross-linked gelatin (TG-gel) with reported stiffnesses of 58 and 34 kPa formed dotlike actin filaments, and the cells did not spread through the scaffolds.[75] However, in the present disclosure, all of the matrices supported a well-established cytoskeleton with an elongated arrangement, as shown in FIG. 27. One possible explanation for these observations is that in a 2D culture, cells are directed from the latitudinal direction only, thus allowing them the possibility to extend extremely along the longitudinal direction. On the other hand, the cells cultured in a 3D environment are grown in two directions, longitudinal and latitudinal.[75] As such, the actin filaments of the cells in the 3D matrix showed better arrangement when compared to those grown in a 2D culture. Given that 3D environments provide an extra dimension for exterior mechanical responses and cell attachment, they can affect cell spreading, cell contraction, and intracellular signaling.[76, 77] Thus, the cells on 2D surfaces are less mechanically sensitive than those in 3D environments.[75] Furthermore, the cells cultured in hydrogels have a similar F-actin organization trend as in Matrigel.

Vinculin is an adhesion protein located in the cell-cell junctions and in focal adhesions (FAs), where it helps with the actin cytoskeleton connection to ECM.[64, 65] The effects of vinculin on the migratory behavior of cells in 3D collagen is presently disclosed. Deficiency in vinculin affected cell adhesion, contractility, and proliferation.[78] The confocal fluorescence images of actin cytoskeleton and vinculin for the cells in IVFK, IVZK hydrogels, and Matrigel are shown in FIG. 27. In the 2D study, the cells appeared to be more spread out. However, in 3D culture, cells showed a smaller cell spreading area. While a previous report has shown that there is no enzymatic activity of vinculin, it can bind to actin, thereby activating actin polymerization.[65] Most importantly, the distribution of vinculin was concentrated around the nuclear region, rather than being aligned with actin.[79-81]

Osteogenic Differentiation of MSCs in Self-Assembled Peptides

In one embodiment, the ability of the hydrogels to support the osteogenic differentiation of MSCs is evaluated. Cells are cultured in both hydrogels under the osteogenic condition for 3 weeks, and the efficiency of differentiation is compared to collagen. Collagen is an essential component of the ECM, which has been used widely as an important component of scaffolds in tissue engineering and is known to support both osteogenic differentiation of MSCs and angiogenesis of endothelial cells.[23]

Figure 28:
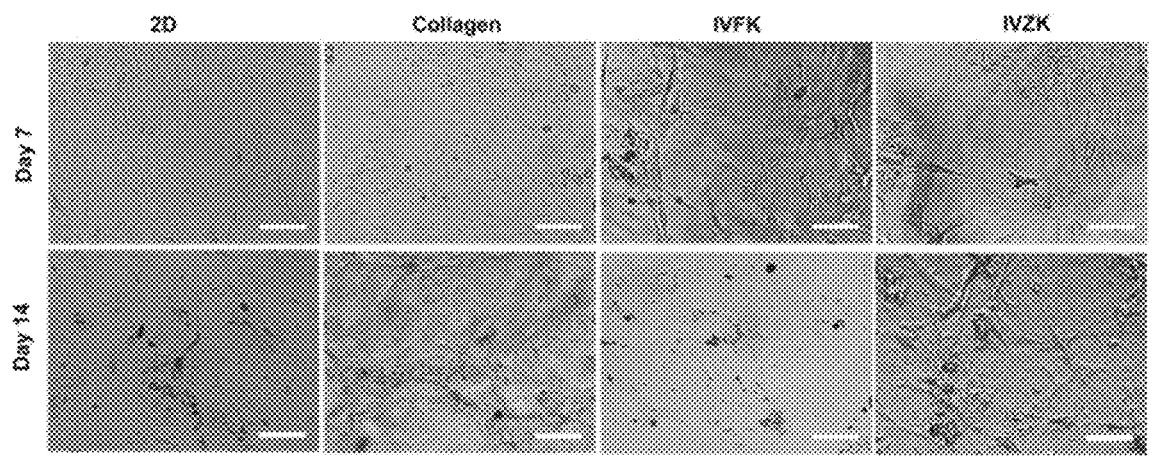
FIG. 28 shows the phase-contrast image of BM-MSCs cultured in different hydrogels in osteogenic media according to an exemplary embodiment of the present disclosure.
Figure 29:
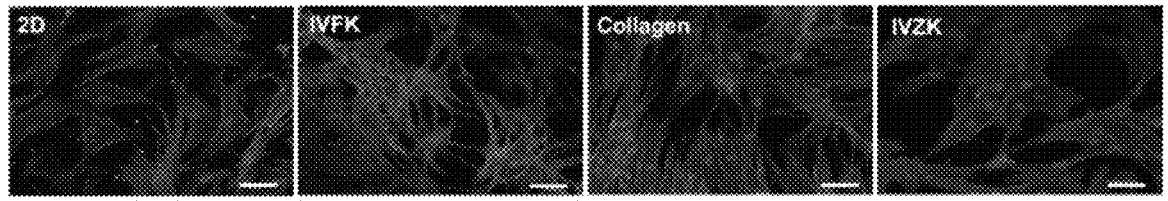
FIG. 29 shows the result of the morphology of BM-MSCs after 3 weeks of culturing in osteogenic induction media according to an exemplary embodiment of the present disclosure.
Figure 30:
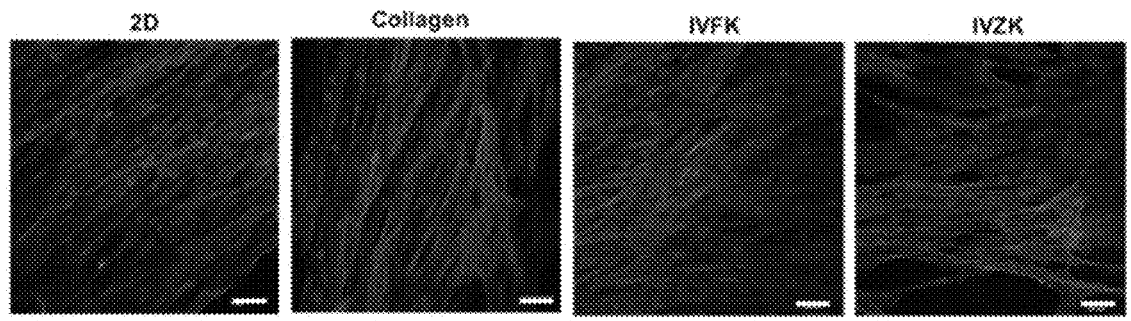
FIG. 30 shows the result of the morphology of BM-MSCs culturing in normal basal media according to an exemplary embodiment of the present disclosure.

The osteogenic differentiation potential of BM-MSCs in the hydrogels is shown in FIG. 28. The bright-field images in FIG. 28 are taken after 7 and 14 days of culture. The scale bar in FIG. 28 is 100 μm. The morphology of cells changed several days after the addition of osteogenic induction media with the mineralization clearly observed as a black aggregate after 14 days. Also, MSCs exhibit a highly branched "osteocyte-like" shape, shown by bright-field images and more dearly by confocal fluorescence images of the F-actin cytoskeleton of the cells in FIG. 28. Moreover, the in vitro morphology of hMSCs after 3 weeks of culturing in osteogenic induction media is also observed using immunostaining, as shown in FIG. 29. The cells displayed a highly branched "osteocyte-like" shape. Red represents the actin filaments, and blue represents the cell nuclei. The morphology of hMSCs shows clearly difference as compared to the morphology of hBM-MSCs cultured in normal basal media shown in FIG. 30. The scale bar in FIGS. 29 and 30 is 50 μm. This branched shape is correlated with the differentiation of stem cells toward an osteogenic lineage, which indicates that the cells successfully differentiated in both scaffolds.[82-84]

Figure 31:
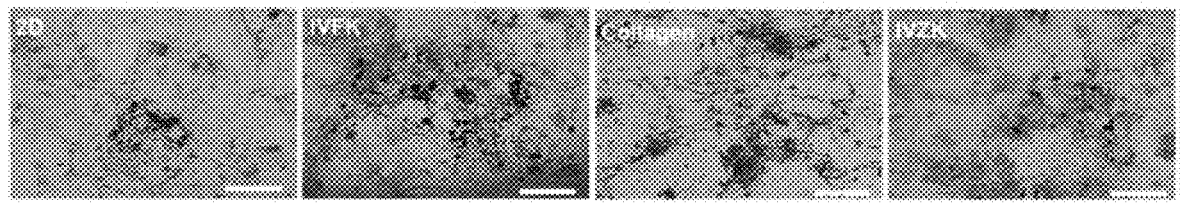
FIG. 31 shows the Alizarin red-S staining of four scaffolds, after the BM-MSCs are cultured in osteogenic induction media according to an exemplary embodiment of the present disclosure.
Figure 32:
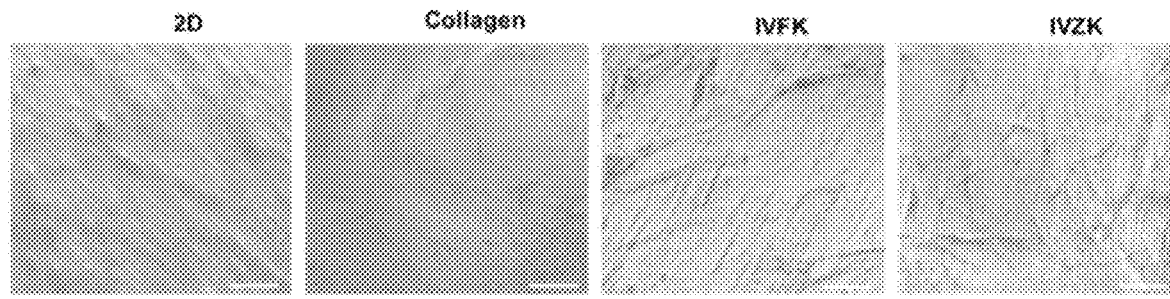
FIG. 32 shows the result of the Alizarin red-S staining of four scaffolds, after the BM-MSCs are cultured in normal basal media according to an exemplary embodiment of the present disclosure.

Alizarin red staining (ARS) is used to detect calcium deposition. The BM-MSCs cultured in the different scaffolds in the osteogenic medium are stained by Alizarin red to confirm the mineralization process during osteogenic differentiation (FIGS. 4b and S11b). FIG. 31 shows Alizarin red-S staining of four scaffolds, after the hBM-MSCs are cultured in osteogenic induction media, while FIG. 32 shows Alizarin red-S staining of four scaffolds, after the hBM-MSCs are cultured in normal basal media. The scale bar in FIGS. 31 and 32 is 100 μm. As shown in FIGS. 31 and 32, there are detectable mineral deposits, which are seen as small, stained nodules in dark-red/black color. This indicates the presence of calcium deposits. The mineral produced by the cells cultured in the IVFK hydrogel in the osteogenic medium produced the most intense ARS staining when compared to the other scaffolds tested. These results show that IVFK could accelerate the production of calcium and regulate the calcification progression of the bone matrix.

Figure 33:
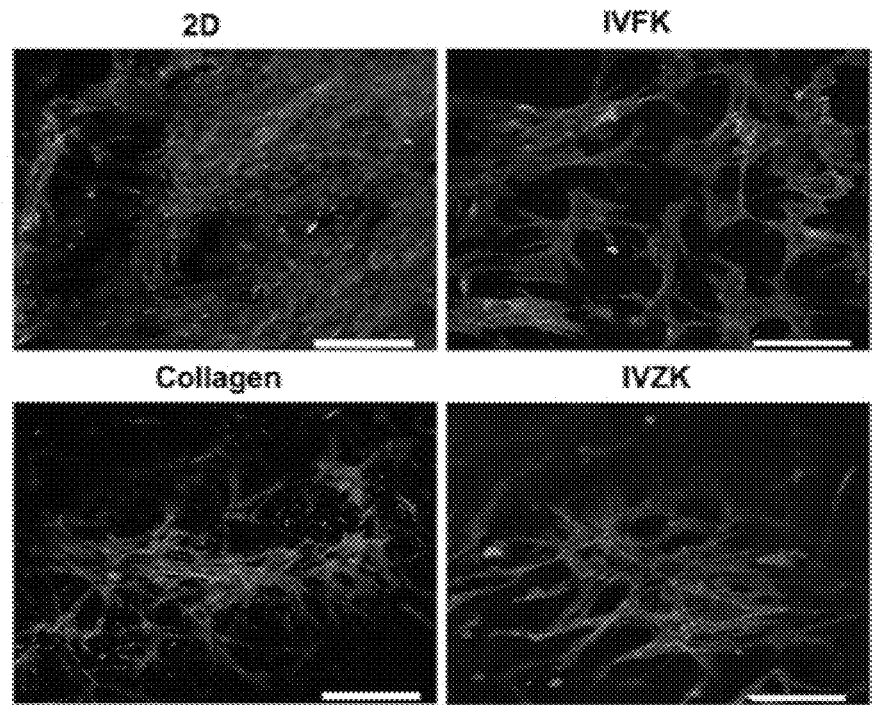
FIG. 33 shows the expression of osteocalcin according to an exemplary embodiment of the present disclosure.
Figure 34:
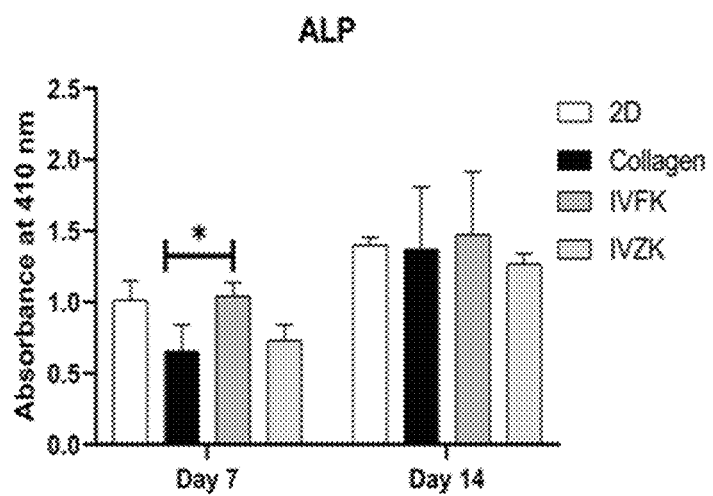
FIG. 34 illustrates ALP activity of BM-MSCs cultured on scaffolds in the osteogenic medium for 7 and 14 days according to an exemplary embodiment of the present disclosure.

In one embodiment, the BM-MSCs differentiate to the osteogenic lineage. The expression of osteocalcin is stained and imaged after 3 weeks of culture in osteogenic medium using confocal microscopy, as shown in FIG. 33. FIG. 33 is confocal images showing the expression of osteocalcin stained in green, and the cell nuclei stained in blue using DAPI. The scale bar in FIG. 33 is 100 µm. While the MSCs cultured in both scaffolds are able to express osteocalcin, the expression levels in IVFK are comparable to those cultured in the collagen control group. Additionally, the levels of alkaline phosphatase (ALP), an early osteogenic marker expressed by osteoblast cells, are also measured to confirm the commitment of BM-MSCs toward the osteogenic lineage. FIG. 34 shows the time course of ALP activity in MSCs cultured on 2D and in different scaffolds: collagen, IVFK, and IVZK after 7 and 14 days. Significantly higher ALP activity can be detected for MSCs cultured in the IVFK hydrogel than in those cultured in collagen after 7 days ($p<0.05$). Furthermore, the ALP activity increased with time during the initial 2 weeks as an indicator of osteogenic differentiation. In FIG. 34, * means $p<0.05$, indicating statistical significance.

Gene Expression Analysis

Figure 35:
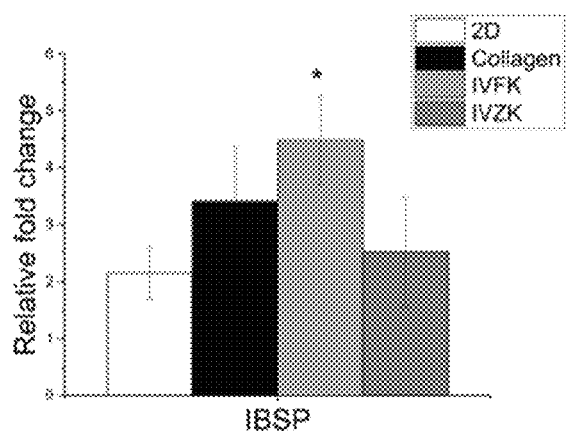
FIG. 35 illustrates IBSP expression of BM-MSCs cultured on different scaffolds after 30 days according to an exemplary embodiment of the present disclosure.
Figure 36:
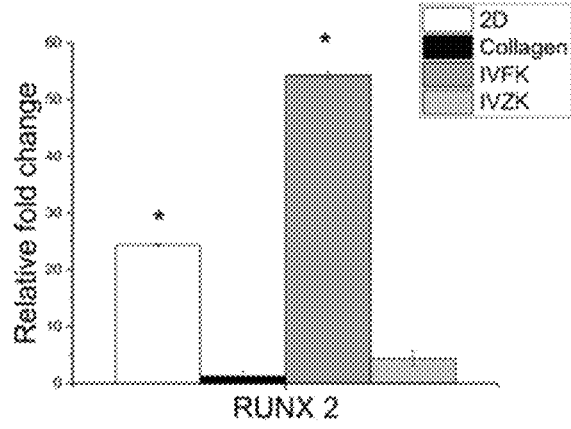
FIG. 36 illustrates RUNX2 expression of BM-MSCs cultured on different scaffolds after 30 days according to an exemplary embodiment of the present disclosure.

Real-time polymerase chain reaction (PCR) values of the BM-MSC gene expressions of the bone morphogenetic protein (BMP-2) (FIG. 37), bone sialoprotein 2 (IBSP) (FIG. 35), osteopontin (OPN) (FIG. 38), osterix (OSX) (FIG. 39), and RUNX2 (FIG. 36) are evaluated after 30 days of culture. Runx2 is an early marker of osteogenic differentiation.[85] The increase in Runx2[86] indicates that the MSCs are being directed toward the bone lineage.[1] As shown in FIG. 36 the expression of Runx2 is higher in IVFK when compared to cells cultured in other groups. In FIGS. 35-39, * mens $p<0.05$ and ** means $p<0.001$, indicating statistical significance.

Figure 37:
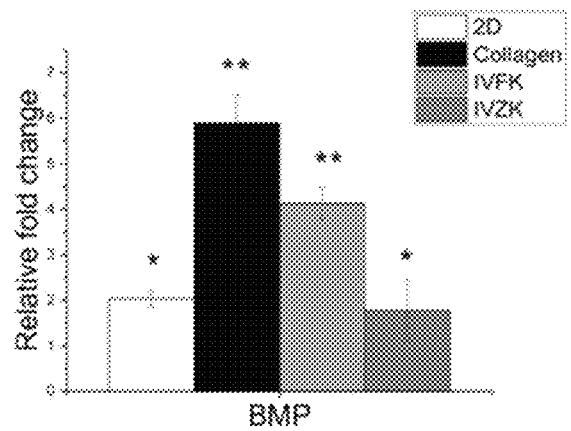
FIG. 37 illustrates BMP expression of BM-MSCs cultured on different scaffolds after 30 days according to an exemplary embodiment of the present disclosure.

BMP-2 is a glycoprotein that is responsible for the differentiation of osteoblasts, thereby helping in bone formation.[87] It is known that the expression of BMP-2 is upregulated in hMSCs during osteogenic differentiation.[88,89] The expression is upregulated in both peptide scaffolds as well as in collagen and 2D, as shown in FIG. 37.

Figure 38:
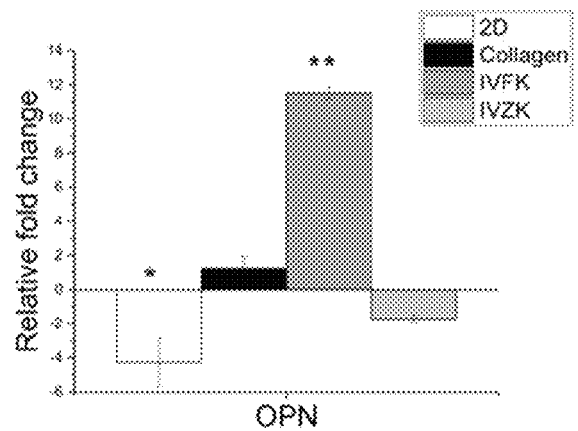
FIG. 38 illustrates OPN expression of BM-MSCs cultured on different scaffolds after 30 days according to an exemplary embodiment of the present disclosure.
Figure 39:
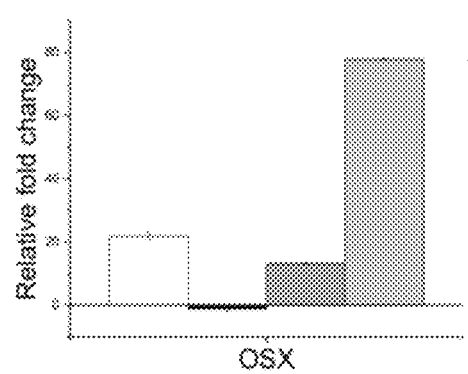
FIG. 39 illustrates OSX expression of BM-MSCs cultured on different scaffolds after 30 days according to an exemplary embodiment of the present disclosure.

OPN and IBSP are considered as late osteogenic markers, and their expression is known to be increased to induce osteoblast differentiation toward mature osteocyte.[90] Osteopontin (OPN) is one of the most plentiful non collagenous proteins in the bone. OPN plays an important role in differentiating osteoclasts and in recruiting and functioning osteoblasts.[91] OPN is also found to help in osteoclast migration toward sites of resorption and is essential for normal resorption and bone turnover.[92] The expression of this gene is measured and found to be downregulated in 2D and IVZK hydrogels. However, importantly, the expression of ONP is upregulated in cells cultured in IVFK as well as in collagen, which indicates the maturation of osteocyte, as shown in FIG. 38. In addition, the IBSP gene expression level is found to be the highest in the IVFK scaffold, as shown in FIG. 35. Finally, the expression level of OSX, which is decreased in the final maturation phase of osteogenic differentiation,[90] is low in IVFK compared to other groups and downregulated in cells cultured in collagen, as shown in FIG. 39. These findings dearly point to the osteogenic differentiation advantages offered by the IVFK peptide hydrogel.

Effect of Matrix Stiffness on Osteogenic Differentiation

Cells are sensitive to many factors, which may, in turn, affect their growth, maturation, and differentiation. These factors include chemical stimuli like growth factors and other factors.[93-96] Furthermore, the mechanical properties of the extracellular matrix, like rigidity, elastic modulus, and porosity, also have a significant impact.[97-99] Mechanical properties have been reported to have a substantial effect on regulating the stem cell fate.[100] For example, cells cultured inside hydrogel scaffolds with elastic moduli in ranges of 11-30 and 2.5-5 kPa directed MSC differentiation into osteogenic and adipogenic lineages, respectively.[101]

In one embodiment, the IVFK scaffold is selected to be used in the subsequent bone differentiation embodiments, based on the cell attachment, proliferation, and calcium deposition results obtained earlier. Therefore, osteogenic differentiation of BM-MSCs in IVFK hydrogels of different stiffnesses is evaluated using the alkaline phosphatase (ALP) activity assay, Alizarin red-S staining, and osteocalcin staining and by measurement of osteogenic transcription levels.

In one embodiment, the mechanical properties of the peptide hydrogel are tuned by adjusting the peptide concentration. However, caution should be administered as increasing the peptide concentration will affect the peptide hydrogel's physical parameters, such as porosity and diffusion of nutrients, affecting the cell viability and proliferation.[102-104]

Figure 40:
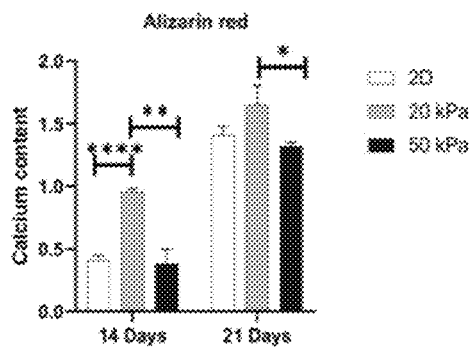
FIG. 40 illustrates the quantification of mineralization by Alizarin red-S of BM-MSCs cultured on scaffolds with different stiffnesses after 14 and 21 days of culture according to an exemplary embodiment of the present disclosure.
Figure 41:
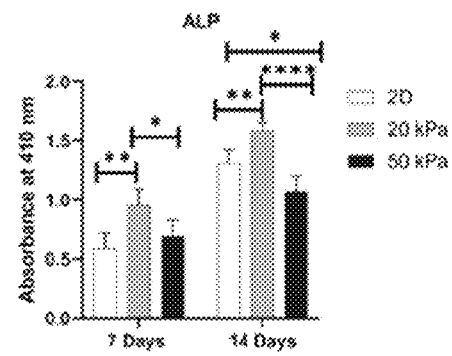
FIG. 41 illustrates the quantification of ALP activity of BM-MSCs cultured on scaffolds with different stiffnesses after 7 and 14 days according to an exemplary embodiment of the present disclosure.
Figure 42:
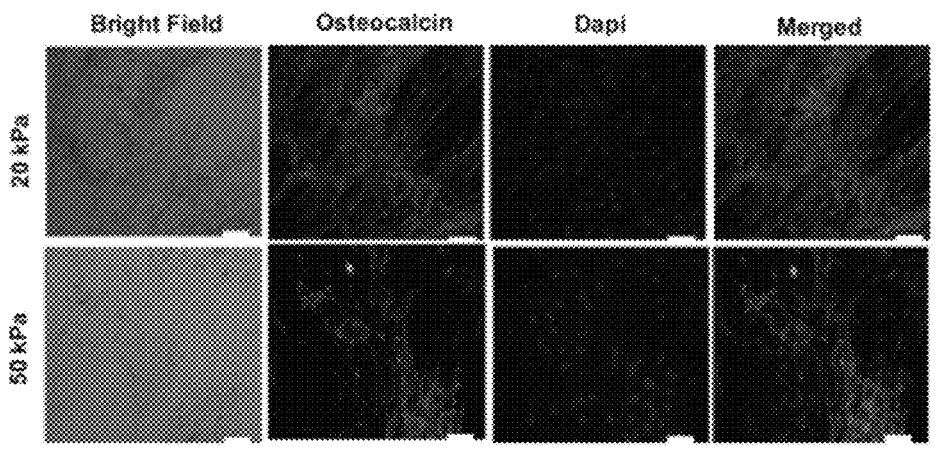
FIG. 42 shows the confocal images of osteocalcin produced by differentiated cells in different scaffolds according to an exemplary embodiment of the present disclosure.
Figure 43:
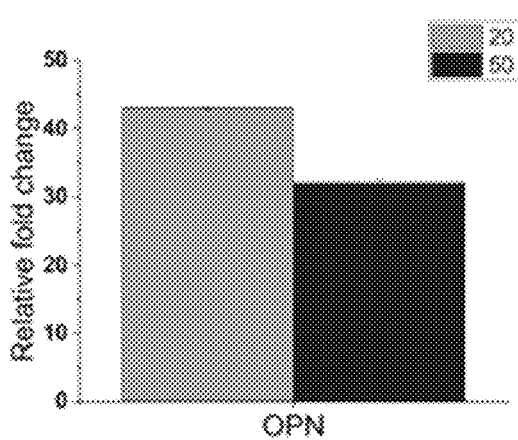
FIG. 43 illustrates OPN expression by RT-PCR of BM-MSCs cultured within scaffolds with different stiffnesses according to an exemplary embodiment of the present disclosure.
Figure 44:
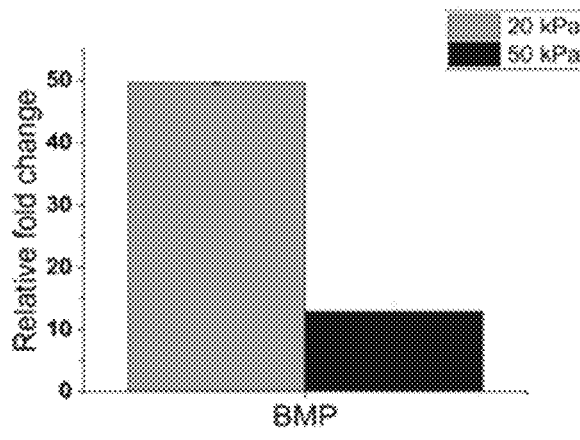
FIG. 44 illustrates BMP expression by RT-PCR of BM-MSCs cultured within scaffolds with different stiffnesses according to an exemplary embodiment of the present disclosure.

In one embodiment, to study the effect of peptide hydrogel stiffness on MSC differentiation, two concentrations of IVFK are investigated. In this embodiment, peptide concentrations of 4 and 8 mg/mL resulted in stiffnesses of around 20 and 50 kPa, respectively. Analyses of the calcium content and ALP release after 7 and 14 days, respectively, revealed that the value of the hydrogel with a storage modulus of around 20 kPa possessed a significantly higher calcium content than that at 50 kPa, as shown in FIG. 40 and higher ALP release than that at 50 kPa, as shown in FIG. 41. In FIGS. 40 and 41, statistical significance of * means $p<0.05$,  means $p<0.01$, and ** means $p<0.0001$. The osteocalcin expression is more intense in the 20 kPa scaffold compared to the others, as shown in FIG. 42. In FIG. 42, the cell nuclei are stained in blue using DAPI. Finally, the expression of two osteogenic genes, OPN (FIG. 43) and BMP-2 (FIG. 44) shows that the hydrogel with a reported stiffness of 20 kPa is able to support cell differentiation much better than the 50 kPa scaffold. This result is consistent with that of previous studies that reported that stiff matrices (16-25 kPa) lead MSCs to be differentiated to the osteoblast.[105,106] Also, another group reported that cells cultured inside a hydrogel with stiffness 11-30 kPa directed MSC differentiation into the osteogenic lineage.[101] The results suggest that matrix stiffness plays an important role in cell differentiation.

Angiogenesis Ability In Vitro

Figure 45:
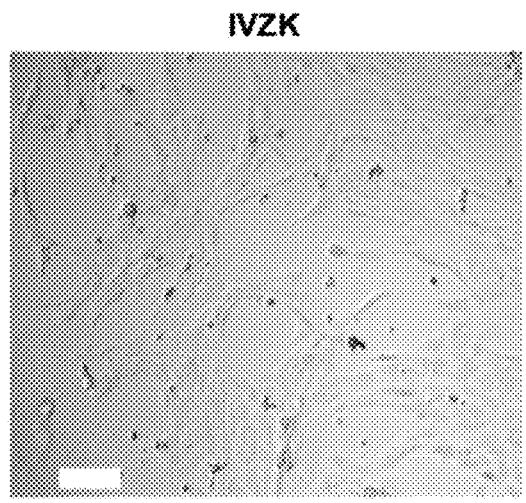
FIG. 45 shows the bright field image of HUVECs after 24 h culturing in IVZK scaffold according to an exemplary embodiment of the present disclosure.
Figure 46:
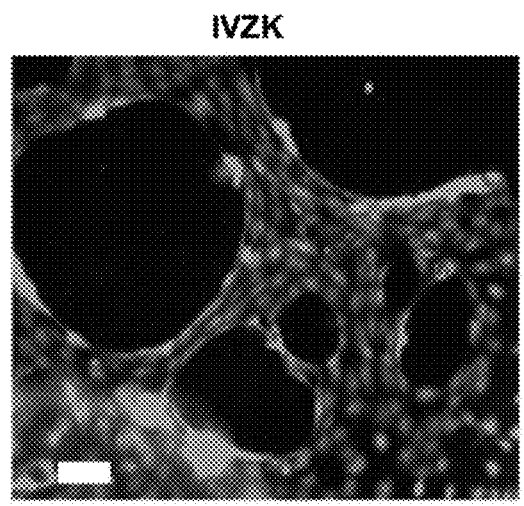
FIG. 46 shows the confocal image of HUVECs after 24 h culturing in IVZK scaffold according to an exemplary embodiment of the present disclosure.
Figure 47:
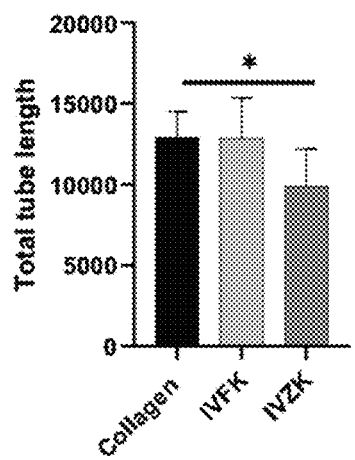
FIG. 47 illustrates the quantification of angiogenesis in IVZK scaffold by measuring total vessels length according to an exemplary embodiment of the present disclosure.
Figure 48:
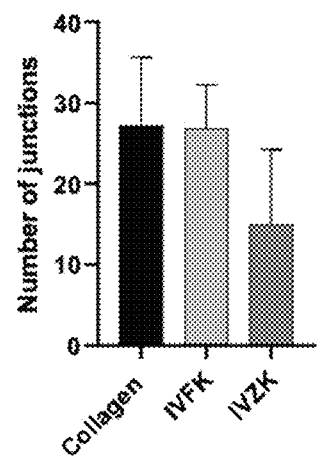
FIG. 48 illustrates the quantification of angiogenesis in IVZK scaffold by measuring vessels junctions according to an exemplary embodiment of the present disclosure.
Figure 49:
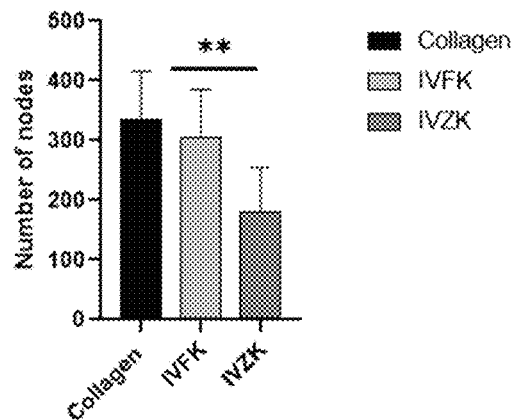
FIG. 49 illustrates the quantification of angiogenesis in IVZK scaffold by measuring number of nodes according to an exemplary embodiment of the present disclosure.
Figure 50:
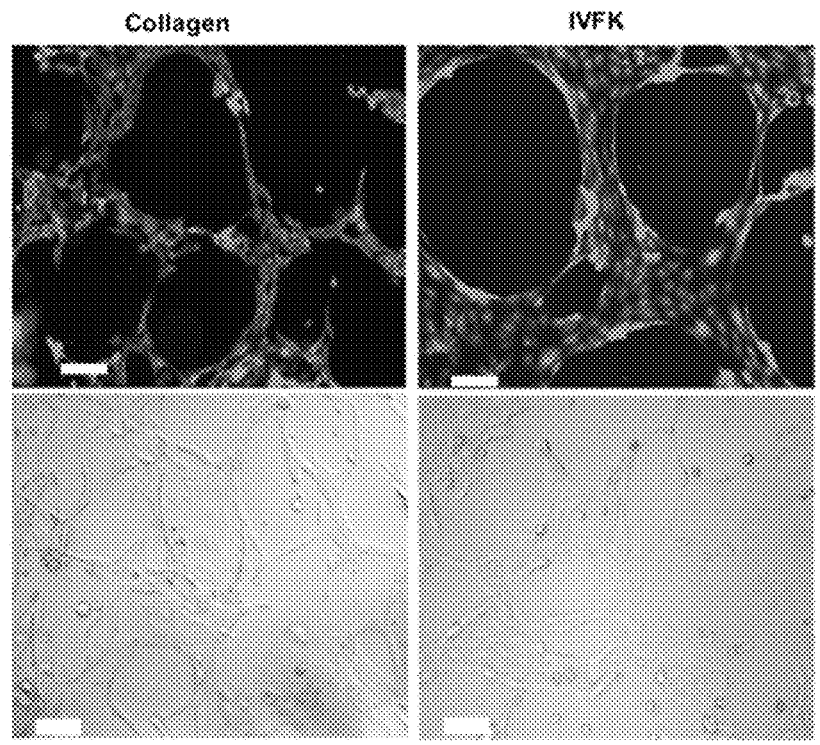
FIG. 50 shows the viability of HUVECs after 24 h culturing in IVFK scaffold according to an exemplary embodiment of the present disclosure.
Figure 51:
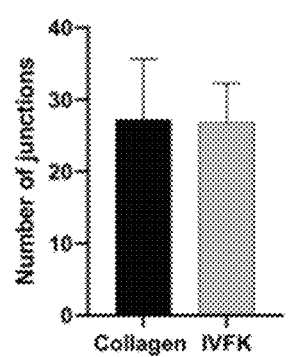
FIG. 51 illustrates the quantification of angiogenesis in IVFK scaffold by measuring vessels junctions according to an exemplary embodiment of the present disclosure.
Figure 52:
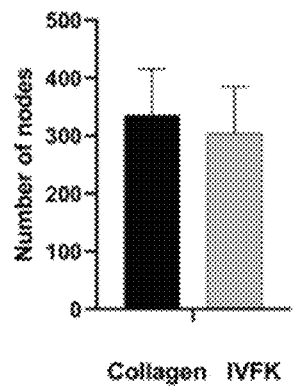
FIG. 52 illustrates the quantification of angiogenesis in IVFK scaffold by measuring number of nodes according to an exemplary embodiment of the present disclosure.
Figure 53:
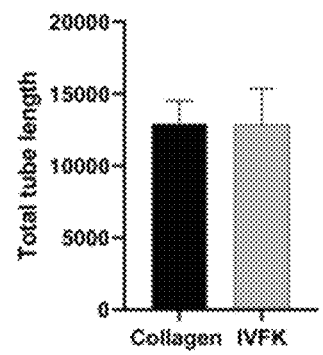
FIG. 53 illustrates the quantification of angiogenesis in IVFK scaffold by measuring total vessels length according to an exemplary embodiment of the present disclosure.

When bone deficiency occurs, it often causes blood vessel damage. Blood vessels provide the necessary components to repair the region of bone defects by transferring oxygen and nutrients.[107,108] In one embodiment, the capability of IVFK and IVZK hydrogels to support angiogenesis is also evaluated using HUVECs and compared with collagen, which is an essential component of the ECM and is known to support the angiogenesis of endothelial cells,[23] because the capillary system is a crucial component in bone regeneration. Viability of HUVECs in IVZK scaffold after culturing for 24 h can be observed the bright field image as shown in FIG. 45 and confocal images as shown in FIG. 46. In FIG. 46, live cells are stained in green by Calcein-AM, while dead cells are stained red by Ethidium homodimer. In FIGS. 45 and 46, the scale bar is 100 μm. Furthermore, the angiogenesis ability of IVZK scaffold is also measured by the vessels junctions (FIG. 48), number of nodes (FIG. 49) and, in total vessels length (FIG. 47) for 5 different microscopic pictures. After 24 h of culture, HUVECs cultured in IVFK scaffold forms dense network structures, which is similar to the collagen control, as shown in FIG. 50. In FIG. 50, the top row is confocal images, with live cells stained in green by Calcein-AM, and dead cells stained red by Ethidium homodimer, while the bottom row shows the bright field images. In FIG. 50, the scale bar is 100 μm. Additionally, the junctions (FIG. 51), nodes (FIG. 52), and the total length of tubes (FIG. 53) show no significant difference between IVFK and the collagen positive control. This result indicates that the IVFK scaffold has the ability to promote angiogenesis of HUVECs in vitro.

The present disclosure provides a method of the successful preparation of an ultrashort, amphiphilic peptide hydrogel capable of promoting osteogenic differentiation and angiogenesis and a 3D osteo-tissue graft using such peptide hydrogel. In contrast with the traditional 2D cell culture, cells maintained in a 3D culture more closely mimic the in vivo setting. This is particularly true with respect to cell shape and organization, as well as the extracellular environment, which may have a substantial impact on cell behavior. The present disclosure provides two peptide scaffold materials in supporting the adhesion, proliferation, and osteogenic differentiation of BM-MSCs. These hydrogels are easy to prepare and solidify quickly to provide a 3D environment. Furthermore, they have good mechanical properties, and they provide a well-defined molecule that can be adapted to include a wide range of chemical moieties. The fiber networks of the two hydrogels resemble that of the native ECM while providing adhesion and proliferation cues for the BM-MSCs. These hydrogels are biocompatible and promoted cell migration, osteogenic differentiation, and angiogenesis. Cells cultured in the IVFK hydrogel show an increase in ALP production, an enhanced expression of osteogenic markers, and mineralization. Furthermore, the mechanical properties of the hydrogel can be modulated by changing the peptide concentration, which can influence cell behavior as well. Thus, the presently disclosed hydrogel supports both osteogenic differentiation and angiogenesis and can be used as a scaffold in bone tissue engineering.

Having described the many embodiments of the present disclosure in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLES

Example 1

Materials

MBHA Rink Amide resin, 9-fluorenylmethoxycarbonyl (Fmoc), and N,N,N',N'-tetramethyl-O-(benzotriazol-1-yl) uronium tetrafluoroborate (TBTU), hydroxy benzotriazole (HOBt) were purchased from GL Biochem, China. Dimethylformamide (DMF), dichloromethane (DCM), N,N-diisopropylethylamine (DIPEA), piperidine, acetic anhydride, trifluoroacetic acid (TFA), triisopropylsilane, diethyl ether, and ethanol were purchased from Sigma-Aldrich®. The chemicals were used as received, without any purification.

Bone marrow-derived mesenchymal stem cells (BM-MSCs, PT-2501) were purchased from Lonza®, USA. Cells were cultured in medium (PT-4106E Lonza®, USA) and supplemented with mesenchymal cell growth supplements (PT-4106E Lonza®, USA), Gentamicin Sulfate Amphotericin-B (PT-4501E Lonza®, USA) and with L-Glutamine (PT-4107E Lonza®, USA). T175 or T75 cell culture flasks and 96 and 48 well-plates were ordered from Corning®, USA. The CellTiter-Glo® luminescent 3D cell viability assay and TRIzol™ reagent (Invitrogen® USA) ImProm-II™ Reverse Transcription System were purchased from Promega®, USA. APC anti-human CD105 Antibody 43A3 and PE anti-mouse CD73 Antibody TY/11.8 were from BioLegend™, UK. Anti-osteocalcin was purchased from (Abcam®, USA). Alexa® Fluor 488 (Invitrogen®, USA), ALP kit (Abcam®, UK). LIVE/DEAD Cell Viability Assay, Actin Cytoskeleton/Focal Adhesion Staining Kit were purchased from Thermo Fisher Scientific®, USA, and Merck®, Germany respectively. Alizarin red S dye was from Abcam®, USA.

Example 2

Peptide Synthesis

The peptide sequences Ac-Ile-Val-Phe-Lys-NH2 (IVFK) and Ac-Ile-Val-Cha-Lys-NH2 (IVZK) were synthesized using Fmoc-based solid-phase peptide synthesis (SPPS)[44] and purified using liquid chromatography-mass spectroscopy (LC-MS).

The rink amide resin (1 mmol) was pre-swollen in DCM for 30 min and the Fmoc-protecting group on the resin was then deprotected by 20% (v/v) piperidine/DMF prior to the first coupling of amino acid. Then, the resin was washed thoroughly with DMF and DCM. The peptide coupling was conducted on rink amide resin by adding a mixture of TBTU (3 eq.), HOBt (3 eq.) DIPEA (6 eq.), and Fmoc-protected amino acid (3 eq.) to the resin. Kaiser test was performed at the end of coupling step to confirm the attachment of amino acid. All the steps of Fmoc-deprotection, peptide coupling, washing and Kaiser test were repeated until all of the amino acids were added to the peptide sequence. The N-terminal of peptide sequence was later capped with acetyl group by adding a mixture of 2:6:1 (v/v) acetic anhydride:DIPEA:DMF. Then, the peptide was cleaved from the resin by agitating it in 95:2.5:2.5 mixture of TFA, water and triisopropylsilane, respectively for a minimum 2 hrs. The peptide in TFA solution was later collected in a round bottom flask. Afterwards, the peptide was precipitated by adding cold diethyl ether and kept standing overnight at 4° ° C. The precipitated peptide was separated from the supernatant by centrifugation and then dried under vacuum. This crude peptide was purified by reverse phase-HPLC purification using C-18 column (2-98% ACN in 10 min) at the flow rate of 20 mL/min.

Example 3

Hydrogel Formation and Characterization

The lyophilized peptide powders were dissolved in Milli-Q® water by vortexing into a clear solution at room temperature. Then, 10× phosphate-buffered saline (PBS) was added to the aqueous peptide solution at a final volume ratio of peptide solution to 10×PBS of 9:1. The vial inversion test was performed with different peptide concentrations to find the critical gelation concentration (CGC). To study the spatial structure of the peptide solution during the assembly process, two-dimensional (2D) NMR was performed using Bruker Avance III 600 MHz. Furthermore, scanning electron microscopy (SEM) was performed to visualize the morphology of the self-assembled nanofibers.

Example 4

1D NMR and 2D NMR in $D_2O$—$H_2O$

2D NMR of peptide solution was carried out to study the spatial structure during the assembly process. These NMR spectra were recorded on a Bruker Avance III 600 MHz equipped with a 5 mm Z-gradient SmartProbe BB(F)-H-D (BrukerBioSpin™, Rheinstetten, Germany). The samples were prepared from 10 mg of peptide in a mixture of 900 μL of 1mM 2,2-Dimethyl-2-silapentane-5-sulfonate (DSS) and 100 μL of $D_2O$. $^1$H-NMR was recorded by collecting 32 scans using excitation sculping with gradients pulse program (zgesgp) for water suppression. 109 COSY and TOCSY were then conducted to see the correlation between hydrogens that were coupled to each other. COSY was performed using a time domain of 4096 (F2)×512 (F1), 16 number of scans, a pulse program of cosydfgpph19, and 3-9-19 pulse sequence for water suppression.[110-112] For TOCSY, the parameters with time domain of 8192 (F2)×512 (F1), 16 number of scans, a pulse program of dipsi2gpph19, and 3-9-19 pulse sequence for water suppression were set. Finally, the NOESY acquisition was carried out with a time-domain size of 2048 (F2)×512 (F1), 32 scan numbers, a pulse program of noesyesgpph19, a mixing time of 400 ms, and water suppression using 3-9-19 pulse sequence. Broker Topspin 3.5p17 software was used in all NMR experiments for both data collection and spectral analyses.

Example 5

Scanning Electron Microscopy (SEM)

Peptide hydrogels were characterized using SEM to visualize the morphology of the nanofibers. In the absence of cells, 50 μL of both peptide hydrogels at low (4 mg/mL IVFK and 3 mg/mL IVZK) and high concentration (8 mg/mL for both peptides) were prepared on 18×18 mm glass coverslips and left to solidify for 10-20 minutes post-formation. At this point, the hydrogel samples were dehydrated by gradually immersing in increasing concentrations of 20%, 40%, 60%, 80%, and 100% (v/v) ethanol solutions for 5 min in each ethanol solution. Further dehydration in 100% ethanol solution was done for 2 hours. The dehydrated samples were subsequently placed into a critical point dryer for evaporation before being mounted onto aluminum SEM pin stubs with double-stick conductive carbon tape. A final sputter coating of 10 nm of Iridium (Ir) was performed prior to imaging with FEI Magellan XHR. The porosity of the peptide matrix was analyzed using thresholding technique in ImageJ.

SEM was also used to determine the cell-matrix interaction. First, the cells encapsulated in hydrogels were fixed in 2.5% glutaraldehyde for overnight (4° C.) and then washed using PBS. The samples were subsequently incubated in 1% osmium tetroxide for one hour and washed with water. Afterwards, the dehydration was done by immersing them in increasing concentrations of ethanol: 30, 50, 70, 90 and 100%, 15 min each step. Then, the samples were processed in critical point dryer. The dried samples were then mounted and coated with 5 nm Ir thickness.

Example 6

Liquid Chromatography-Mass Spectroscopy (LC-MS)

1 mg of peptides, which were dissolved in 1 mL of water were analyzed using Agilent 1260 Infinity LC equipped with Agilent 6130 Quadrupole MS. Agilent Zorbax SB-C18 4.6×250 mm column was used together with a mixture of two different solutions of 0.1% (v/v) formic acid—water (A) and 0.1% (v/v) formic acid—acetonitrile (B). The flow of mobile phase was 1.5 ml/min with a composition of 98% A—2% B at first 1 min. From 1 to 18 mins, the flow of B increased until 98% B and turned back again to 2% again. LC chromatogram was obtained at wavelength of 220 nm. The molecular weight of the peptides was confirmed in positive mode polarity.

Example 7

Mechanical Characterization of Hydrogel Stiffness

The oscillatory rheological test was performed to determine the mechanical properties of the peptide hydrogels. The peptide hydrogels were measured on a TA Ares G2 rheometer with an 8 mm parallel-plate geometry and a 1.5 mm gap distance at a temperature of 22° C. All of the hydrogels were made inside a Sigmacote®-coated glass ring with 9 mm inner diameter 19 h prior to measurement. Six replicates with a volume of 150 μL were prepared for each sample. The measurement was performed for 5 min with constant angular frequency and strain at 1 Hz and 0.1%.

Example 8

Cell Culture of Human Bone Marrow Mesenchymal Stem Cells

Cells were cultured in a medium and supplemented with mesenchymal cell growth supplements. The cells were maintained in either a T75 or a T150 cell culture flask at 37° C. in a humidified incubator with 95% air and 5% $CO_2$. The cells were subcultured when cells reached approximately 80% confluency by trypsin. The culture medium was changed every 2-3 days.

Example 9

Characterization and Preparation of 3D Culture of Human-Bone-Marrow-Derived Mesenchymal Stem Cells (hBM-MSCs)

The hBM-MSCs were cultured in T75 flasks and incubated in a $CO_2$ incubator maintained at 37° ° C. with 5% $CO_2$. Culture media were replaced every 2-3 days until the cells reached 80% confluency. Confluent cells were trypsinized and subcultured, and cells at passage 3-6 were used for the study. For the 3D culture, different peptides were sterilized by exposure to UV light for 30 min. Then, 200 μL of 3D constructs in the 48-well plate was formed by mixing the peptide solution (IVZK=3 mg/mL (5.42 mM); IVFK=4 mg/mL (7.31 mM)) with 40,000 cells suspended in 2×PBS. Culture plates were incubated for 5 min at 37° C., and the complete medium was added carefully to the culture plates. The constructs were then cultured with osteogenic induction media or basal stem cell growth media. The morphology, cell proliferation, and mineralization of the cells in each scaffold were analyzed and compared. The efficiency of osteogenic differentiation was also compared with a traditional 2D culture. As positive controls, cells cultured in a collagen scaffold were used because Matrigel degrades after 2 weeks due to which we cannot keep it for the entire differentiation time (3-4 weeks). Also, collagen is considered as a positive 3D scaffold in osteogenic differentiation. The negative control was the cell from the same passage grown in a basal medium without osteogenic supplements. Alamar Blue and CellTiter-Glo® luminescent 3D cell viability assays were performed to evaluate the cytotoxicity and proliferation of cells. Flow cytometry was performed to study the expression of stem cell markers.

Example 10

Alamar Blue

A volume of 10 μL of Alamar blue stock solution was added to 100 μL of media in each well. Plates were incubated at 37° C. for 4 h. The fluorescence was measured at an excitation wavelength of 530 nm, and the emission at 590 nm. The viability percentage was calculated against the control (2D).

Example 11

Live/Dead Assay

The viability of the cells within different scaffolds (IVFK 3 mg/ml and IVZK 4 mg/ml) were tested using live/dead staining, in which, calcein acetoxymethyl ester (Calcein-AM) is used to detect viable cells and ethidium homodimer-I (EthD-I) is used to detect dead cells. 3D constructs were washed twice with PBS. Then a staining solution of 2 μM of Calcein-AM and 4 μM of EthD-1 were added to each well and incubated for 30 minutes at room temperature. After the incubation period, the staining solution was discarded, and 1×DPBS was added to each well before imaging. Stained cells were imaged with an inverted confocal microscope (Zeiss™ LSM 710 Inverted Confocal Microscope, Germany).

Example 12

3D Cell Proliferation Assay

The CellTiter-Glo® luminescent 3D cell viability assay was used to determine the proliferation of cells in 3D hydrogels based on the presence of ATP, as a product produced from metabolically active cells.[113] After each time point, the kit was equilibrated at room temperature for approximately 30 minutes. CellTiter-Glo® Reagent equal to the cell culture medium existing volume in each well was added. The contents were mixed for 5 minutes to digest the hydrogels and then incubated for 30 minutes at room temperature. After incubation, the luminescence was recorded using a plate reader (PHERAstar® FS, Germany).

Example 13

Flow Cytometry

The cells were cultured in different peptide scaffolds as described above. After 3 days of culture, the gels were transferred into a 15 mL centrifuge tube, 10 mL of PBS was added, and the hydrogels were mechanically disrupted by gently pipetting the mixture. Then the tube was centrifuged at 1,000×g for 5 min, and the supernatant was discarded. The cells were resuspended in 0.5 mL of Cell Staining Buffer including 5 μL of the following conjugated monoclonal antibody, APC anti-human CD105 Antibody, 43A3 and PE anti-human CD73 Antibody. The cells were incubating in the dark for 15 min with combinations of the monoclonal antibodies described above. Unstained hMSC was used as a control.

Example 14

Cell Invasion Assay

A previous cell invasion assay protocol was followed.[50] Briefly, cells (30,000) were added to 2 μL of fibrin solution (2 mg/mL fibrinogen and 2.5 U/mL thrombin). The dusters were incubated for 30 min at 37° C. for polymerization. Then, dusters were transferred into a peptide gel (20 itL) by placing them inside the gel. The gel was made by mixing 10 μL of peptide solution and 10 μL of PBS 2× and incubated for 15 min for solidification. Cells were imaged to quantify cell migration out of the fibrin clot.

Example 15

Cytoskeletal and Antiosteocalcin Staining

Immunostaining was performed after each time point of culture. Briefly, cells were fixed by 4% paraformaldehyde solution for 30 min and incubated in a cold cytoskeleton buffer (3 mM $MgCl_2$, 300 mM sucrose, and 0.5% Triton X-100 in PBS solution) for 5 min to permeabilize the membranes of the cells. The permeabilized cells were incubated in a blocking buffer solution, 5% fetal bovine serum (FBS), 0.1% Tween-20, and 0.02% sodium nide in PBS for 30 min. For antiosteocalcin, the dye was diluted in PBS (1:80) and incubated for 1 h at room temperature, followed by incubation with a secondary antibody conjugated with Alexa Fluor 488, 1:500 (green). For F-actin, rhodamine-phalloidin (1:300) was added to the cells for 1 h. Further, the cells were incubated in 4',6-diamidino-2-phenyfindole (DAPI) for 5 min to counterstain the nucleus. The fluorescent-dye-treated cells were observed and imaged using a laser scanning confocal microscope (Zeiss™ LSM 710 inverted confocal microscope, Germany).

Example 16

Alkaline Phosphatase Assay

Alkaline phosphatase (ALP) was measured after 1 and 2 weeks of culture using an alkaline phosphatase substrate kit. At the end of each culture time, the scaffolds were washed by PBS and cells were lysed using 1% Triton X-100. Then, 80 μL of the cell lysate mixture was added to 50 μL of the para-nitrophenylphosphate (pNPP) substrate (5 mM) and incubated at room temperature for 2 h. The reaction was inhibited by the addition of a stop solution, and the absorbance was measured at 405 nm using a multimode plate reader (PHERAstar® FS, Germany).

Example 17

Alizarin Red Staining

After 14 days of culture, the media were removed and the cells were washed three times with PBS, fixed with 4% paraformaldehyde, and incubated for 15 min at room temperature.

After 14 days of culture, the media was removed and then, the cells were washed three times with PBS and then fixed with 4% paraformaldehyde and the cells incubated for 15 minutes at room temperature. Then, the cells were washed three times with Milli-Q® water. Then the Milli-Q® water was removed and 1 mL of 40 mM Alizarin Red Staining (pH=4.2) was added to each well. The scaffolds were incubated at room temperature for 20-30 min with gentle shaking. Finally, the wells were washed five times with Milli-Q® water and imaged using an inverted microscope (Leica® DM1300M). For the quantification of Alizarin Red Staining, 100 µL of 10% acetic acid was added to each well in a 48-well plate and incubated at room temperature for 30 minutes with gentle shaking. The samples were transferred into a 1.5 mL microcentrifuge tube, and the tubes were vortexed for 30 seconds. The samples were heated at 85° C. for 10 minutes and sealed with parafilm to avoid evaporation. The tubes were then incubated on ice for 5 minutes and then centrifuged at 20,000 g for 15 minutes. After that, 50 µL of 10% ammonium hydroxide was added to neutralize the acidic environment. Finally, 50 µL of each tube was transferred to a 96-well plate, and the absorbance at 405 nm was read with a plate reader (PHERAstar® FS, Germany)

Example 18

Quantitative Real-Time Polymerase Chain Reaction (RT-PCR)

The BM-MSCs were cultured on different scaffolds with an osteogenic medium for 4 weeks. Total RNA was extracted using the TRIzol™ reagent. RNA concentration and purity were measured using a NanoDrop® 8000 spectrophotometer (Thermo Fisher®). Complementary DNA (cDNA) was synthesized using the ImProm-II Reverse Transcription System. Primer sequences were taken from previously published studies and are summarized in below. Relative quantification was performed using the comparative CT ($2-\Delta\Delta CT$) and normalized against glyceraldehyde 3-phosphate dehydrogenase (GAPDH), which was used as a housekeeping gene to calculate the fold change in gene expression. BM-MSCs on a 2D culture using basal media were used as controls.

Primers Used to Modify Bone-Specific Genes:

| Gene | Direction | Sequence | |
|---|---|---|---|
| ALP | forward | 5-GCACCTGCCTTACTAACTC-3 | (SEQ ID NO. 1) |
|  | reverse | 5-AGACACCCATCCCATCTC-3 | (SEQ ID NO. 2) |
| IBSP | F | CACTGGAGCCAATGCAGAAGA | (SEQ ID NO. 3) |
|  | R | TGGTGGGGTTGTAGGTTCAA | (SEQ ID NO. 4) |
| BMP-2 | F | 5-TGCGGTCTCCTAAAGGTC-3 | (SEQ ID NO. 5) |
|  | R | 5-AACTCGAACTCGCTCAGG-3 | (SEQ ID NO. 6) |
| RUNX2 | F | TCAACGATCTGAGATTTGTGGG | (SEQ ID NO. 7) |
|  | R | GGGGAGGATTTGTGAAGACGG | (SEQ ID NO. 8) |
| osteopontin | F | GAAGTTTCGCAGACCTGACAT | (SEQ ID NO. 9) |
|  | R | GTATGCACCATTCAACTCCTCG | (SEQ ID NO. 10) |

Example 19

In Vitro Angiogenesis Study

Peptide hydrogel or collagen was placed in a 24-well plate, and human umbilical vein endothelial cells (HUVECs) at 40,000 cells/well were added on top of the peptide gel or collagen. Cells were cultured in endothelial growth media for 24 h. Cells were then investigated using an inverted microscope, and images were analyzed by ImageJ using the Angiogenesis Analyzer.

Example 20

Statistical Analysis

Results are represented as mean±standard deviation (SD), n≥3. The differences observed in the BM-MSC behavior between different scaffolds were compared; statistical analysis was performed using a Student t-test, and values with $p<0.05$ were considered to be statistically significant.

REFERENCES

The following references are referred to above and are incorporated herein by reference:

1. Gauthaman, K.; Venugopal, J. R.; Yee, F. C.; Biswas, A.; Ramakrishna, S.; Bongso, A. Osteogenic differentiation of human Wharton's jelly stem cells on nanofibrous substrates in vitro. *Tissue Eng., Part A* 2011, 17, 71-81.
2. Leng, Q.; Chen, L.; Lv, Y. RNA-based scaffolds for bone regeneration: application and mechanisms of mRNA, miRNA and siRNA. *Theranostics* 2020, 10, 3190.
3. Erdem, A.; Darabi, M. A.; Nasiri, R.; Sangabathuni, S.; Ertas, Y. N.; Alem, H.; Hosseini, V.; Shamloo, A.; Nasr, A. S.; Ahadian, S. 3D Bioprinting of Oxygenated Cell-Laden Gelatin Methacryloyl Con-structs. *Adv. Healthcare Mater.* 2020, 9, No. 1901794.
4. Myeroff, C.; Archdeacon, M. Autogenous bone graft: donor sites and techniques. *J. Bone Jt. Surg.* 2011, 93, 2227-2236.
5. Silbernagel, N.; Körner, A.; Balitzki, J.; Jaggy, M.; Bertels, S.; Richter, B.; Hippler, M.; Hellwig, A.; Hecker, M.; Bastmeyer, M.; Ullrich, N. D. Shaping the Heart: Structural and Functional Maturation of iPSC-Cardiomyocytes in 3D-Micro-Scaffolds. *Bio-materials* 2020, 227, No. 119551.
6. Silber, J. S.; Anderson, D. G.; Daffner, S. D.; Brislin, B. T.; Leland, J. M.; Hilibrand, A. S.; Vaccaro, A. R.; Albert, T. J. Donor site morbidity after anterior iliac crest bone harvest for single-level anterior cervical discectomy and fusion. *Spine* 2003, 28, 134-139.
7. Alonzo, M.; Alvarez Primo, F.; Anil Kumar, S.; Mudloff, J. A.; Dominguez, E.; Fregoso, G.; Ortiz, N.; Weiss, W. M.; Joddar, B. Bone tissue engineering techniques, advances, and scaffolds for treatment of bone defects. *Curr. Opin. Biomed. Eng.* 2021, 17, No. 100248.
8. Amini, A. R.; Laurencin, C. T.; Nukavarapu, S. P. Bone tissue engineering: recent advances and challenges. *Crit. Rev. Biomed. Eng.* 2012, 40, 363-408.
9. Bharadwaz, A.; Jayasuriya, A. C. Recent trends in the application of widely used natural and synthetic polymer nanocomposites in bone tissue regeneration. *Mater. Sci. Eng., C* 2020, 110, No. 110698.
10. Pittenger, M. F.; Mackay, A. M.; Beck, S. C.; Jaiswal, R. K.; Douglas, R.; Mosca, J. D.; Moorman, M. A.; Simonetti, D. W.; Craig, S.; Marshak, D. R. Multilineage potential of adult human mesenchymal stem cells. *Science* 1999, 284, 143-147.
11. Ma, K.; Laco, F.; Ramakrishna, S.; Liao, S.; Chan, C. K. Differentiation of bone marrow-derived mesenchymal stem cells into multi-layered epidermis-like cells in 3D organotypic coculture. *Biomaterials* 2009, 30, 3251-3258.

12. Petite, H.; Viateau, V.; Bensaid, W.; Meunier, A.; de Pollak, C.; Bourguignon, M.; Oudina, K.; Sedel, L.; Guillemin, G. Tissue-engineered bone regeneration. *Nat. Biotechnol.* 2000, 18, 959.
13. Takamine, Y.; Tsuchiya, H.; Kitakoji, T.; Kurita, K.; Ono, Y.; Ohshima, Y.; Kitoh, H.; Ishiguro, N.; Iwata, H. Distraction osteogenesis enhanced by osteoblastlike cells and collagen gel. *Clin. Orthop. Relat. Res.* 2002, 399, 240-246.
14. Kofidis, T.; Lebl, D. R.; Martinez, E. C.; Hoyt, G.; Tanaka, M.; Robbins, R. C. Novel injectable bioartificial tissue facilitates targeted, less invasive, large-scale tissue restoration on the beating heart after myocardial injury. *Circulation* 2005, 112, I-173-I-177.
15. Yildirim, Y.; Naito, H.; Didie, M.; Karikkineth, B. C.; Biermann, D.; Eschenhagen, T.; Zimmermann, W.-H. Development of a biological ventricular assist device: preliminary data from a small animal model. *Circulation* 2007, 116, I-16-I-23.
16. Radisic, M.; Park, H.; Shing, H.; Consi, T.; Schoen, F. J.; Langer, R.; Freed, L. E.; Vunjak-Novakovic, G. Functional assembly of engineered myocardium by electrical stimulation of cardiac myocytes cultured on scaffolds. *Proc. Natl. Acad. Sci. U.S.A.* 2004, 101, 18129-18134.
17. Spadaccio, C.; Chachques, E.; Chello, M.; Covino, E.; Chachques, J. C.; Genovese, J. Predifferentiated adult stem cells and matrices for cardiac cell therapy. *Asian Cardiovasc. Thorac. Ann.* 2010, 18, 79-87.
18. Kutschka, I.; Chen, I. Y.; Kofidis, T.; Arai, T.; Von Degenfeld, G.; Sheikh, A. Y.; Hendry, S. L.; Pearl, J.; Hoyt, G.; Sista, R.; et al. Collagen matrices enhance survival of transplanted cardiomyoblasts and contribute to functional improvement of ischemic rat hearts. *Circulation* 2006, 114, I-167-I-173.
19. Orkin, R.; Gehron, P.; Mcgoodwin, E. B.; Martin, G.; Valentine, T.; Swarm, R. A murine tumor producing a matrix of basement membrane. *J. Exp. Med.* 1977, 145, 204-220.
20. Sethi, T.; Rintoul, R. C.; Moore, S. M.; Mackinnon, A. C.; Salter, D.; Choo, C.; Chilvers, E. R.; Dransfield, I.; Donnelly, S. C.; Strieter, R.; et al. Extracellular matrix proteins protect small cell lung cancer cells against apoptosis: a mechanism for small cell lung cancer growth and drug resistance in vivo. *Nat. Med.* 1999, 5, 662-668.
21. Grant, D.; Kibbey, M.; Kinsella, J.; Cid, M.; Kleinman, H. The role of basement membrane in angiogenesis and tumor growth. *Pathol., Res. Pract.* 1994, 190, 854-863.
22. Fushimi, H.; Hiratsuka, T.; Okamura, A.; Ono, Y.; Ogura, I.; Nishimura, I. Recombinant collagen polypeptide as a versatile bone graft biomaterial. *Commun. Mater.* 2020, 1, No. 1.
23. Kang, P. L.; Huang, H. H.; Chen, T.; Ju, K. C.; Kuo, S. M. Angiogenesis-promoting effect of LIPUS on hADSCs and HUVECs cultured on collagen/hyaluronan scaffolds. *Mater. Sci. Eng., C* 2019, 102, 22-33.
24. Blokhuis, T.; Arts, J. C. Bioactive and osteoinductive bone graft substitutes: definitions, facts and myths. *Injury* 2011, 42, S26-S29.
25. Barradas, A.; Yuan, H.; van Blitterswijk, C. A.; Habibovic, P. Osteoinductive biomaterials: current knowledge of properties, experimental models and biological mechanisms. *Eur. Cells Mater.* 2011, 21, 407-429.
26. Habibovic, P.; de Groot, K. Osteoinductive biomaterials· properties and relevance in bone repair. *J. Tissue Eng. Regener. Med.* 2007, 1, 25-32.
27. Ramier, J.; Grande, D.; Bouderlique, T.; Stoilova, O.; Manolova, N.; Rashkov, I.; Langlois, V.; Albanese, P.; Renard, E. From design of bio-based biocomposite electrospun scaffolds to osteogenic differentiation of human mesenchymal stromal cells. *J. Mater. Sci. Mater. Med.* 2014, 25, 1563-1575.
28. Adler-Abramovich, L.; Gazit, E. The physical properties of supramolecular peptide assemblies: from building block association to technological applications. *Chem. Soc. Rev.* 2014, 43, 6881-6893.
29. Biesalski, M. A.; Knaebel, A.; Tu, R.; Tirrell, M. Cell adhesion on a polymerized peptide-amphiphile monolayer. *Biomaterials* 2006, 27, 1259-1269.
30. Mata, A.; Hsu, L.; Capito, R.; Aparicio, C.; Henrikson, K.; Stupp, S. I. Micropatterning of bioactive self-assembling gels. *Soft Matter* 2009, 5, 1228-1236.
31. Eren, E. D.; Tansik, G.; Tekinay, A. B.; Guler, M. O. Mineralized peptide nanofiber gels for enhanced osteogenic differentiation. *ChemNanoMat* 2018, 4, 837-845.
32. Mata, A.; Geng, Y.; Henrikson, K. J.; Aparicio, C.; Stock, S. R.; Satcher, R. L.; Stupp, S. I. Bone regeneration mediated by biomimetic mineralization of a nanofiber matrix. *Biomaterials* 2010, 31, 6004-6012.
33. Derkus, B.; Okesola, B. O.; Barrett, D. W.; D'Este, M.; Chowdhury, T. T.; Eglin, D.; Mata, A. Multicomponent hydrogels for the formation of vascularized bone-like constructs in vitro. *Acta Biomater.* 2020, 109, 82-94.
34. Ghosh, M.; Halperin-Sternfeld, M.; Grigoriants, I.; Lee, J.; Nam, K. T.; Adler-Abramovich, L. Arginine-presenting peptide hydrogels decorated with hydroxyapatite as biomimetic scaffolds for bone regeneration. *Biomacromolecules* 2017, 18, 3541-3550.
35. Tsutsumi, H.; Kawamura, M.; Mihara, H. Osteoblastic differentiation on hydrogels fabricated from Ca2+-responsive self-assembling peptides functionalized with bioactive peptides. *Bioorg. Med. Chem.* 2018, 26, 3126-3132.
36. Zhang, R.; Liu, Y.; Qi, Y.; Zhao, Y.; Nie, G.; Wang, X.; Zheng, S. Self-assembled peptide hydrogel scaffolds with VEGF and BMP-2 Enhanced in vitro angiogenesis and osteogenesis. *Oral Dis.* 2021, DOI: 10.1111/odi. 13785, in press.
37. Misawa, H.; Kobayashi, N.; Soto-Gutierrez, A.; Chen, Y.; Yoshida, A.; Rivas-Carrillo, J. D.; Navarro-Alvarez, N.; Tanaka, K.; Miki, A.; Takei, J.; et al. PuraMatrix facilitates bone regeneration in bone defects of calvaria in mice. *Cell Transplant.* 2006, 15, 903-910.
38. Ikeno, M.; Hibi, H.; Kinoshita, K.; Hattori, H.; Ueda, M. Effects of self-assembling peptide hydrogel scaffold on bone regeneration with recombinant human bone morphogenetic protein-2. *Int. J. Oral Maxillofac. Implants* 2013, 28, e283-9.
39. He, B.; Ou, Y.; Chen, S.; Zhao, W.; Zhou, A.; Zhao, J.; Li, H.; Jiang, D.; Zhu, Y. Designer bFGF-incorporated d-form self-assembly peptide nanofiber scaffolds to promote bone repair. *Mater. Sci. Eng., C* 2017, 74, 451-458.
40. Tsukamoto, J.; Naruse, K.; Nagai, Y.; Kan, S.; Nakamura, N.; Hata, M.; Omi, M.; Hayashi, T.; Kawai, T.; Matsubara, T. Efficacy of a self-assembling peptide hydrogel, SPG-178-gel, for bone regeneration and three-dimensional osteogenic induction of dental pulp stem cells. *Tissue Eng., Part A* 2017, 23, 1394-1402.
41. Sun, Y.; Li, W.; Wu, X.; Zhang, N.; Zhang, Y.; Ouyang, S.; Song, X.; Fang, X.; Seeram, R.; Xue, W.; He, L.; Wu, W. Functional Self-Assembling Peptide Nanofiber Hydrogels Designed for Nerve Degeneration. *ACS Appl. Mater. Interfaces* 2016, 8, 2348-2359.
42. Guo, J.; Su, H.; Zeng, Y.; Liang, Y.-X.; Wong, W. M.; Ellis-Behnke, R. G.; So, K.-F.; Wu, W. Reknitting the injured spinal cord by self-assembling peptide nanofiber scaffold. *Nanomedicine* 2007, 3, 311-321.
43. Liu, X.; Wang, X.; Wang, X.; Ren, H.; He, J.; Qiao, L.; Cui, F.-Z. Functionalized self-assembling peptide nanofiber hydrogels mimic stem cell niche to control human adipose stem cell behavior in vitro. *Acta Biomater.* 2013, 9, 6798-6805.
44. Rauf, S.; Susapto, H. H.; Kahin, K.; Alshehri, S.; Abdelrahman, S.; Lam, J. H.; Asad, S.; Jadhav, S.; Sundaramurthi, D.; Gao, X.; Hauser, C. A. E. Self-assembling tetrameric peptides allow in situ 3D bioprinting under physiological conditions. *J. Mater. Chem. B* 2021, 9, 1069-1081.
45. Susapto, H. H.; Alhattab, D.; Abdelrahman, S.; Khan, Z.; Alshehri, S.; Kahin, K.; Ge, R.; Moretti, M.; Emwas, A.-H.; Hauser, C. A. E. Ultrashort Peptide Bioinks Support Automated Printing of Large-Scale Constructs Assuring Long-Term Survival of Printed Tissue Constructs. *Nano Lett.* 2021, 21, 2719-2729.
46. Arthur, A.; Zannettino, A.; Gronthos, S. The therapeutic applications of multipotential mesenchymal/stromal stem cells in skeletal tissue repair. *J. Cell. Physiol.* 2009, 218, 237-245.
47. Polo-Corrales, L.; Latorre-Esteves, M.; Ramirez-Vick, J. E. Scaffold design for bone regeneration. *J. Nanosci. Nanotechnol.* 2014, 14, 15-56.
48. Holmes, T. C. Novel peptide-based biomaterial scaffolds for tissue engineering. *Trends Biotechnol.* 2002, 20, 16-21.
49. Hauser, C. A.; Deng, R.; Mishra, A.; Loo, Y.; Khoe, U.; Zhuang, F.; Cheong, D. W.; Accardo, A.; Sullivan, M. B.; Riekel, C.; Ying, J. Y.; Hauser, U. A. Natural tri- to hexapeptides self-assemble in water to amyloid beta-type fiber aggregates by unexpected alpha-helical intermediate structures. *Proc. Natl. Acad. Sci. U.S.A.* 2011, 108, 1361-1366.
50. Lei, Y.; Gojgini, S.; Lam, J.; Segura, T. The spreading, migration and proliferation of mouse mesenchymal stem cells cultured inside hyaluronic acid hydrogels. *Biomaterials* 2011, 32, 39-47.
51. Loo, Y.; Chan, Y. S.; Szczerbinska, I.; Tan, B. C.; Wan, A. C.; Ng, H. H.; Hauser, C. A. A Chemically Well-Defined, Self-Assembling 3D Substrate for Long-Term Culture of Human Pluripotent Stem Cells. *ACS Appl. Bio Mater.* 2019, 2, 1406-1412.
52. Lee, J. H.; Jung, H. W.; Kang, I.-K.; Lee, H. B. Cell behaviour on polymer surfaces with different functional groups. *Biomaterials* 1994, 15, 705-711.
53. Guo, S.; Zhu, X.; Li, M.; Shi, L.; Ong, J. L. T.; Janczewski, D.; Neoh, K. G. Parallel Control over Surface Charge and Wettability Using Polyelectrolyte Architecture: Effect on Protein Adsorption and Cell Adhesion. *ACS Appl. Mater. Interfaces* 2016, 8, 30552-30563.
54. Hauser, C. A. E.; Zhang, S. Designer self-assembling peptide nanofiber biological materials. *Chem. Soc. Rev.* 2010, 39, 2780-2790.
55. Bowerman, C. J.; Ryan, D. M.; Nissan, D. A.; Nilsson, B. L. The Effect of Increasing Hydrophobicity on the Self-Assembly of Amphipathic β-Sheet Peptides. *Mol. Biosyst.* 2009, 5, 1058-1069.
56. Susapto, H. H.; Alhattab, D.; Abdelrahman, S.; Khan, Z.; Alshehri, S.; Kahin, K.; Ge, R.; Moretti, M.; Emwas, A. H.; Hauser, C. A. E. Ultrashort Peptide Bioinks Support Automated Printing of Large-Scale Constructs Assuring Long-Term Survival of Printed Tissue Constructs. *Nano Lett.* 2021, 2719.
57. Friedrichs, J.; Taubenberger, A.; Franz, C. M.; Muller, D. J. Cellular Remodelling of Individual Collagen Fibrils Visualized by Time-lapse AFM. *J. Mol. Biol.* 2007, 372, 594-607.
58. Nakayama, M.; Amano, M.; Katsumi, A.; Kaneko, T.; Kawabata, S.; Takefuji, M.; Kaibuchi, K. Rho-kinase and myosin II activities are required for cell type and environment specific migration. *Genes Cells* 2005, 10, 107-117.
59. Beadle, C.; Assanah, M. C.; Monzo, P.; Vallee, R.; Rosenfeld, S. S.; Canoll, P. The Role of Myosin II in Glioma Invasion of the Brain. *Mol. Biol. Cell* 2008, 19, 3357-3368.
60. Friedl, P.; Wolf, K.; Lammerding, J. Nuclear mechanics during cell migration. *Curr. Opin. Cell Biol.* 2011, 23, 55-64.
61. Balzer, E. M.; Tong, Z.; Paul, C. D.; Hung, W.-C.; Stroka, K. M.; Boggs, A. E.; Martin, S. S.; Konstantopoulos, K. Physical confinement alters tumor cell adhesion and migration phenotypes. *FASEB J.* 2012, 26, 4045-4056.
62. Khatau, S. B.; Bloom, R. J.; Bajpai, S.; Razafsky, D.; Zang, S.; Giri, A.; Wu, P.-H.; Marchand, J.; Celedon, A.; Hale, C. M.; Sun, S. X.; Hodzic, D.; Wirtz, D. The distinct roles of the nucleus and nucleus-cytoskeleton connections in three-dimensional cell migration. *Sci. Rep.* 2012, 2, No. 488.
63. Wen, J. H.; Vincent, L. G.; Fuhrmann, A.; Choi, Y. S.; Hribar, K. C.; Taylor-Weiner, H.; Chen, S.; Engler, A. J. Interplay of matrix stiffness and protein tethering in stem cell differentiation. *Nat. Mater.* 2014, 13, 979-987.
64. Thievessen, I.; Thompson, P. M.; Berlemont, S.; Plevock, K. M.; Plotnikov, S. V.; Zemljic-Harpf, A.; Ross, R. S.; Davidson, M. W.; Danuser, G.; Campbell, S. L.; Waterman, C. M. Vinculin-actin interaction couples actin retrograde flow to focal adhesions, but is dispensable for focal adhesion growth. *J. Cell Biol.* 2013, 202, 163-177.
65. Humphries, J. D.; Wang, P.; Streuli, C.; Geiger, B.; Humphries, M. J.; Ballestrem, C. Vinculin controls focal adhesion formation by direct interactions with talin and actin. *J. Cell. Biol.* 2007, 179, 1043-1057.
66. Ode, A.; Schoon, J.; Kurtz, A.; Gaetjen, M.; Ode, J. E.; Geissler, S.; Duda, G. N. CD73/5'-ecto-nucleotidase acts as a regulatory factor in osteo-/chondrogenic differentiation of mechanically stimulated mesenchymal stromal cells. *Eur. Cells Mater.* 2013, 25, 37-47.
67. Aslan, H.; Zilberman, Y.; Kandel, L.; Liebergall, M.; Oskouian, R. J.; Gazit, D.; Gazit, Z. Osteogenic differentiation of noncultured immunoisolated bone marrow-derived CD105+ cells. *Stem Cells* 2006, 24, 1728-1737.
68. Huang, S.; Ingber, D. E. The structural and mechanical complexity of cell-growth control. *Nat. Cell Biol.* 1999, 1, No. E131.
69. McBeath, R.; Pirone, D. M.; Nelson, C. M.; Bhadriraju, K.; Chen, C. S. Cell shape, cytoskeletal tension, and RhoA regulate stem cell lineage commitment. *Dev. Cell* 2004, 6, 483-495.
70. Katz, B.-Z.; Zamir, E.; Bershadsky, A.; Kam, Z.; Yamada, K. M.; Geiger, B. Physical state of the extracellular matrix regulates the structure and molecular composition of cell-matrix adhesions. *Mol. Biol. Cell* 2000, 11, 1047-1060.
71. Cukierman, E.; Pankov, R.; Stevens, D. R.; Yamada, K. M. Taking cell-matrix adhesions to the third dimension. *Science* 2001, 294, 1708-1712.
72. Fischbach, C.; Kong, H. J.; Hsiong, S. X.; Evangelista, M. B.; Yuen, W.; Mooney, D. J. Cancer cell angiogenic 73. Hsiong, S. X.; Boontheekul, T.; Huebsch, N.; Mooney, D. J. Cyclic arginine-glycine-aspartate peptides enhance three-dimensional stem cell osteogenic differentiation. *Tissue Eng., Part A* 2009, 15, 263-272.
74. Park, J. S.; Huang, N. F.; Kurpinski, K. T.; Patel, S.; Hsu, S.; Li, S. Mechanobiology of mesenchymal stem cells and their use in cardiovascular repair. *Front. Biosci.* 2007, 12, 5098-5116.
75. Tan, S.; Fang, J. Y.; Yang, Z.; Nimni, M. E.; Han, B. The synergetic effect of hydrogel stiffness and growth factor on osteogenic differentiation. *Biomaterials* 2014, 35, 5294-5306.
76. Knight, B.; Laukaitis, C.; Akhtar, N.; Hotchin, N. A.; Edlund, M.; Horwitz, A. R. Visualizing muscle cell migration in situ. *Curr. Biol.* 2000, 10, 576-585.
77. Roskelley, C.; Desprez, P.; Bissell, M. Extracellular matrix-dependent tissue-specific gene expression in mammary epithelial cells requires both physical and biochemical signal transduction. *Proc. Natl. Acad. Sci. U.S.A.* 1994, 91, 12378-12382.
78. Thievessen, I.; Fakhri, N.; Steinwachs, J.; Kraus, V.; McIsaac, R. S.; Gao, L.; Chen, B.-C.; Baird, M. A.; Davidson, M. W.; Betzig, E.; et al. Vinculin is required for cell polarization, migration, and extracellular matrix remodeling in 3D collagen. *FASEB J.* 2015, 29, 4555-4567.
79. Case, L. B.; Baird, M. A.; Shtengel, G.; Campbell, S. L.; Hess, H. F.; Davidson, M. W.; Waterman, C. M. Molecular mechanism of vinculin activation and nanoscale spatial organization in focal adhesions. *Nat. Cell Biol.* 2015, 17, 880-892.
80. Carisey, A.; Ballestrem, C. Vinculin, an adapter protein in control of cell adhesion signalling. *Eur. J. Cell Biol.* 2011, 90, 157-163.
81. Xu, W.; Baribault, H.; Adamson, E. D. Vinculin knockout results in heart and brain defects during embryonic development. *Development* 1998, 125, 327-337.
82. Kumar, G.; Tison, C. K.; Chatterjee, K.; Pine, P. S.; McDaniel, J. H.; Salit, M. L.; Young, M. F.; Simon, C. G., Jr. The determination of stem cell fate by 3D scaffold structures through the control of cell shape. *Biomaterials* 2011, 32, 9188-9196.
83. Pablo Rodríguez, J.; González, M.; Ríos, S.; Cambiazo, V. Cytoskeletal organization of human mesenchymal stem cells (MSC) changes during their osteogenic differentiation. *J. Cell. Biochem.* 2004, 93, 721-731.
84. Treiser, M. D.; Yang, E. H.; Gordonov, S.; Cohen, D. M.; Androulakis, I. P.; Kohn, J.; Chen, C. S.; Moghe, P. V. Cytoskeleton-based forecasting of stem cell lineage fates. *Proc. Natl. Acad. Sci. U.S.A.* 2010, 107, 610-615.
85. Hunter, G. K.; Hauschka, P. V.; Poole, R. A.; Rosenberg, L. C.; Goldberg, H. A. Nucleation and inhibition of hydroxyapatite formation by mineralized tissue proteins. *Biochem. J.* 1996, 317, 59-64.
86. Wang, J.; Cui, X.; Zhou, Y.; Xiang, Q. Core-shell PLGA/collagen nanofibers loaded with recombinant FN/CDHs as bone tissue engineering scaffolds. *Connect. Tissue Res.* 2014, 55, 292-298.
87. Khan, S. N.; Lane, J. M. Bone Tissue Engineering: Basic Science and Clinical Concepts. *Orthopedic Tissue Engineering*; CRC Press, 2004; pp 177-194.
88. Oreffo, R. O.; Kusec, V.; Romberg, S.; Triffitt, J. T. Human bone marrow osteoprogenitors express estrogen receptor-alpha and bone morphogenetic proteins 2 and 4 mRNA during osteoblastic differentiation. *J. Cell. Biochem.* 1999, 75, 382-392.
89. Frank, O.; Heim, M.; Jakob, M.; Barbero, A.; Schäfer, D.; Bendik, I.; Dick, W.; Heberer, M.; Martin, I. Real-time quantitative RT-PCR analysis of human bone marrow stromal cells during osteogenic differentiation in vitro. *J. Cell. Biochem.* 2002, 85, 737-746.
90. Miron, R.; Zhang, Y. Osteoinduction: a review of old concepts with new standards. *J. Dent. Res.* 2012, 91, 736-744.
91. Rittling, S. R.; Matsumoto, H. N.; Mckee, M. D.; Nanci, A.; An, X. R.; Novick, K. E.; Kowalski, A. J.; Noda, M.; Denhardt, D. T. Mice lacking osteopontin show normal development and bone structure but display altered osteoclast formation in vitro. *J. Bone Miner. Res.* 1998, 13, 1101-1111.
92. Chellaiah, M. A.; Kizer, N.; Biswas, R.; Alvarez, U.; Strauss-Schoenberger, J.; Rifas, L.; Rittling, S. R.; Denhardt, D. T.; Hruska, K. A. Osteopontin deficiency produces osteoclast dysfunction due to reduced CD44 surface expression. *Mol. Biol. Cell* 2003, 14, 173-189.
93. Bax, D. V.; Rodgers, U. R.; Bilek, M. M.; Weiss, A. S. Cell adhesion to tropoelastin is mediated via the C-terminal GRKRK motif and integrin αVβ3. *J. Biol. Chem.* 2009, 284, 28616-28623.
94. Taddese, S.; Weiss, A. S.; Jahreis, G.; Neubert, R. H.; Schmelzer, C. E. In vitro degradation of human tropoelastin by MMP-12 and the generation of matrikines from domain 24. *Matrix Biol.* 2009, 28, 84-91.
95. Getie, M.; Schmelzer, C.; Neubert, R. Characterization of peptides resulting from digestion of human skin elastin with elastase. *Proteins* 2005, 61, 649-657.
96. Phillips, J. E.; Petrie, T. A.; Creighton, F. P.; García, A. J. Human mesenchymal stem cell differentiation on self-assembledmonolayers presenting different surface chemistries. *Acta Biomater.* 2010, 6, 12-20.
97. Nemir, S.; West, J. L. Synthetic materials in the study of cell response to substrate rigidity. *Ann. Biomed. Eng.* 2010, 38, 2-20.
98. Holst, J.; Watson, S.; Lord, M. S.; Eamegdool, S. S.; Bax, D. V.; Nivison-Smith, L. B.; Kondyurin, A.; Ma, L.; Oberhauser, A. F.; Weiss, A. S.; Rasko, J. E. J. Substrate elasticity provides mechanical signals for the expansion of hemopoietic stem and progenitor cells. *Nat. Biotechnol.* 2010, 28, 1123.
99. Rowlands, A. S.; George, P. A.; Cooper-White, J. J. Directing osteogenic and myogenic differentiation of MSCs: interplay of stiffness and adhesive ligand presentation. *Am. J. Physiol.: Cell Physiol.* 2008, 295, C1037-C1044.
100. Saha, K.; Keung, A. J.; Irwin, E. F.; Li, Y.; Little, L.; Schaffer, D. V.; Healy, K. E. Substrate modulus directs neural stem cell behavior. *Biophys. J.* 2008, 95, 4426-4438.
101. Huebsch, N.; Arany, P. R.; Mao, A. S.; Shvartsman, D.; Ali, O. A.; Bencherif, S. A.; Rivera-Feliciano, J.; Mooney, D. J. Harnessing traction-mediated manipulation of the cell/matrix interface to control stem-cell fate. *Nat. Mater.* 2010, 9, 518.
102. Kabiri, K.; Omidian, H.; Hashemi, S.; Zohuriaan-Mehr, M. Synthesis of fast-swelling superabsorbent hydrogels: effect of cross-linker type and concentration on porosity and absorption rate. *Eur. Polym. J.* 2003, 39, 1341-1348.
103. Hale, B. W.; Goodrich, L. R.; Frisbie, D. D.; McIlwraith, C. W.; Kisiday, J. D. Effect of scaffold dilution on migration of mesenchymal stem cells from fibrin hydrogels. *Am. J. Vet. Res.* 2012, 73, 313-318.

104. Cuchiara, M. P.; Allen, A. C.; Chen, T. M.; Miller, J. S.; West, J. L. Multilayer microfluidic PEGDA hydrogels. *Biomaterials* 2010, 31, 5491-5497.
105. Cheng, R.; Yan, Y.; Liu, H.; Chen, H.; Pan, G.; Deng, L.; Cui, W. Mechanically enhanced lipo-hydrogel with controlled release of multi-type drugs for bone regeneration. *Appl. Mater. Today* 2018, 12, 294-308.
106. Engler, A. J.; Sen, S.; Sweeney, H. L.; Discher, D. E. Matrix elasticity directs stem cell lineage specification. *Cell* 2006, 126, 677-689.
107. Sivaraj, K. K.; Adams, R. H. Blood vessel formation and function in bone. *Development* 2016, 143, 2706-2715.
108. Kim, S.; Cha, C. Enhanced mechanical and electrical properties of heteroscaled hydrogels infused with aqueous-dispersible hybrid nanofibers. *Biofabrication* 2020, 12, No. 015020.
109. Hwang, T. L.; Shaka, A. J., Water Suppression That Works. Excitation Sculpting Using Arbitrary Wave-Forms and Pulsed-Field Gradients. *J. Magn. Reson.* 1995, 112, (2), 275-279.
110. Derome, A. E.; Williamson, M. P., Rapid-Pulsing Artifacts in Double-Quantum-Filtered COSY. *J. Magn. Reson.* 1990, 88, (1), 177-185.
111. Piotto, M.; Saudek, V.; Sklenář, V., Gradient-Tailored Excitation for Single-Quantum NMR Spectroscopy of Aqueous Solutions. *J. Biomol. NMR* 1992, 2, (6), 661-665.
112. Sklenar, V.; Piotto, M.; Leppik, R.; Saudek, V., Gradient-Tailored Water Suppression for 1H-15N HSQC Experiments Optimized to Retain Full Sensitivity. *J. Magn. Reson.* 1993, 102, (2), 241-245.
113. Gilbert, D. F.; Erdmann, G.; Zhang, X.; Fritzsche, A.; Demir, K.; Jaedicke, A.; Muehlenberg, K.; Wanker, E. E.; Boutros, M., A novel multiplex cell viability assay for high-throughput RNAi screening. *PloS One* 2011, 6, (12), e28338.

All documents, patents, journal articles and other materials cited in the present application are incorporated herein by reference.

While the present disclosure has been disclosed with references to certain embodiments, numerous modifications, alterations, and changes to the described embodiments are possible without departing from the sphere and scope of the present disclosure, as defined in the appended claims. Accordingly, it is intended that the present disclosure not be limited to the described embodiments, but that it has the full scope defined by the language of the following claims, and equivalents thereof.

What is claimed is:

1. A 3-dimensional osteo-tissue graft comprising:
   live mesenchymal stem cells (MSCs); and
   ultrashort self-assembling peptide scaffolds,
   wherein the stiffness of the peptide scaffolds is 16-25 kPa,
   wherein at least one osteogenic marker selected from the group consisting of bone morphogenetic protein (BMP-2) bone sialoprotein 2 (IBSP), osteopontin (OPN), osterix (OSX), RUNX2, osteocalcin and alkaline phosphatase (ALP), is expressed.

2. The 3-dimensional osteo-tissue graft of claim 1, wherein the ultrashort self-assembling peptide is at least one peptide selected from a group of peptides having a general formula selected from:

$A_nB_mX$, $B_mA_nX$, $XA_nB_m$, and $XB_mA_n$ wherein the total number of amino acids of the ultrashort peptide does not exceed 7 amino acids;
   wherein A is an aliphatic amino acid, selected from the group consisting of: isoleucine, leucine or any combination thereof, with n being an integer being selected from 0-5;
   wherein B is comprised of at least one aromatic amino acid selected from the group consisting of: tyrosine, tryptophan, phenylalanine, hydrophobic amino acid phenylalanine, or comprised of a peptidomimetic amino acid that is the aliphatic counterpart of the aromatic amino acid, such as cyclohexylalanine, which is the counterpart of amino acid phenylalanine with m being an integer being selected from 0-3;
   wherein X is comprised of a polar amino acid, selected from the group consisting of: aspartic acid, glutamic acid, lysine, arginine, histidine, cysteine, serine, threonine, asparagine, and glutamine.

3. The 3-dimensional osteo-tissue graft of claim 2, wherein the ultrashort self-assembling peptides are tetrameric self-assembling peptides.

4. The 3-dimensional osteo-tissue graft of claim 3, wherein the ultrashort self-assembling peptide made of the scaffolds is at least one peptide selected from the group consisting of IVFK, and IVZK.

5. The 3-dimensional osteo-tissue graft of claim 3, wherein a concentration of ultrashort self-assembling peptide used to form the scaffolds is 3 mg/ml-8 mg/ml.

6. The 3-dimensional osteo-tissue graft of claim 1, wherein a density of the MSCs within the peptide scaffold is at least 40,000 cells per well.

7. The 3-dimensional osteo-tissue graft of claim 1, wherein the MSCs cultured within the 3-dimensional osteo-tissue graft differentiate to osteocytes after culturing in an osteogenic induction media.

8. The 3-dimensional osteo-tissue graft of claim 7, wherein the MSCs cultured within the 3-dimensional osteo-tissue graft are cultured in an osteogenic induction media for at least 7 days.

9. The 3-dimensional osteo-tissue graft of claim 8, wherein a concentration of mineral deposits in the grafts has an absorbance at 405 nm of at least 0.4 when quantified using Alizarin Red Staining after at least 14 days of culturing.

10. The 3-dimensional osteo-tissue graft of claim 1 further comprising live umbilical vein endothelial cells.

11. The 3-dimensional osteo-tissue graft of claim 10, wherein a concentration of human umbilical vein endothelial cells within the peptide scaffold is at least 40,000 cells per well.

12. The 3-dimensional osteo-tissue graft of claim 10, wherein the umbilical vein endothelial cells form tube structure, vessel junctions and vessel nodes within 24 h after culturing within the peptide scaffolds.

13. A surgical implant comprising the 3-dimensional osteo-tissue graft of claim 1, wherein the surgical implant is used in cellular replacement therapies for bone damages and disorders.

14. A method to create a 3-dimensional osteo-tissue graft comprising:
   suspending mesenchymal stem cells (MSCs) in buffer solution;
   dissolving an ultrashort self-assembling peptide in buffer solution;
   loading a 3D bioprinter with the suspended MSCs and peptide solution;
   creating the 3-dimensional osteo-tissue graft using the 3D bioprinter or manually;
   incubating the 3-dimensional osteo-tissue graft for 5 min at 37° C.;
   culturing the 3-dimensional osteo-tissue graft in complete media; and
   3D culturing the MSCs by keeping the 3-dimensional osteo-tissue graft in osteogenic induction media or basal stem cell growth media,
   wherein the 3-dimensional osteo-tissue graft comprises live MSCs and at least one ultrashort self-assembling peptide scaffolds,
   wherein the stiffness of the peptide scaffolds is 20-25 kPa.

15. The method to create a 3-dimensional osteo-tissue graft of claim 14, wherein the ultrashort self-assembling peptides are tetrameric self-assembling peptides.

16. The method to create a 3-dimensional osteo-tissue graft of claim 15, wherein the ultrashort self-assembling peptide made of the scaffolds is at least one peptide selected from the group consisting of IVFK, and IVZK.

* * * * *